US012590966B2

(12) United States Patent
Gutierrez et al.

(10) Patent No.: US 12,590,966 B2
(45) Date of Patent: Mar. 31, 2026

(54) METHOD FOR TREATING CANCER

(71) Applicant: THE CHILDREN'S MEDICAL CENTER CORPORATION, Boston, MA (US)

(72) Inventors: Alejandro Gutierrez, Brookline, MA (US); Laura Hinze, Bueckeburg (DE)

(73) Assignee: THE CHILDREN'S MEDICAL CENTER CORPORATION

( * ) Notice: Subject to any disclaimer, the term of this patent is extended or adjusted under 35 U.S.C. 154(b) by 569 days.

(21) Appl. No.: 17/773,233

(22) PCT Filed: Nov. 3, 2020

(86) PCT No.: PCT/US2020/058703

§ 371 (c)(1),
(2) Date: Apr. 29, 2022

(87) PCT Pub. No.: WO2021/091896

PCT Pub. Date: May 14, 2021

(65) Prior Publication Data

US 2023/0003732 A1 Jan. 5, 2023

Related U.S. Application Data

(60) Provisional application No. 63/061,367, filed on Aug. 5, 2020, provisional application No. 62/951,664, filed on Dec. 20, 2019, provisional application No. 62/930,258, filed on Nov. 4, 2019.

(51) Int. Cl.

| | |
|---|---|
| ***G01N 33/574*** | (2006.01) |
| ***A61K 31/437*** | (2006.01) |
| ***A61K 31/7105*** | (2006.01) |
| ***A61K 31/713*** | (2006.01) |
| ***C12N 9/82*** | (2006.01) |

(52) U.S. Cl.

CPC ..... *G01N 33/57484* (2013.01); *A61K 31/437* (2013.01); *A61K 31/7105* (2013.01); *A61K 31/713* (2013.01); *C12N 9/82* (2013.01); *C12Y 305/01001* (2013.01); *G01N 2333/91215* (2013.01)

(58) Field of Classification Search

None

See application file for complete search history.

(56) References Cited

FOREIGN PATENT DOCUMENTS

WO WO-2013063560 A2 * 5/2013 ........... A61K 31/196

OTHER PUBLICATIONS

Banerji, V. et al. 2012. The intersection of genetic and chemical genomic screens identifies GSK-3alpha as a target in human acute myeloid leukemia. Journal of Clinical Investigation 122(3): 935-947; specif. pp. 935, 943 (Year: 2012).*

Metcalfe, C. et al. 2011. Inhibition of GSK3 by Wnt signaling-two contrasting models. Journal of Cell Science 124: 3537-3544; specif. pp. 3537, 3543 (Year: 2011).*

Mikesch, J.H. et al. 2007. The emerging role of Wnt signaling in the pathogenesis of acute myeloid leukemia. Leukemia 21: 1638-1647; specif. pp. 1638, 1639 (Year: 2007).*

Hinze, L. et al. 2018. Synthetic lethality of Wnt pathway activation and asparaginase in drug-resistant acute leukemias. Blood 132(Suppl. 1): 1-3 (Year: 2018).*

He et al. "Regulation of GSK3 cellular location by FRAT modulates mTORC1-dependent cell growth and sensitivity to rapamycin." Proceedings of the National Academy of Sciences 116(39): 19523-19529 (2019).

Hinze et al. "Synthetic lethality of Wnt pathway activation and asparaginase in drug-resistant acute leukemias." Cancer Cell 35(4): 664-676 (2019).

* cited by examiner

*Primary Examiner* — Adam Weidner
*Assistant Examiner* — Sharon M. Papciak
(74) *Attorney, Agent, or Firm* — NIXON PEABODY LLP; David S. Resnick; Ravinderjit S. Braich

(57) ABSTRACT

Described herein are methods and compositions for treating cancer. Aspects of the invention relate to determining if a biological sample obtained from a subject for GSK3α bodies (puncta), e.g., in response to asparaginase treatment, and administering to a subject having cancer an asparaginase and an agent that inhibits GSK3α to a subject who has been identified as forming GSK3α-positive bodies.

17 Claims, 36 Drawing Sheets

Specification includes a Sequence Listing.

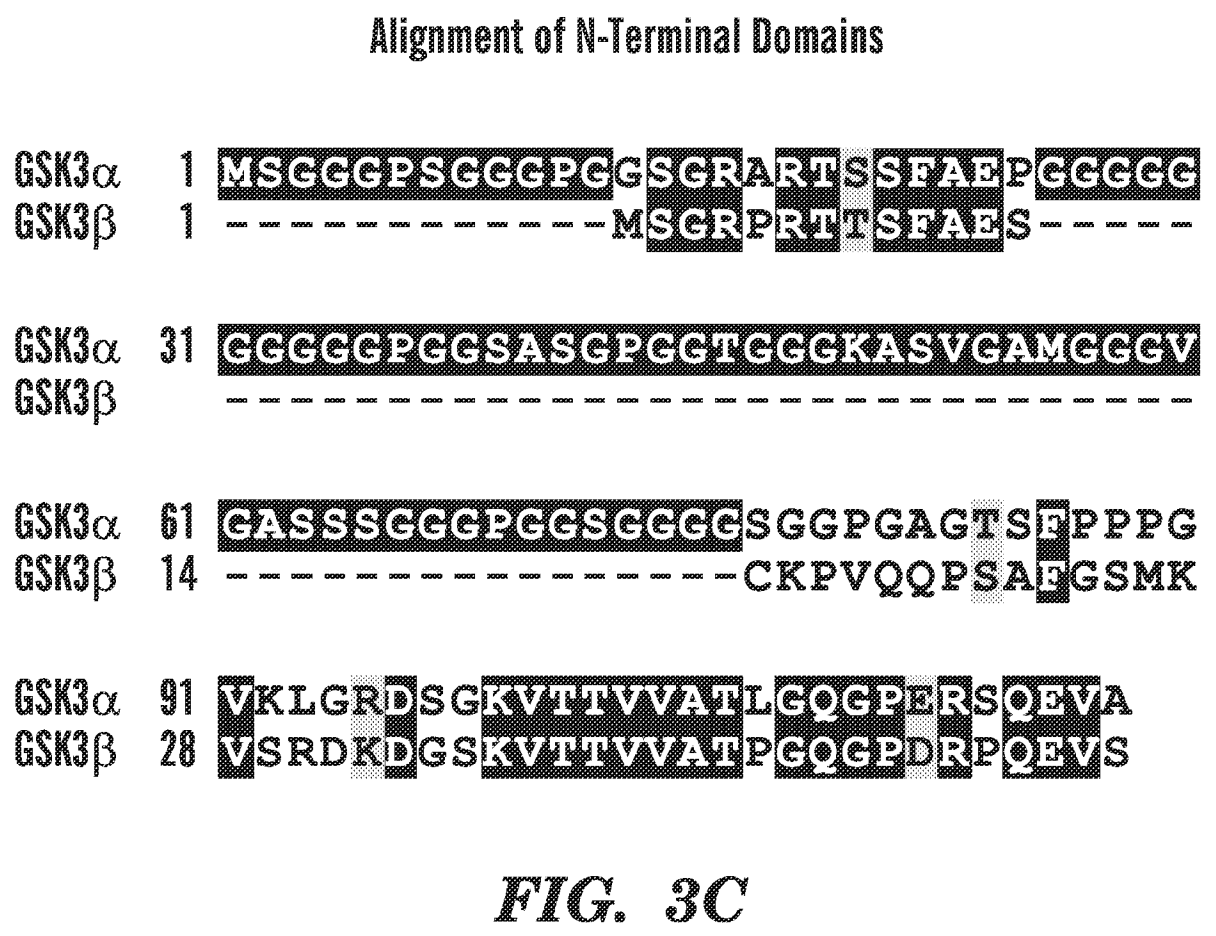

Alignment of N-Terminal Domains

```
GSK3α   1  MSGGGPSGGGPGGSGRARTSSFAEPGGGGG
GSK3β   1  ------------MSGRPRTTSFAES-----

GSK3α  31  GGGGGPGGSASGPGGTGGGKASVGAMGGGV
GSK3β      ------------------------------

GSK3α  61  GASSSGGGPGGSGGGGSGGPGAGTSFPPPG
GSK3β  14  ----------------CKPVQQPSAFGSMK

GSK3α  91  VKLGRDSGKVTTVVATLGQGPERSQEVA
GSK3β  28  VSRDKDGSKVTTVVATPGQGPDRPQEVS
```

*FIG. 3C*

```
Human|P49840        MSGGGPSGGGPGGSGRARTSSFAEPGGGGGGGGGGPGGSASGPGGTGGGKASVGAMGGGV 60
Mouse|Q2NL51        MSGGGPSGGGPGGSGRARTSSFAEPGGGGGGGGGGPGGSASGPGGTGGGKASVGAMGGGV 60
Pig|F1RGH8          MSGGAPSGGGPGGSGRARTSSFAEPGGGGGGGGGGPGGSASGPGGSGGGKPSVGAMGGGV 60
Cat|M3X6U4          MSGGGPSGGGPGGSGRARTSSFAEPGGGGGGGGGGPGGSASGPGGSGGGKASVGAMGGGV 60
Beluga|A0A2Y9P7P    MSGGAPSGGGPGGSGRARTSSFAEPGGGGGGGGGGPGGSASGPGGSGGGKTSVGAMGGGV 60

Human|P49840        GASSSGGGPGGSGGGGSGGPGAGTSFPPPGVKLGRDSGKVTTVVATLGQGPERSQEVAYT 120
Mouse|Q2NL51        GASSSGGGPSGSGGGGSGGPGAGTSFPPPGVKLGRDSGKVTTVVATVGQGPERSQEVAYT 120
Pig|F1RGH8          GASSSGGGPSGSGGGGSGGPGAGTSFPPPGVKLGRDSGKVTTVVATLGQGPERSQEVAYT 120
Cat|M3X6U4          GASSSGGGPSGSGGGGSGGPGAGTSFPPPGVKLGRDSGKVTTVVATLGQGPERSQEVAYT 120
Beluga|A0A2Y9P7P    GASSSGGGPSGSGGGGSGGPGAGTSFPPPGVKLGRDSGKVTTVVATLGQGPERSQEVAYT 120

Human|P49840        DIKVIGNGSFGVVYQARLAETRELVAIKKVLQDKRFKNRELQIMRKLDHCNIVRLRYFFY 180
Mouse|Q2NL51        DIKVIGNGSFGVVYQARLAETRELVAIKKVLQDKRFKNRELQIMRKLDHCNIVRLRYFFY 180
Pig|F1RGH8          DIKVIGNGSFGVVYQARLADTRELVAIKKVLQDKRFKNRELQIMRKLDHCNIVRLRYFFY 180
Cat|M3X6U4          DIKVIGNGSFGVVYQARLAETRELVAIKKVLQDKRFKNRELQIMRKLDHCNIVRLRYFFY 180
Beluga|A0A2Y9P7P    DIKVIGSGSFGVVYQARLADTRELVAIKKVLQDKRFKNRELQIMRKLDHCNIVRLRYFFY 180
```

N-terminal domain
Kinase and axin-binding domain
C-terminal domain

FIG. 22A

```
Human|P49840        SSGEKKDELYLNLVLEYVPETVYRVARHFTKAKLTIPILYVKVYMYQLFRSLAYIHSQGV 240
Mouse|Q2NL51        SSGEKKDELYLNLVLEYVPETVYRVARHFTKAKLITPIIYIKVYMYQLFRSLAYIHSQGV 240
Pig|F1RGH8          SSGEKKDELYLNLVLEYVPETVYRVARHFTKAKLTIPIIYVKVYMYQLFRSLAYIHSQGV 240
Cat|M3X6U4          SSGEKKDELYLNLVLEYVPETVYRVARHFTKAKLTIPIIYVKVYMYQLFRSLAYIHSQGV 240
Beluga|A0A2Y9P7P    SSGEKKDELYLNLVLEYVPETVYRVARHFTKAKLTIPIIYVKVYMYQLFRSLAYIHSQGV 240

Human|P49840        CHRDIKPQNLLVDPDTAVLKLCDFGSAKQLVRGEPNVSYICSRYYRAPELIFGATDYTSS 300
Mouse|Q2NL51        CHRDIKPQNLLVDPDTAVLKLCDFGSAKQLVRGEPNVSYICSRYYRAPELIFGATDYTSS 300
Pig|F1RGH8          CHRDIKPQNLLVDPDTAVLKLCDFGSAKQLVRGEPNVSYICSRYYRAPELIFGATDYTSS 300
Cat|M3X6U4          CHRDIKPQNLLVDPDTAVLKLCDFGSAKQLVRGEPNVSYICSRYYRAPELIFGATDYTSS 300
Beluga|A0A2Y9P7P    CHRDIKPQNLLVDPDTAVLKLCDFGSAKQLVRGEPNVSYICSRYYRAPELIFGATDYTSS 300

Human|P49840        IDVWSAGCVLAELLLGQPIFPGDSGVDQLVEIIKVLGTPTREQIREMNPNYTEFKFPQIK 360
Mouse|Q2NL51        IDVWSAGCVLAELLLGQPIFPGDSGVDQLVEIIKVLGTPTREQIREMNPNYTEFKFPQIK 360
Pig|F1RGH8          IDVWSAGCVLAELLLGQPIFPGDSGVDQLVEIIKVLGTPTREQIREMNPNYTEFKFPQIK 360
Cat|M3X6U4          IDVWSAGCVLAELLLGQPIFPGDSGVDQLVEIIKVLGTPTREQIREMNPNYTEFKFPQIK 360
Beluga|A0A2Y9P7P    IDVWSAGCVLAELLLGQPIFPGDSGVDQLVEIIKVLGTPTREQIREMNPNYTEFKFPQIK 360
```

N-terminal domain
Kinase and axin-binding domain
C-terminal domain

FIG. 22B

```
Human|P49840        AHPWTKVFKS-RTPPEAIALCSSLLEYTPSSRLSPLEACAHSFFDELRCLGTQLPNNRPL 419
Mouse|Q2NL51        AHPWTKVFKSSKTPPEAIALCSSLLEYTPSSRLSPLEACAHSFFDELRRLGAQLPNDRPL 420
Pig|F1RGH8          AHPWTKVFKS-RTPPEAITLCSSLLEYTPSSRLSPLEACAHNFFDELRCPGTQLPNNRPL 419
Cat|M3X6U4          AHPWTKVFKS-RTPPEAIALCSSLLEYTPSSRLSPLEACAHSFFDELRCHGTQLPNNRPL 419
Beluga|A0A2Y9P7P    AHPWTKVFKS-RTPPEAIALCSSLLEYTPSSRLSPLEACAHSFFDELRCPGTQLPNNRPL 419

Human|P49840        PPLFNFSAGELSIQPSLNAILIPPHLRSPAGTTT-----LTPSSQALTETPTSSDWQSTD 474
Mouse|Q2NL51        PPLFNFSPGELSIQPSLNAILIPPHLRSPAGPASPLTTSYNPSSQALTEAQTGQDWQPSD 480
Pig|F1RGH8          PPLFNFSPGELTIQPSLNAILIPPHLRSPAGTAS-----LTSSSQALSETPTGPDWQSTD 474
Cat|M3X6U4          PPLFNFSPGELSIQPSLNAILIPPHLRSPAGTAT-----LTPSSQALSEAQTGSEWQSTD 474
Beluga|A0A2Y9P7P    PPLFNFSPGELTIQPSLNAILIPPHLRSPAGTAS-----LTPSSQALSEAQTGPDWQSTD 474

Human|P49840        ATPTLTNSS--------------------------------------------------- 483
Mouse|Q2NL51        ATTATLASSS-------------------------------------------------- 490
Pig|F1RGH8          ATTPSLTLPEGATNYPSIWEPQVGLGRGGHSPSSSCPDWAPRLEGRENVDSHRPTWPLPL 534
Cat|M3X6U4          ATAPLTNSS--------------------------------------------------- 483
Beluga|A0A2Y9P7P    ATAPLTNSS--------------------------------------------------- 483
```

N-terminal domain
Kinase and axin-binding domain
C-terminal domain

FIG. 22C

| | | |
|---|---|---|
| Human\|P49840 | -------------------------------- | 483 |
| Mouse\|Q2NL51 | -------------------------------- | 490 |
| Pig\|F1RGH8 | LQLCPCSCPLPLRPPPFPPPWRAGAVGELLMS | 566 |
| Cat\|M3X6U4 | -------------------------------- | 483 |
| Beluga\|A0A2Y9P7P | -------------------------------- | 483 |

N-terminal domain
Kinase and axin-binding domain
C-terminal domain

FIG. 22D

METHOD FOR TREATING CANCER

CROSS REFERENCE TO RELATED APPLICATION

This application is a 35 U.S.C. § 371 National Phase Entry Application of International Application No. PCT/US2020/058703 filed Nov. 3, 2020, which designates the U.S. and claims benefit under 35 U.S.C. § 119 (e) of U.S. Provisional Application No. 62/930,258, filed on Nov. 4, 2019; 62/951,664, filed on Dec. 20, 2019; and 63/061,367, filed Aug. 5, 2020, the contents of which is incorporated herein by reference their entireties.

GOVERNMENT SUPPORT

This invention was made with Government support under Grant No. R01 CA193651 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Oct. 28, 2020, is named 701039-096430WOPT_SL.txt and is 14,191 bytes in size.

FIELD OF THE INVENTION

The field of the invention relates to the treatment of cancer.

BACKGROUND

Leukemia is the most common of pediatric cancers accounting for about 30% of diagnoses. There are two main subtypes; acute lymphoblastic leukemia (ALL) and acute myeloid leukemia (AML). AML is less common, accounting for approximately 18% of childhood leukemia diagnoses. These leukemia types also occur in adults, and AML becomes more common in older individuals. The etiology of the two subtypes is likely quite different based on both cell lineage and epidemiological studies of incidence and risk factors. Aggressive chemotherapies are required to improve the prognosis of patients diagnoses with leukemias such as ALL or AML.

Asparaginase, a bacterial enzyme that depletes the non-essential amino acid asparagine, is an integral component of acute leukemia therapy[1,2]. The antineoplastic effects of asparaginase are likely caused by its depletion of extracellular asparagine and glutamine creating a state of amino acid deficiency and subsequent inhibition of protein synthesis. However, other mechanisms remain to be identified. Despite its efficacy in ALL, asparaginase has been used only occasionally in the treatment of other leukemias and solid tumors. Previous in vitro studies have observed varied response to asparaginase in acute myeloid leukemia (AML) across the French-American-British subtypes. Asparaginase resistance remains a common clinical problem for leukemia patients where the biologic basis of the resistance is poorly understood.

SUMMARY OF THE INVENTION

The invention described herein is related, in part, to the discovery that GSK3α puncta are formed in cells in response to asparagine starvation. Further experimentation described herein finds that GSK3α puncta formation in response to asparagine starvation significantly correlated with resistance to asparaginase in T-ALL, B-ALL and AML. Accordingly, one aspect described herein provides a method of treating cancer comprising (a) obtaining a biological sample from a subject having cancer; (b) assaying the sample and identifying the cancer as forming GSK3α-positive puncta; and (c) administering an asparaginase and an agent that inhibits GSK3α to a subject who has been identified as forming GSK3α-positive puncta.

Another aspect described herein provides a method of treating cancer comprising (a) receiving the results of an assay that identifies a subject as having a cancer forming GSK3α-positive puncta; and (b) administering an asparaginase and an agent that inhibits GSK3α to a subject who has been identified as forming GSK3α-positive puncta.

Another aspect described herein provides a method of treating asparaginase-resistant cancer comprising: (a) obtaining a biological sample from a subject having cancer; (b) assaying the sample to identify for GSK3α-positive puncta; (c) identifying a subject as having asparaginase-resistant cancer if the cancer forms GSK3α-positive puncta; and (d) administering an asparaginase and an agent that inhibits GSK3α to a subject who has been identified as having asparaginase-resistant cancer.

Yet another aspect described herein provides a method of treating asparaginase-resistant cancer comprising (a) receiving the results of an assay that identifies a subject as having a cancer forming GSK3α-positive puncta; (b) identifying a subject as having asparaginase-resistant cancer if the cancer forms GSK3α-positive puncta; and (c) administering an asparaginase and an agent that inhibits GSK3α to a subject who has been identified as having asparaginase-resistant cancer.

In one embodiment of any aspect, the GSK3α-positive puncta are formed in response to asparagine starvation.

In one embodiment of any aspect, the GSK3α-positive puncta are formed following contact with an asparaginase treatment.

In one embodiment of any aspect, the assaying is treating the sample with an asparaginase, or culturing the sample in conditions of asparagine starvation or amino acid starvation.

In one embodiment of any aspect, the cancer is selected from the list consisting of: a carcinoma, a melanoma, a sarcoma, a myeloma, a leukemia, and a lymphoma. In one embodiment of any aspect, the cancer is a solid tumor. In one embodiment of any aspect, the cancer is colorectal or pancreatic cancer.

In one embodiment of any aspect, the leukemia is acute myeloid leukemia (AML), Chronic myeloid leukemia (CML), Acute lymphocytic leukemia (ALL), and Chronic lymphocytic leukemia (CLL).

In one embodiment of any aspect, the cancer is metastatic.

In one embodiment of any aspect, the biological sample is a biopsied sample, a tissue sample or a blood sample. In one embodiment of any aspect, the biopsied sample is a tumor sample.

In one embodiment of any aspect, the asparaginase is selected from the group consisting of: L-asparaginase (Elspar), pegaspargase (PEG-asparaginase; Oncaspar), SC-PEG asparaginase, Calaspargase pegol (Cal-PEG; SHP663), *Erwinia* asparaginase (Erwinaze), cristantaspase, and Asparaginase medac.

In one embodiment of any aspect, the agent that inhibits GSK3α is selected from the group consisting of a small molecule, an antibody, a peptide, a genome editing system, an antisense oligonucleotide, and an RNAi.

In one embodiment of any aspect, the small molecule is selected from the group consisting of: BRD0705, BRD4963, BRD1652, BRD3731, CHIR-98014, LY2090314, AZD1080, CHIR-99021 (CT99021) HCl, CHIR-99021 (CT99021), BIO-acetoxime, SB216763, SB415286, Abemaciclib (LY2835210), AT-9283, RGB-286638, PHA-793887, AT-7519, AZD-5438, OTS-167, 9-ING-41, Tideglusib (NP031112), and AR-A014418.

In one embodiment of any aspect, the small molecule is BRD0705.

In one embodiment of any aspect, the RNAi is a microRNA, an siRNA, or a shRNA.

In one embodiment of any aspect, inhibiting GSK3α is inhibiting the expression level and/or activity of GSK3α. In one embodiment of any aspect, the expression level and/or activity of GSK3α is inhibited by at least 50%, at least 60%, at least 70%, at least 80%, at least 90%, or more as compared to an appropriate control.

In one embodiment of any aspect, assaying is done by immunofluorescence or flow cytometry.

In one embodiment of any aspect, the subject has previously been administered an anti-cancer therapy.

In one embodiment of any aspect, the subject has not previously been administered an anti-cancer therapy.

Another aspect described herein provides a method of identifying a subject as having asparaginase-resistant cancer comprising (a) obtaining a biological sample from a subject having cancer; (b) assaying the sample to identify for GSK3α-positive puncta; and (c) identifying a subject as having asparaginase-resistant cancer if the cancer has GSK3α-positive puncta.

Another aspect described herein provides a method of identifying a subject as having asparaginase-resistant cancer comprising (a) receiving the results of an assay that identifies a subject as having a cancer forming GSK3α-positive puncta; and (b) identifying a subject as having asparaginase-resistant cancer if the cancer forms GSK3α-positive puncta.

Another aspect described herein provides a method of treating cancer comprising (a) obtaining a biological tumor sample from a subject having cancer; (b) assaying the sample by treating with an asparaginase, or culturing in conditions of asparagine starvation or amino acid starvation; (c) identifying the sample as forming GSK3α-positive puncta in response to asparagine starvation; and (d) administering an asparaginase and an agent that inhibits GSK3α to a subject who has been identified as having a sample that forms GSK3α-positive puncta.

Another aspect described herein provides a method of treating cancer comprising (a) receiving the results of an assay that identifies a subject as having a cancer that forms GSK3α-positive puncta in response to asparaginase treatment or asparagine starvation; and (b) administering an asparaginase and an agent that inhibits GSK3α to a subject who has been identified as having a cancer that forms GSK3α-positive puncta in response to asparagine starvation.

Another aspect described herein provides a method of treating asparaginase-resistant cancer comprising (a) obtaining a biological sample from a subject having cancer; (b) assaying the sample to identify formation of GSK3α-positive puncta in response to asparaginase treatment or asparagine starvation; (c) identifying a subject as having asparaginase-resistant cancer if the cancer forms GSK3α-positive puncta in response to asparagine starvation; and (d) administering an asparaginase and an agent that inhibits GSK3α to a subject who has been identified as having asparaginase-resistant cancer.

Another aspect described herein provides a method of treating asparaginase-resistant cancer comprising (a) receiving the results of an assay that identifies a subject as having a cancer that forms GSK3α-positive puncta in response to asparaginase treatment or asparagine starvation; (b) administering an asparaginase and an agent that inhibits GSK3α to a subject who has been identified as having asparaginase-resistant cancer.

Another aspect described herein provides a method of identifying a subject as having asparaginase-resistant cancer comprising (a) obtaining a biological sample from a subject having cancer; (b) treating the sample with asparaginase, or asparagine starvation, or amino acid starvation; (c) assaying the sample to identify formation of GSK3α-positive puncta; and (d) identifying a subject as having asparaginase-resistant cancer if the sample forms GSK3α-positive puncta.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

As used herein, the terms "treat," "treatment," "treating," or "amelioration" refer to therapeutic treatments, wherein the object is to reverse, alleviate, ameliorate, inhibit, slow down or stop the progression or severity of a condition associated with cancer, e.g., leukemia, colon cancer, or pancreatic cancer. The term "treating" includes reducing or alleviating at least one adverse effect or symptom of cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a in disease also includes providing relief from the symptoms or side-effects of the disease (including palliative treatment).

As used herein, the term "administering," refers to the placement of a therapeutic (e.g., an agent that inhibits GSK3α and/or asparaginase) or pharmaceutical composition as disclosed herein into a subject by a method or route which results in at least partial delivery of the agent to the subject. Pharmaceutical compositions comprising agents as disclosed herein can be administered by any appropriate route which results in an effective treatment in the subject.

As used herein, a "subject" means a human or animal. Usually the animal is a vertebrate such as a primate, rodent, domestic animal or game animal. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., cancer. A subject can be male or female.

A subject can be one who has been previously diagnosed with or identified as suffering from or having a disease or disorder in need of treatment (e.g., cancer) or one or more complications related to such a disease or disorder, and optionally, have already undergone treatment (e.g., one or more cancer therapies) for the disease or disorder or the one or more complications related to the disease or disorder. Alternatively, a subject can also be one who has not been previously diagnosed as having such disease or disorder or related complications. For example, a subject can be one who exhibits one or more risk factors for the disease or disorder or one or more complications related to the disease or disorder or a subject who does not exhibit risk factors.

As used herein, an "agent" refers to e.g., a molecule, protein, peptide, antibody, or nucleic acid, that inhibits expression of a polypeptide or polynucleotide, or binds to, partially or totally blocks stimulation, decreases, prevents, delays activation, inactivates, desensitizes, or down regulates the activity of the polypeptide or the polynucleotide. Agents that inhibit GSK3α, e.g., inhibit expression, e.g., translation, post-translational processing, stability, degradation, or nuclear or cytoplasmic localization of a polypeptide, or transcription, post transcriptional processing, stability or degradation of a polynucleotide or bind to, partially or totally block stimulation, DNA binding, transcription factor activity or enzymatic activity, decrease, prevent, delay activation, inactivate, desensitize, or down regulate the activity of a polypeptide or polynucleotide. An agent can act directly or indirectly.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion and other variants.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "RNAi" as used herein refers to interfering RNA or RNA interference. RNAi refers to a means of selective post-transcriptional gene silencing by destruction of specific mRNA by molecules that bind and inhibit the processing of mRNA, for example inhibit mRNA translation or result in mRNA degradation. As used herein, the term "RNAi" refers to any type of interfering RNA, including but are not limited to, siRNA, shRNA, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein).

As used herein, the term "cancer therapy" or "cancer treatment" refers to a therapy useful in treating a cancer. Examples of anti-cancer therapeutic agents include, but are not limited to, e.g., surgery, chemotherapeutic agents, immunotherapy, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also contemplated for use with the methods described herein.

Methods and compositions described herein require that the levels and/or activity of GSK3α are inhibited. As used herein, "Glycogen synthase kinase-3 alpha (GSK3α)" refers to a multifunctional Ser/Thr protein kinase that is implicated in the control of several regulatory proteins including glycogen synthase, and transcription factors, such as JUN. It also plays a role in the WNT and PI3K signaling pathways, as well as regulates the production of beta-amyloid peptides associated with Alzheimer's disease. GSK3α sequences are known for a number of species, e.g., human GSK3α (NCBI Gene ID: 2931) polypeptide (e.g., NCBI Ref Seq NP_063937.2) and mRNA (e.g., NCBI Ref Seq NM_019884.2). GSK3α can refer to human GSK3α, including naturally occurring variants, molecules, and alleles thereof. GSK3α refers to the mammalian GSK3α of, e.g., mouse, rat, rabbit, dog, cat, cow, horse, pig, and the like. The nucleic sequence of SEQ ID NO: 1 comprises the nucleic sequence which encodes GSK3α.

SEQ ID NO: 1 is a nucleic acid sequence that encodes GSK3α.

```
                                            (SEQ ID NO: 1)
ctcggcgcca tgagcggcgg cgggccttcg ggaggcggcc
ctgggggctc gggcagggcg cggactagct cgttcgcgga
gcccggcggc ggaggcggag gaggcggcgg cggcccccgga
ggctcggcct ccggcccagg cggcaccggc ggcggaaagg
catctgtcgg ggccatgggt gggggcgtcg gggcctcgag
ctccgggggt ggacccggcg gcagcggcgg aggaggcagc
ggaggccccg gcgcaggcac tagcttcccg ccgcccgggg
tgaagctggg ccgtgacagc gggaaggtga ccacagtcgt
agccactcta ggccaaggcc cagagcgctc ccaagaagtg
gcttacacgg acatcaaagt gattggcaat ggctcatttg
gggtcgtgta ccaggcacgg ctggcagaga ccagggaact
agtcgccatc aagaaggttc tccaggacaa gaggttcaag
aaccgagagc tgcagatcat gcgtaagctg gaccactgca
atattgtgag gctgagatac tttttctact ccagtggcga
gaagaaagac gagctttacc taaatctggt gctggaatat
gtgcccgaga cagtgtaccg ggtggcccgc cacttcacca
aggccaagtt gaccatccct atcctctatg tcaaggtgta
catgtaccag ctcttccgca gcttggccta catccactcc
cagggcgtgt gtcaccgcga catcaagccc cagaacctgc
tggtggaccc tgacactgct gtcctcaagc tctgcgattt
tggcagtgca aagcagttgg tccgaggggga gcccaatgtc
tcctacatct gttctcgcta ctaccgggcc ccagagctca
tctttggagc cactgattac acctcatcca tcgatgtttg
gtcagctggc tgtgtactgg cagagctcct cttgggccag
cccatcttcc ctggggacag tggggtggac cagctggtgg
agatcatcaa ggtgctggga acaccaaccc gggaacaaat
ccgagagatg aaccccaact acacggagtt caagttccct
cagattaaag ctcacccctg gacaaaggtg ttcaaatctc
gaacgccgcc agaggccatc gcgctctgct ctagcctgct
ggagtacacc ccatcctcaa ggctctcccc actagaggcc
tgtgcgcaca gcttctttga tgaactgcga tgtctgggaa
```

-continued

```
cccagctgcc taacaaccgc ccacttcccc ctctcttcaa
cttcagtgct ggtgaactct ccatccaacc gtctctcaac
gccattctca tccctcctca cttgaggtcc ccagcgggca
ctaccaccct caccccgtcc tcacaagctt taactgagac
tccgaccagc tcagactggc agtcgaccga tgccacacct
accctcacta actcctcctga
```

The term "decrease", "reduced", "reduction", or "inhibit" are all used herein to mean a decrease by a statistically significant amount. In some embodiments, "decrease", "reduced", "reduction", or "inhibit" typically means a decrease by at least 10% as compared to an appropriate control (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to an appropriate control.

As used herein, a "reference level" refers to a normal, otherwise unaffected cell population or tissue (e.g., a biological sample obtained from a healthy subject, or a biological sample obtained from the subject at a prior time point, e.g., a biological sample obtained from a patient prior to being diagnosed with cancer, or a biological sample that has not been contacted with an agent disclosed herein).

As used herein, an "appropriate control" refers to an untreated, otherwise identical cell or population (e.g., a subject who was not administered an agent described herein, or was administered by only a subset of agents described herein, as compared to a non-control cell).

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment. The term "consisting of" refers to compositions, methods, and respective components thereof as described herein, which are exclusive of any element not recited in that description of the embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

FIG. 1 shows GSK3α body formation predicts resistance to asparaginase. Primary patient samples of the indicated types (T-ALL, T-cell acute lymphoblastic leukemia; B-ALL, B-cell acute lymphoblastic leukemia; AML, acute myeloid leukemia) were expanded in immunodeficient mice, and viably frozen. Samples were then thawed and treated with asparaginase (100 U/L) for 48 hours in cell culture conditions, and GSK3α body formation was assessed by confocal immunofluorescence microscopy. Asparaginase response was assessed after 48 hours by trypan blue viable cell counts. PDXs with a viability ≤60% were considered as sensitive to asparaginase treatment. ****, $p<0.0001$.

FIG. 2 depicts a model for synthetic lethal interaction of Wnt pathway activation and asparaginase. Asparaginase induces leukemic cell death by depleting asparagine. Drug-resistant leukemias rely on protein degradation as a catabolic source of asparagine to survive asparaginase treatment. This is mediated by GSK3, which can phosphorylate a large number of cellular proteins, to form a phospho-degron that marks proteins for ubiquitination and proteasomal degradation. This adaptive response is blocked by activation of Wnt signaling (the so-called Wnt-dependent stabilization of proteins, Wnt/STOP), or by selective inhibition of GSK3α.

FIGS. 3A-3C show asparaginase resistance is uniquely dependent on the N-terminal low complexity domain of GSK3α. (FIG. 3A) Protein domains of GSK3α and GSK3β. The kinase and axin-binding domains are 97% similar and are predicted to be structured (black), but the low-complexity (disordered) domains (green) are not conserved. Domain prediction based on (Huang et al., 2014). (FIG. 3B) Jurkat T-ALL cells were transduced with control or GSK3α-targeting shRNAs, and relative viability in 1000 U/L asparaginase was assessed. The toxicity of shGSK3α was then rescued by transducing wild-type GSK3α, but not GSK3β. We then expressed various domain-swapped alleles in which the N-terminal, kinase, and C-terminal domains of GSK3α and β were swapped in various configurations. Note that the N-terminus of GSK3a is required for asparaginase resistance, because GSK3β is unable to rescue asparaginase sensitivity unless its N-terminus is replaced by that of GSK3α. Conversely, a GSK3a allele in which its N-terminus is swapped with that of GSK3b is completely unable to restore asparaginase resistance. The kinase and C-terminal domains of GSK3a and GSK3b are completely interchangeable (data not shown). (FIG. 3C) Alignment of the amino acids of GSK3a and GSK3b. Note the glycine and serine-rich low-complexity domain of GSK3α. FIG. 3C discloses SEQ ID NOS 5 and 6, respectively, in order of appearance.

FIGS. 4A-4D show asparagine starvation induces phase separation of GSK3α into cytoplasmic bodies (or puncta), but not GSK3b. (FIG. 4A) Confocal immunofluorescence microscopy for GSK3α or the nuclear marker DAPI, in Jurkat cells treated with vehicle or asparaginase (100 U/L) for 48 hours. (FIG. 4B) Confocal immunofluorescence microscopy for GSK3β or the nuclear marker DAPI, in Jurkat cells treated with vehicle or asparaginase (100 U/L) for 48 hours. (FIG. 4C) Number of puncta per 50 cells. (FIG. 4D) Formation of GSK3α bodies is selective to asparaginase, and is not induced by other cellular stressors such as other chemotherapeutics or heat shock. ****, $p<0.0001$. ns (not significant), $p>0.05$.

FIG. 5 shows asparaginase-induced GSK3α bodies are membraneless, as assessed by proteinase protection assay. Jurkat cells were treated with vehicle, asparaginase (×48 hrs) to induce formation of GSK3α bodies, or Wnt3A to induce GSK3 sequestration in membrane-bound multivesicular bodies (Taelman et al., 2010). Cells were permeabilized, and treated with vehicle or proteinase K to digest free cytoplasmic proteins. Triton is a control that dissolves all membranes.

FIGS. 6A and 6B show GSK3α bodies function in the protein ubiquitination-proteasomal degradation pathway in response to asparagine starvation. (FIG. 6A) Jurkat T-ALL cells were treated with vehicle, asparaginase, the GSK3α inhibitor BRD0705, or the combination of asparaginase and BRD0705 (combo). Immunofluorescence microscopy was then performed for GSK3α, K48-linked ubiquitin chains (which mark proteins for proteasomal degradation), or the nuclear marker DAPI. Note that GSK3a can still undergo translocation into GSK3a bodies even if its enzymatic activity is inhibited, but the ability of GSK3a bodies to ubiquitinate proteins is completely dependent on the enzymatic activity of GSK3α. (FIG. 6B) Quantification of the immunofluorescence in 50 cells from each condition. Coloc refers to co-localization of both GSK3α and ubiquitin (ub), as determined by yellow color on the merged confocal image. ****, $p<0.0001$. ns (not significant), $p>0.05$.

FIGS. 7A-7D show GSK3α Body Formation Predicts Sensitivity to the Combination of GSK3α Inhibition and Asparaginase (combo treatment). (FIG. 7A) The indicated leukemia cell lines were treated with 100 U/L asparaginase in the presence of 1 μM GSK3α inhibitor and BRD0705 (combo treatment), and viability was assessed after 5 days of treatment by trypan blue viable cell counts. Counts were normalized to untreated controls. Cell lines with a viability ≤60% were considered sensitive to combo treatment. (FIG. 7B) The cell lines in (FIG. 7A) were treated as in (FIG. 7A). After 5 days, cells were harvested, fixed, and permeabilized, and subsequently stained for GSK3α (Cell Signaling #4818S). DAPI was used as a nuclear stain and Alexa Fluor 555 as a secondary antibody for GSK3α detection. Images were taken on a Zeiss LSM 710 confocal microscope. Cytoplasmic GSK3α bodies were counted manually in a total of 50 cells, and images were analyzed with ImageJ. Statistical significance was assessed by a two-sided t-test with Welch's correction. All experiments were performed in biologic duplicates. (FIG. 7C) T-ALL, B-ALL and AML patient-derived xenogratfs (PDXs) were treated as described in (FIG. 7A). Viability was assessed after 5 days of treatment using trypan blue exclusion dye. Counts were normalized to no asparaginase, no BRD0705 cells. (FIG. 7D) PDXs were treated as in (FIG. 7A) and analyzed as described in (FIG. 7B). ***, $p<0.001$.

FIG. 8 shows that asparagine depletion (e.g., starvation) triggers formation of GSK3α puncta. Addition of asparagine (L-Asn) in an asparagine depleted cell inhibits the formation of GSK3α puncta, whereas the addition of glutamine (L-Glut) does not, indicating that the puncta formation is in response to the lack of asparagine.

FIGS. 9A-9F show formation of GSK3α bodies predict asparaginase resistance, and sensitivity to asparaginasc in combination with a GSK3α inhibitor, in human cancers. (FIG. 9A) A panel of human leukemia cell lines were treated with vehicle or a 100 U/L dose of asparaginase for 48 hours, and GSK3α body formation was assessed using immunofluorescence for GSK3α. Cells are classified as asparaginase-sensitive or resistance based effects of this dose of asparaginasc on viability, as assessed by counting trypan blue viable cells. For GSK3α body quantification, GSK3α positive puncta were counted in 50 cells in biologic triplicates. Statistical significance was assessed by a two-sided Student's t-test with Welch adjustment. **$p\leq0.0001$. (FIG. 9B) Human leukemia cell lines from (FIG. 9A) were treated with vehicle or combo (asparaginase 100 U/L in combination with the GSK3α inhibitor BRD0705 1 μM). Cells were classified as resistant or sensitive to combo treatment by counting trypan blue viable cells. GSK3α body formation and statistical significance were assessed as described in (FIG. 9A). p≤0.0001. (FIG. 9C) Human leukemia specimens from children with acute leukemia, which were expanded in immunodeficient mice as patient-derived xenografts (PDXs), were treated with 100 U/L asparaginase for 48 hours. Response assessment and GSK3α body quantification were performed as described in (FIG. 9A). Statistical significance was assessed by a two-sided Student's t-test with Welch adjustment. p≤0.0001. (FIG. 9D) Human leukemia PDXs from (FIG. 9C) were treated as described in (FIG. 9B). Statistical significance was assessed by a two-sided Student's t-test with Welch adjustment. *p≤0.001. (FIG. 9E) Receiver operating characteristic (ROC) analysis of human leukemia cell lines and PDXs from the experiments shown in (FIG. 9A) and (FIG. 9C). (FIG. 9F) ROC analysis human leukemia cell lines and PDXs from the experiments shown in (FIG. 9B) and (FIG. 9D).

Figure 19:
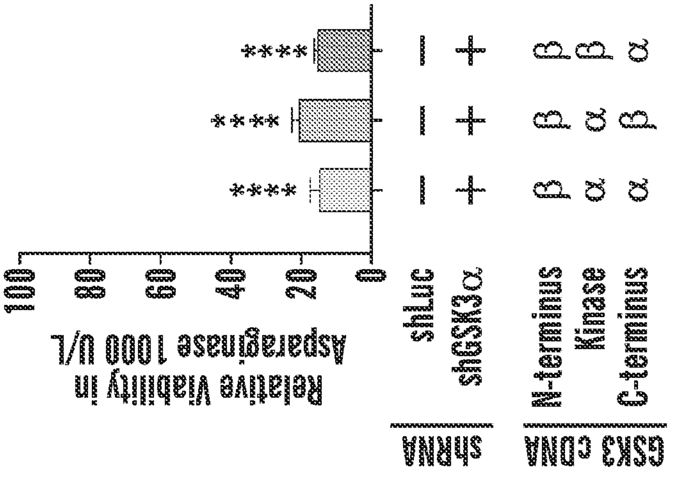

FIG. 19 shows tolerance of asparagine starvation is uniquely dependent on an N-terminal low-complexity domain of GSK3α. Jurkat T-ALL cells were transduced with the indicated constructs, treated with 100 U/L asparaginase for 5 days, and relative viability was assessed. Unless otherwise indicated, all significance assessments reflect comparisons to the shLuc control.

Figure 20A:
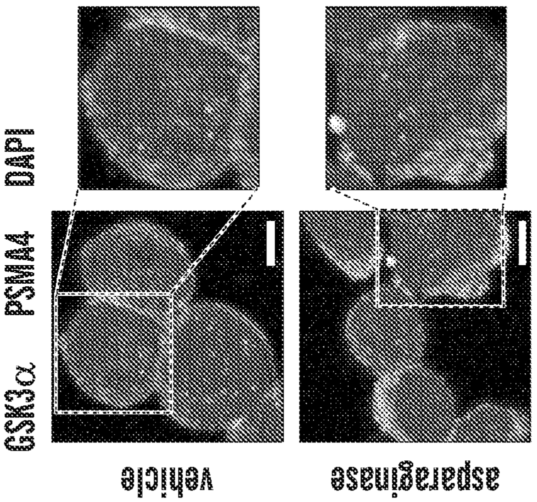
Figure 20B:
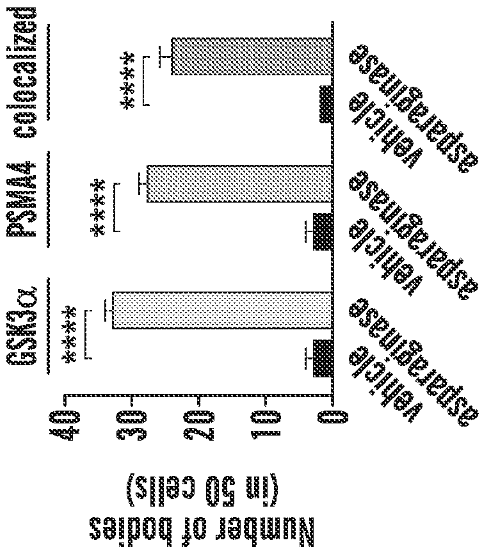

FIGS. 20A and 20B show asparagine depletion triggers spatial sequestration of GSK3α with the ubiquitin proteasome system. (FIG. 20A) Jurkat cells were treated with vehicle or asparaginase for 48 hours, and localization of GSK3α and the proteasomal subunit PSMA4 was assessed by confocal immunofluorescence microscopy. (FIG. 20B) Quantification of bodies positive for GSK3α, PSMA4, or both markers colocalized. Scale bars, 5 μM. ****p≤0.0001. n.s., p>0.05.

Figure 21A:
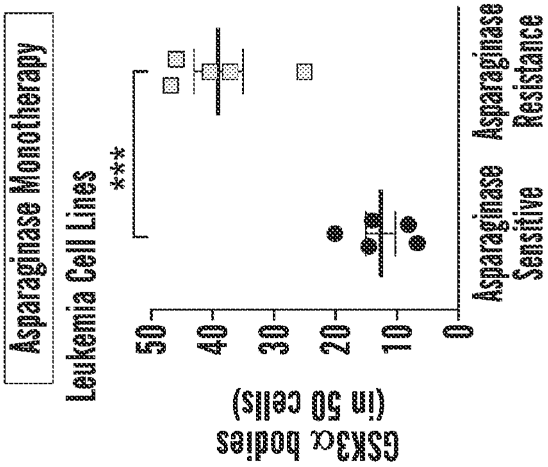

FIGS. 21A-21E show GSK3α body formation predicts asparaginase response in human leukemia. (FIG. 21A) Leukemia cell lines were treated with vehicle or 100 U/L asparaginase for 48 hours, and GSK3α body formation was assessed by confocal immunofluorescence microscopy. Cells were classified as asparaginase-sensitive vs. resistant. Data points represent the average of biologic duplicates. (FIG. 21B) Patient-derived xenograft (PDX) leukemia specimens were treated with asparaginase, classified as asparaginase-sensitive or resistant, and GSK3α body formation was assessed. Each data point represents the average of biologic duplicates. (FIG. 21C) Assessment of GSK3α body formation after treatment with 100 U/L asparaginase for 48 hrs, assessed by confocal immunofluorescence microscopy as in (FIG. 21A), in PDX models collected at initial diagnosis from patients who had an excellent response to asparaginasc-intensive combination chemotherapy, versus those collected at relapse. (FIG. 21D) Human leukemia cell lines were treated with vehicle or combo (asparaginase 100 U/L in combination with the GSK3α inhibitor BRD0705, 1 μM), and GSK3α body formation was assessed as in (FIG. 21A). Cell lines were classified as combo sensitive or resistant based on the viability data. Each data point represents the average of biologic duplicates. *p≤0.001. (FIG. 21E) Human leukemia PDX samples were treated as in (FIG. 21B), and classified as combo-sensitive versus resistant based on the viability data. Each data point represents the average of biologic duplicates. *p≤0.001; **p≤0.01.

FIGS. 22A-22D show evolutionary conservation of mammalian GSK3α orthologs. ClustalW alignment of mammalian GSK3α proteins from the indicated species. The uniprot identifiers of each protein are indicated on the figure. Domains were annotated based on the kinase domain boundaries, as annotated on the human protein (e.g., available on the world wide web at uniprot.org, accessed Aug. 2, 2020).

Figure 23B:
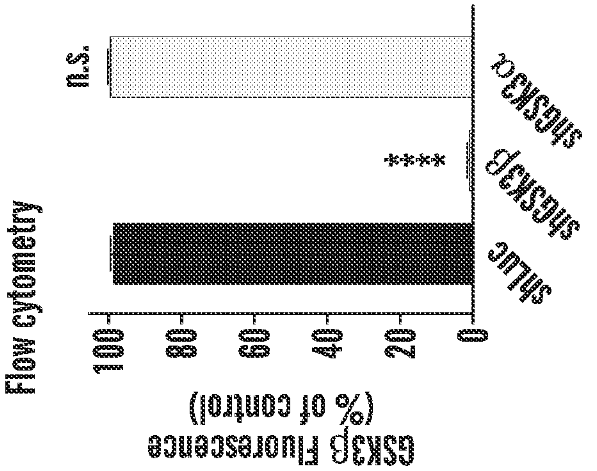
Figure 23A:
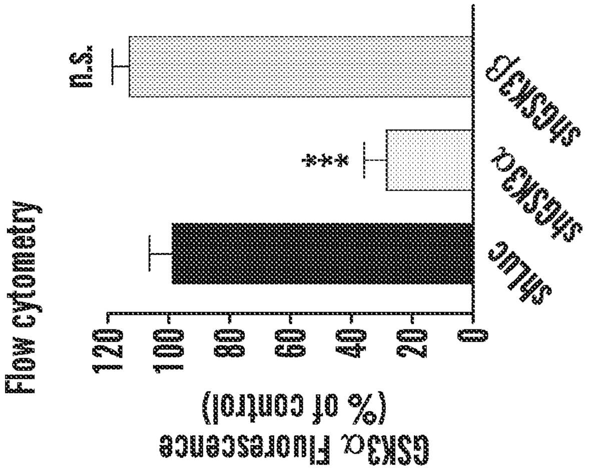
Figure 24A:
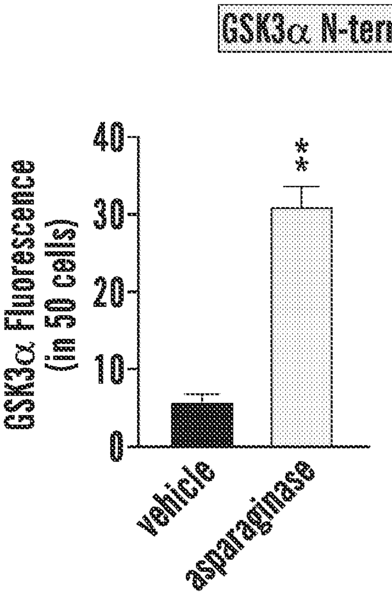
Figure 24B:
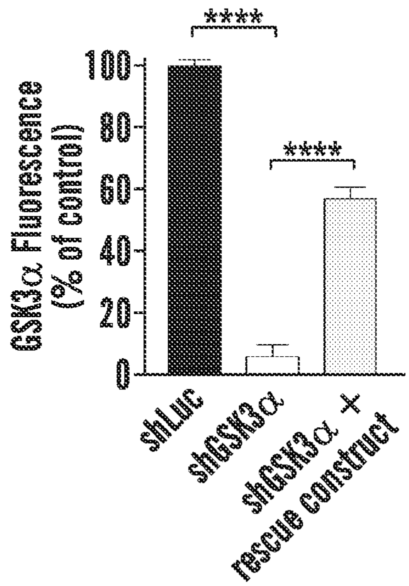
Figure 24C:
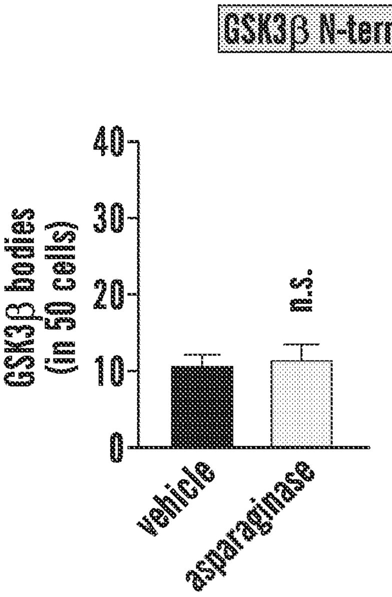
Figure 24D:
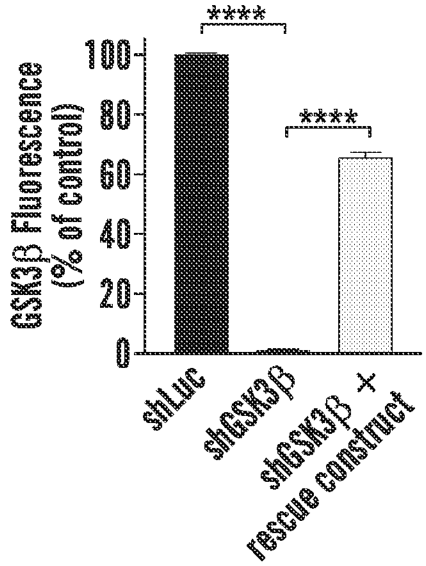

FIGS. 23A and 23B show paralog specificity of GSK3α and GSK3β antibodies. (23A and 23B) Jurkat T-ALL cells were transduced with shRNAs targeting GSK3α, GSK3β, or shLuciferase (shLuc) negative control. After puromycin selection, cells were fixed, permeabilized, and stained with anti-GSK3α (23A) or anti-GSK3β (23B) antibodies. Mean fluorescence intensity was assessed by flow cytometry (23A-23B), and is shown as percent of shLuc control.

FIGS. 24A-24D show N-terminus of GSK3α is sufficient to trigger spatial sequestration of GSK3β in response to asparaginase. (FIG. 24A) The number of GSK3 bodies was counted in 50 cells in biological triplicates. (FIG. 24B) To confirm specificity of the antibody for the transduced GSK3 allele, Jurkat cells were transduced with shRNAs targeting luciferase (shLuc, negative control) or endogenous GSK3α, alone or together with the GSK3 fusion construct. Cells were fixed and stained with the GSK3α antibody, and fluorescence intensity was assessed by flow cytometry, which is shown as % of shLuc control. (FIG. 24C) The number of GSK3 bodies was counted in 50 cells in biological triplicates. (FIG. 24D) To confirm specificity of the antibody for the transduced GSK3 allele in the experiments in D-E, Jurkat cells were transduced with the indicated constructs. Note that the rescue construct was the GSK3 fusion construct. Cells were then fixed and stained with the GSK3β antibody, and fluorescence intensity was assessed by flow cytometry, and is shown as percent of shLuciferase (shLuc) control. All error bars represent SEM. Scale bars, 5 μm. **p≤0.0001, p≤0.01, n.s. p>0.05.

Figure 25:
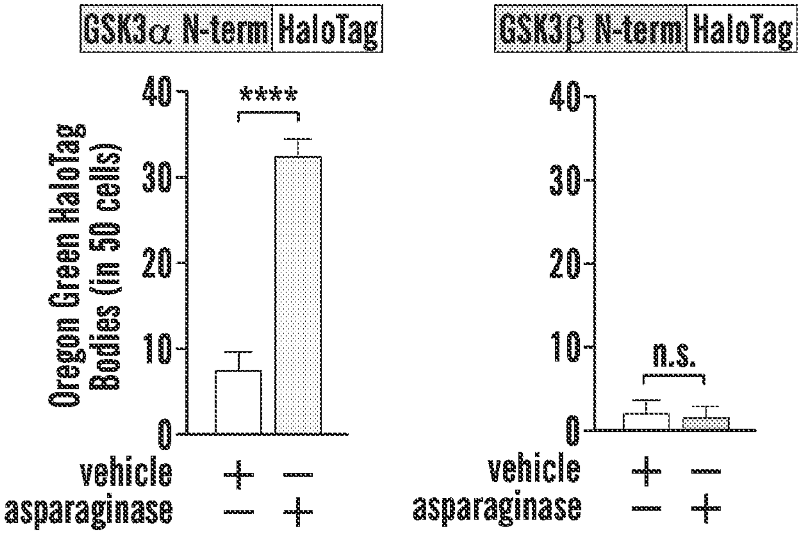
Figure 26A:
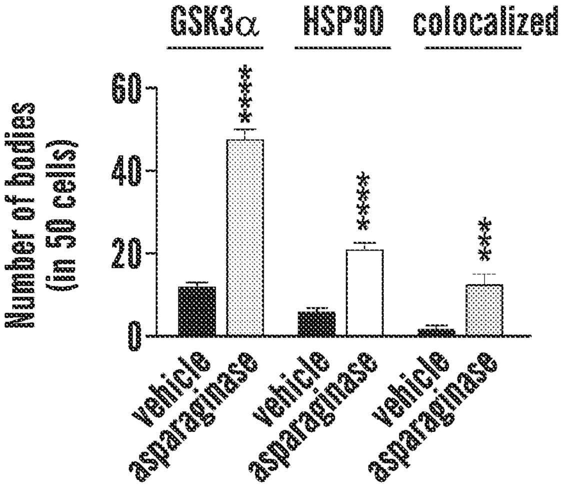
Figure 26B:
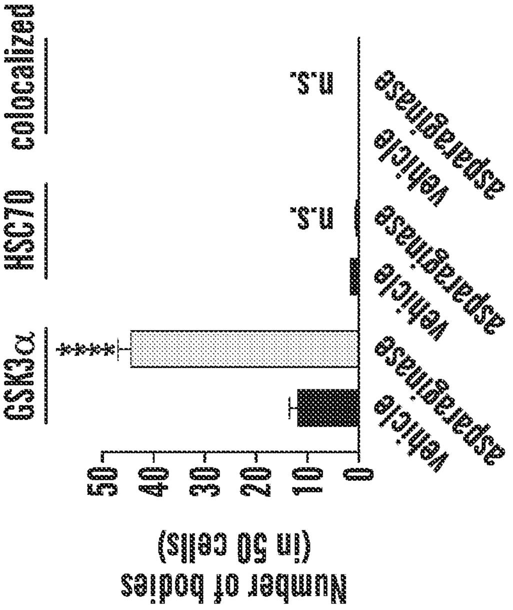
Figure 26C:
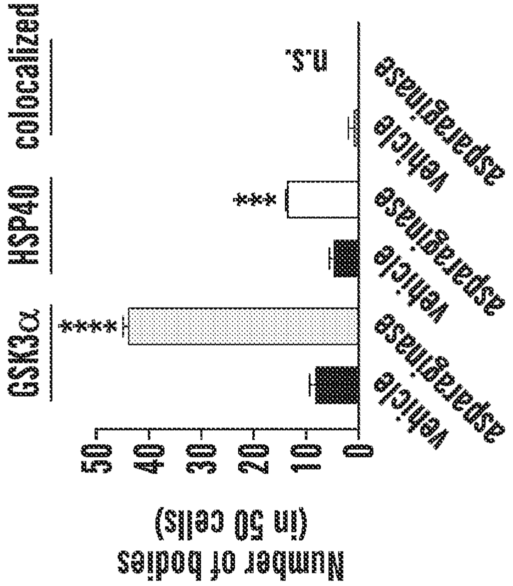
Figure 26E:
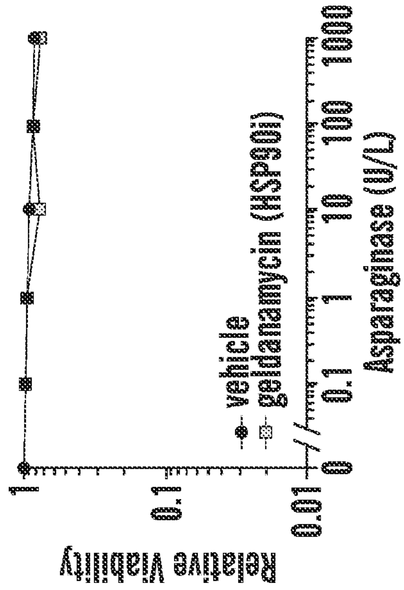
Figure 26D:
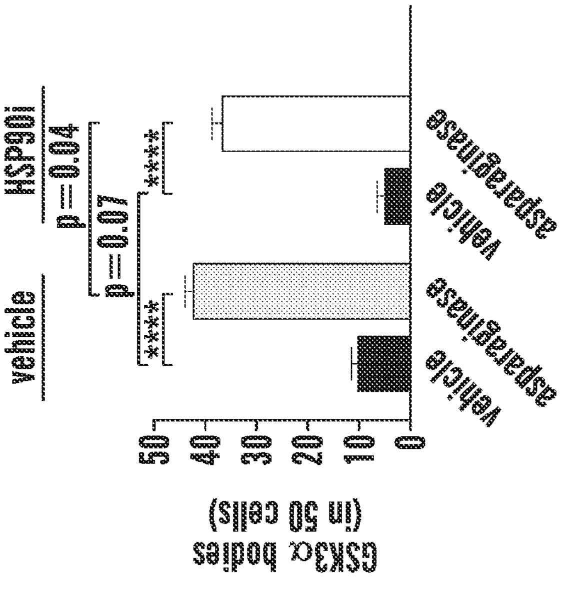

FIG. 25 shows the N-terminus of GSK3α is sufficient to trigger biomolecular condensation of a heterologous protein in response to asparaginase. Jurkat cells were transduced with expression constructs encoding the N-terminus of either GSK3α (amino acids 1-118) or GSK3β (amino acids 1-55) fused to Halo Tag. Cells were treated with 100 U/L asparaginase for 48 hrs, and stained with the fluorescent ligand Oregon Green to detect HaloTag positive bodies. Confocal microscopy was the performed, and the number of HaloTag positive bodies was counted in 50 cells in biological triplicates. Statistical significance was assessed by a two-sided Student's t-test with Welch adjustment. All error bars represent SEM. ****p≤0.0001. n.s., p>0.05.

FIGS. 26A-26E show assessment of colocalization of heat shock proteins HSP90, HCSC70 and HSP40 with GSK3α bodies in response to asparaginase. (FIG. 26A) Jurkat cells were treated with vehicle or asparaginase (100 U/L) for 48 hours, fixed, permeabilized, and stained using anti-GSK3α and anti-HSP90 antibodies. The number of puncta positive for GSK3α, HSP90, or both markers colocalized was counted in 50 cells in biologic triplicate per condition. (FIG. 26B) Jurkat cells were treated with vehicle or asparaginase (100 U/L) for 48 hrs, stained for GSK3α and HSC70, and localization was assessed. (FIG. 26C) Jurkat cells were treated with vehicle or asparaginase (100 U/L) for 48 hrs, stained for GSK3α and HSP40, and localization was assessed. (FIG. 26D) Jurkat cells were treated with vehicle or the HSP90 inhibitor geldanamycin (500 nM), together with vehicle or asparaginase (100 U/L). GSK3α body formation was assessed. (FIG. 26E) Jurkat cells were treated with vehicle or the HSP90 inhibitor geldanamycin (500 nM), together with the indicated dose of asparaginase for 48 hrs. Viability was assessed by counting the number of live cells based on trypan blue vital dye exclusion. All cell counts were normalized those in vehicle-treated, no-asparaginase controls. Error bars represent SEM. Scale bars, 5 μm or 2 μm (inset). *p≤0.001. , p≤0.01. *, p≤0.05. n.s., p>0.05.

Figure 27C:
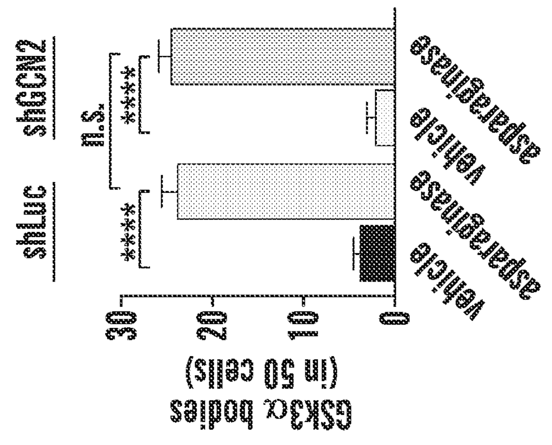
Figure 27B:
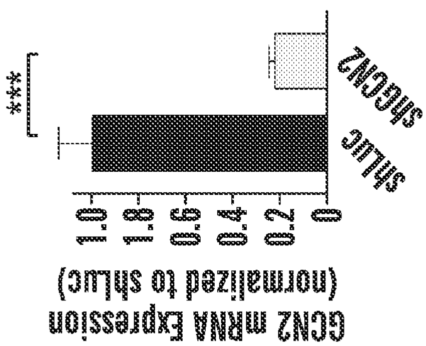
Figure 27A:
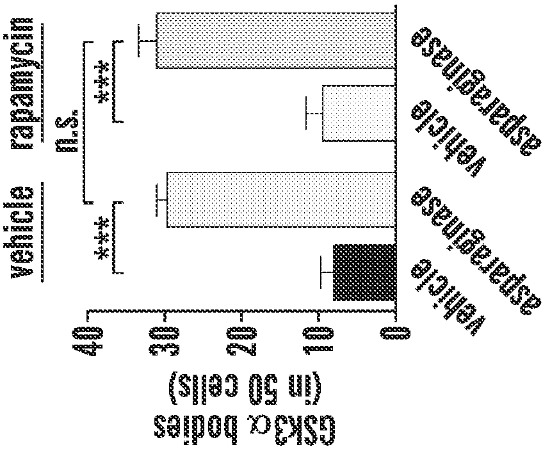
Figure 28A:
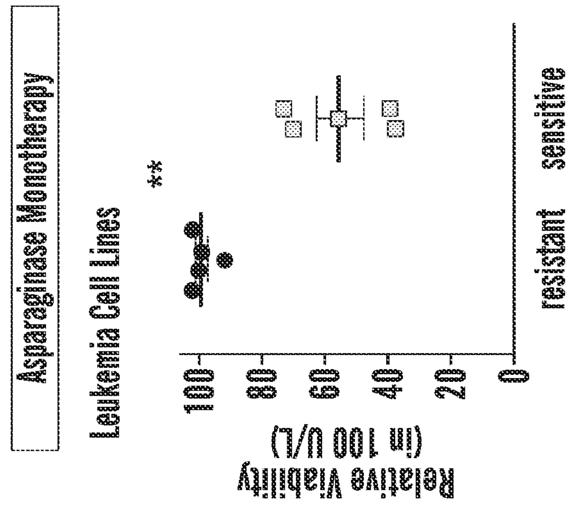
Figure 28B:
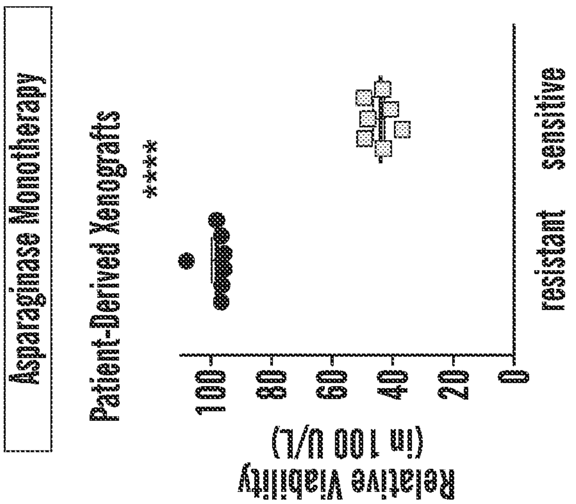
Figure 28D:
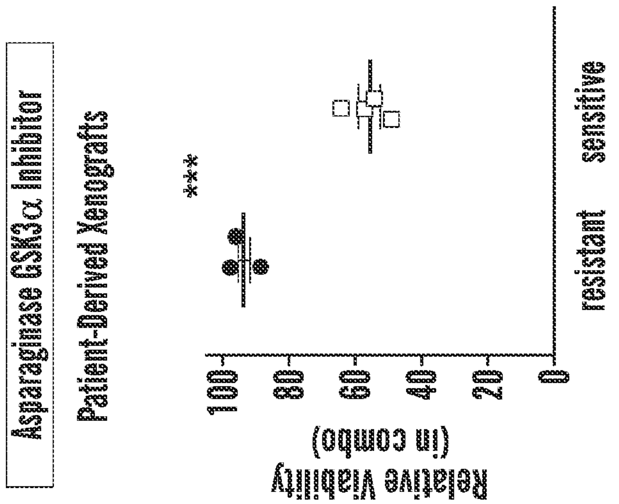
Figure 28C:
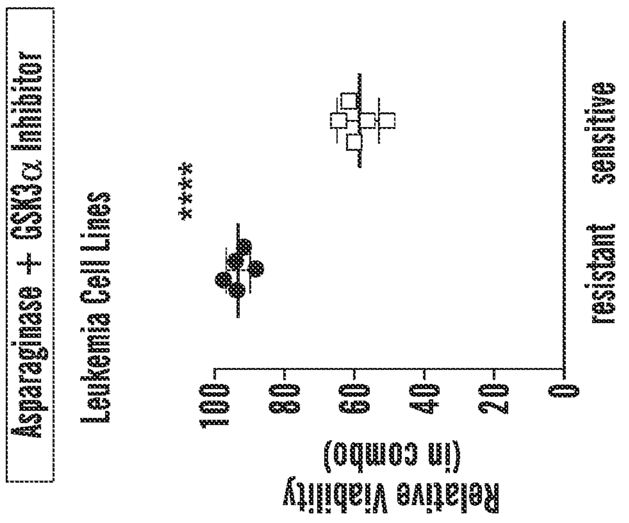

FIGS. 27A-27C show lack of effect of mTORC1 or GCN2 inhibitors on GSK3α body formation. (FIG. 27A) Jurkat cells were treated with vehicle or rapamycin (10 nM), together with cither vehicle or asparaginase (100 U/L) for 48 hrs. Subsequently, cells were fixed and GSK3α colocalization was assessed by confocal immunofluorescence microscopy. The number of GSK3α bodies was counted in 50 cells in biological triplicates. (FIG. 27B) Jurkat cells were transduced with an shRNA targeting GCN2 or an shLuciferase control, and relative mRNA expression was assessed by qRT-PCR. (FIG. 27C) Jurkat cells transduced with shLuciferase or shGCN2 were treated with vehicle or asparaginase (100 U/L) for 48 hrs, and GSK3α localization was assessed by confocal immunofluorescence microscopy.

FIGS. 28A-28D show classification of human leukemia cell lines and patient-derived xenografts (PDX) as sensitive versus resistant to monotherapy with asparaginase, or to the combination of asparaginase and the GSK3α inhibitor BRD0705. (FIG. 28A-28B) The panel of human leukemia cell lines (FIG. 28A) or PDX models (FIG. 28B) shown in Table S1 were treated with asparaginase (100 U/L) or vehicle control for 48 hrs, and viability was assessed by trypan blue vital dye exclusion. The relative viability of each case is shown versus its vehicle-treated control. Cells were classified as resistant or sensitive to asparaginase monotherapy based on results of this analysis. (FIG. 28C-28D) Asparaginase-resistant cases from (FIG. 28A-28B) were treated with asparaginase (100 U/L) in combination with the GSK3α inhibitor BRD0705 (1 μM) for 48 hrs. Relative viability was assessed as in (FIGS. 28C-28D), and was used to classify these cases as resistant or sensitive to this combination. Each datapoint represents the average of biologic duplicates. Error bars represent SEM. **p≤0.0001, *p≤0.001, **p≤0.01.

DETAILED DESCRIPTION

Tolerance of amino acid starvation is fundamental to robust cellular fitness. Asparagine depletion is lethal to some cancer cells, a vulnerability exploited clinically using asparaginase. Data presented herein show that resistance to asparagine starvation is uniquely dependent on an N-terminal low-complexity domain of GSK3α lacking in its paralog GSK3β. Upon depletion of specific amino acids, including asparagine, leucine or valine, this domain mediates spatial sequestration of GSK3α into membraneless cytoplasmic bodies together with the ubiquitin proteasome system, a catabolic amino acid source. In normal cells, GSK3α promotes survival during essential amino acid starvation. In human leukemia, GSK3α body formation predicts asparaginase resistance, and sensitivity to the combination of asparaginase and a small molecule GSK3α inhibitor. Our data indicate that GSK3α body formation provides a cellular mechanism to maximize the catalytic efficiency of proteasomal protein degradation during amino acid starvation, an adaptive response co-opted by cancer cells for asparaginase resistance.

Methods of Treating Cancer

The invention described herein is related, in part, to the discovery that treatment with a GSK3α inhibitor induces profound sensitization to asparaginase in acute leukemias and colorectal cancers that are refractory to monotherapy with asparaginase. This is because GSK3α function mediates asparaginase resistance in these cells by stimulating protein degradation. Protein degradation leads to the release of free amino acids, which replenish the pool of asparagine in cancer cells and allow these to survive during therapy with asparaginase. The current invention described herein involves the discovery that GSK3α undergoes physical re-localization upon treatment with asparaginase, from its diffuse cytoplasmic localization at baseline into GSK3α-positive puncta in the cytoplasm of these cells. Formation of these puncta reflects the fact that cells are activating GSK3α-dependent protein degradation by concentrating GSK3α together with other key components of the cellular machinery for protein ubiquitination and proteasomal degradation, in order to maximize efficiency of this biochemical reaction in response to asparagine starvation. Activation of GSK3α dependent protein degradation in response to asparaginase treatment or asparagine starvation can be measured using immunofluorescence confocal microscopy, which reveals the markedly altered localization of GSK3α from its diffuse cytoplasmic localization at baseline into these cytoplasmic puncta (or inclusions), which were termed GSK3α bodies. The inventors have now shown that formation of these GSK3α bodies correlates with resistance to asparaginase monotherapy, and predicts response to the combination of GSK3α inhibition and asparaginase. This is a one of a kind diagnostic method; there are no other means to identify patients who will respond to the combination of GSK3α inhibition and asparaginase.

Accordingly, one aspect described herein is a method of treating cancer comprising (a) obtaining a biological sample from a subject having cancer; (b) assaying the sample and identifying the cancer as forming GSK3α-positive puncta; and (c) administering an asparaginase and an agent that inhibits GSK3α to a subject who has been identified as forming GSK3α-positive puncta.

Another aspect described herein is a method of treating cancer comprising (a) receiving the results of an assay that identifies a subject as having a cancer forming GSK3α-positive puncta; and (b) administering an asparaginase and an agent that inhibits GSK3α to a subject who has been identified as forming GSK3α-positive puncta.

Another aspect described herein is a method of treating asparaginase-resistant cancer comprising: (a) obtaining a biological sample from a subject having cancer; (b) assaying the sample to identify for GSK3α-positive puncta; (c) identifying a subject as having asparaginase-resistant cancer if the cancer forms GSK3-positive puncta; and (d) administering an asparaginase and an agent that inhibits GSK3α to a subject who has been identified as having asparaginase-resistant cancer.

Yet another aspect described herein is a method of treating asparaginase-resistant cancer comprising (a) receiving the results of an assay that identifies a subject as having a cancer forming GSK3α-positive puncta; (b) identifying a subject as having asparaginase-resistant cancer if the cancer forms GSK3α-positive puncta; and (c) administering an asparaginase and an agent that inhibits GSK3α to a subject who has been identified as having asparaginase-resistant cancer.

Another aspect described herein is a method of treating cancer comprising (a) obtaining a biological tumor sample from a subject having cancer; (b) assaying the sample by treating with an asparaginase, or culturing in conditions of asparagine starvation or amino acid starvation; (c) identifying the sample as forming GSK3α-positive puncta in response to asparagine starvation; and (d) administering an asparaginase and an agent that inhibits GSK3α to a subject who has been identified as having a sample that forms GSK3α-positive puncta.

Another aspect described herein is a method of treating cancer comprising (a) receiving the results of an assay that identifies a subject as having a cancer that forms GSK3α-positive puncta in response to asparaginase treatment or asparagine starvation; and (b) administering an asparaginase and an agent that inhibits GSK3α to a subject who has been identified as having a cancer that forms GSK3α-positive puncta in response to asparagine starvation.

Another aspect described herein is a method of treating asparaginase-resistant cancer comprising (a) obtaining a biological sample from a subject having cancer; (b) assaying the sample to identify formation of GSK3α-positive puncta in response to asparaginase treatment or asparagine starvation; (c) identifying a subject as having asparaginase-resistant cancer if the cancer forms GSK3α-positive puncta in response to asparagine starvation; and (d) administering an asparaginase and an agent that inhibits GSK3α to a subject who has been identified as having asparaginase-resistant cancer.

Another aspect described herein is a method of treating asparaginase-resistant cancer comprising (a) receiving the results of an assay that identifies a subject as having a cancer that forms GSK3α-positive puncta in response to asparaginase treatment or asparagine starvation; (b) administering an asparaginase and an agent that inhibits GSK3α to a subject who has been identified as having asparaginase-resistant cancer.

In various embodiments, methods described herein comprise the step of diagnosing a subject with having cancer or receiving the results of an assay that diagnoses a subject of having cancer prior to administering the treatment (e.g., an asparaginase and/or an agent that inhibits GSK3α). A skilled clinician can diagnose a subject as having cancer using various assays known in the art. Exemplary assays include: (1) a physical exam, in which a skilled clinician feels areas of the subject's body for lumps that may indicate a tumor, or for abnormalities, such as changes in skin color or enlargement of an organ, that may indicate the presence of cancer; (2) laboratory tests, such as urine and blood tests, to identify abnormalities caused by cancer. For example, in people with leukemia, a common blood test called complete blood count may reveal an unusual number or type of white blood cells; (3) Noninvasive imaging tests to examine your bones and internal organs for signs of cancer or tumors. Imaging tests used in diagnosing cancer may include a computerized tomography (CT) scan, bone scan, magnetic resonance imaging (MRI), positron emission tomography (PET) scan, ultrasound and X-ray, among others; and (4) biopsy, in which a skilled clinician collects a sample of cells from an area of the body that is suspected of having cancer for testing. Biopsies can be obtained using any method known in the art. Biopsy samples are examined to identify the presence of cancer cells using standards known in the art.

An assay for diagnosing cancer need not be performed by a clinician performing the methods of treating described herein. For example, a first clinician can perform the assay to diagnose and provide the results of the assay to a second clinician, who will perform the methods of treatment described herein.

Methods of Identifying Asparaginase-Resistant Cancer

Further, methods provided wherein are directed at identifying a subject as having asparaginasc-resistant, or identifying a subject as being a strong candidate for an asparaginase and GSK3α inhibitor combination treatment. Data provided herein in the Examples show that a subject having asparaginase-resistant is a strong candidate for an asparaginase and GSK3α inhibitor combination treatment.

Thus, one aspect described herein is a method of identifying a subject as having asparaginasc-resistant cancer comprising (a) obtaining a biological sample from a subject having cancer; (b) assaying the sample to identify for GSK3α-positive puncta; and (c) identifying a subject as having asparaginase-resistant cancer if the cancer has GSK3α-positive puncta.

Another aspect described herein is a method of identifying a subject as having asparaginase-resistant cancer comprising (a) receiving the results of an assay that identifies a subject as having a cancer forming GSK3α-positive puncta; and (b) identifying a subject as having asparaginase-resistant cancer if the cancer forms GSK3α-positive puncta.

Yet another aspect provided herein is a method of identifying a subject as having asparaginase-resistant cancer comprising (a) obtaining a biological sample from a subject having cancer; (b) treating the sample with asparaginase, or asparagine starvation, or amino acid starvation; (c) assaying the sample to identify formation of GSK3α-positive puncta; and (d) identifying a subject as having asparaginase-resistant cancer if the sample forms GSK3α-positive puncta.

GSK3α Puncta

GSK3α activity mediates asparaginase resistance in a manner dependent on its N-terminal intrinsically disordered domain. In a wild-type cell, under native conditions, GSK3α is present diffusely in the cytoplasm. However, findings presented herein in the Examples show that a cell which is resistant to asparaginase monotherapy forms GSK3α puncta following response to asparagine starvation, or an asparaginase treatment. GSK3α puncta contain HSP70 and appear to function in protein ubiquitination for proteasomal degradation. It is specifically contemplated herein that GSK3α puncta provide a cellular mechanism for efficient protein degradation in response to asparagine starvation, a catabolic source of amino acids required for asparaginase resistance. As used herein, "puncta" refers to a small, circular aggregate of GSK3α protein. "Puncta" and "bodies" are used interchangeably herein and are meant to refer to the same GSK3α aggregate.

In one embodiment, a cell is identified as forming GSK3α puncta if at least 50% of GSK3α present in the cell is present in puncta in response to asparagine starvation, or an asparaginase ginase treatment. In one embodiment, a cell is identified as forming GSK3α puncta if at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more of GSK3α present in the cell is present in puncta in response to asparagine starvation, or an asparaginase treatment. In one embodiment, the level of GSK3α present in a GSK3α-positive puncta is compared to an appropriate control. As used herein, "appropriate control" refers to an otherwise identical sample population that is not treated with asparaginase or asparagine starvation. In an alternative embodiment, the level of GSK3α present in a GSK3α-positive puncta is compared to the amount of diffuse, cytosolic GSK3α. One skilled in the art can determine the level of diffuse, cytosolic GSK3α using standard techniques, such as cell fractionation to isolate the cytosolic fraction and measuring the level of GSK3α in that fraction, e.g., via western blotting. GSK3α-positive puncta can be isolated and measured using techniques described herein. In one embodiment, the level of GSK3α present in a GSK3α-positive puncta is the level of GSK3α present in a GSK3α-positive puncta as compared to the total level of the f GSK3α present in the cell.

In one embodiment, a cell is identified as forming GSK3α puncta if at least 1 GSK3α punctum is formed in response to asparagine starvation, or an asparaginase treatment. In one embodiment, a cell is identified as forming GSK3α puncta if at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more GSK3α puncta are formed in response to asparagine starvation, or an asparaginase treatment. In one embodiment, the formation of GSK3α-positive puncta are compared to an appropriate control. As used herein, "appropriate control" refers to an otherwise identical sample population that is not treated with asparaginase or asparagine starvation.

In one embodiment, a sample is assayed to identify or visualize formation of GSK3α puncta. In one embodiment, assaying is immunofluorescence or fluorescence activated cell sorting or flow cytometry. One can, e.g., contact a sample an anti-GSK3α antibody visualize GSK3α puncta. Anti-GSK3α antibodies are known in the art and are commercially available. Exemplary anti-GSK3α antibodies are presented herein in Table 1. Standard antibody staining and immunofluorescence techniques are known in the art can be properly executed by a skilled person.

It is specifically contemplated herein that one skilled in the art can readily identify any standard technique for visualizing GSK3α puncta.

In one embodiment, the GSK3α-positive puncta are formed in response to asparagine starvation, or an asparaginase treatment. In one embodiment, assaying is treating the sample with an asparaginase treatment. Treatment with an asparaginase is performed, e.g., by culturing cells in standard cell culture conditions for primary samples, which varies by specimen typ. Cell culture conditions for primary leukemia samples can include Alpha-Minimum Essential Medium supplemented with 10% fetal bovine serum, 10% human AB serum, 1% glutamine, 1% penicillin/streptomycin, and the recombinant human cytokines stem cell factor (50 ng/ml), FLT3 ligand (20 ng/ml), and interleukin-7 (10 ng/ml). Cell culture for primary colorectal cancer samples can include advanced Dulbecco's Modified Eagle Medium/Ham's F-12 supplemented with 2 mM glutamine, 1% penicillin/streptomycin, 1 nM N-acetylcysteine, 10 mM HEPES, and recombinant Noggin (50 ng/ml), Wnt3A (50 ng/ml), EGFP (50 ng/ml) and R-spondin 1. Asparaginase treatment is performed by adding an asparaginase to the cell culture medium, with doses that vary by sample type but can include 100 or 1000 international units liter. The optimal timepoint to assess GSK3α puncta formation after the start of asparaginase therapy varies by sample type, but typically ranges from 12 hours to 5 days.

In one embodiment, assaying is treating the sample with asparagine starvation. Asparagine starvation is performed by culturing cells as described herein above. However, instead of treating with the standard cell culture media indicated above (which are normally supplemented with all amino acids) and then adding an asparaginasc, treatment is instead performed with modified versions of these cell culture media that lack asparagine supplementation, or that lack all amino acids. This avoids the need to treat with an asparaginase. The optimal timepoint of asparagine starvation at which to assess for GSK3α puncta formation varies by sample type, but typically ranges from 12 hours to 5 days.

Biological Sample

GSK3a puncta formation in response to asparagine starvation or asparaginase treatment is a valuable biomarker for identifying a cancer that is resistant to asparaginase monotherapy, and to identify a subject who will respond favorably to a combination asparaginase and GSK3α inhibitor combination therapy.

Methods described herein include the step of obtaining a biological sample from a subject. In one embodiment, the biological sample is a biopsied sample (e.g., tumor sample), a tissue sample, or a blood sample. Exemplary blood samples include, but are not limited to, whole blood, peripheral blood, or cord blood. Exemplary tissue samples include, but are not limited to, skin tissue, breast tissue, ovarian tissue, liver tissue, kidney tissue, lung tissue, pancreatic tissue, thyroid tissue, thymus tissue, spleen tissue, bone marrow, lymphoid tissue, epithelial tissue, endothelial tissue, ectoderm tissue, nervous tissue, connective tissue, and mesoderm tissue. Exemplary tissues further include, but are but not limited to adipose tissue/fat, peripheral blood mononuclear cells, B cells, T cells, monocytes, brain tissue (frontal cortex, temporal cortex, PONS), breast, buccal cells/epithelium, cartilage, cerebellum, colon, cortex (prefrontal-, frontal-, occipital-, temporal cortex), epidermis, fibroblasts (e.g. dermal fibroblasts), gastric tissue, glial cells, head/neck tissue, kidney, lung, liver, mesenchymal stromal cells, neurons, pons, prostate, saliva, heart tissue, stomach, uterine cervix, and many other tissues/cell types.

A biological sample can be obtained from a subject using techniques known in the art, e.g., removing blood directly from a subject's vein, or obtaining a dried blood spot sample. Tissue samples can be obtained by one skilled in the art using, e.g., standard biopsy techniques for a given tissue.

Cancer

As used herein, "cancer" refers to a hyperproliferation of cells that have lost normal cellular control, resulting in unregulated growth, lack of differentiation, local tissue invasion, and metastasis. Cancers are classified based on the histological type (e.g., the tissue in which they originate) and their primary site (e.g., the location of the body the cancer first develops), and can be a carcinoma, a melanoma, a sarcoma, a myeloma, a leukemia, or a lymphoma. "Cancer" can also refer to a solid tumor. As used herein, the term "tumor" refers to an abnormal growth of cells or tissues, e.g., of malignant type or benign type. "Cancer" can be metastatic, meaning the cancer cells have disseminated from its primary site of origin and migrated to a secondary site.

In various embodiments, the cancer treated herein is a carcinoma, a melanoma, a sarcoma, a myeloma, a leukemia, a lymphoma, or a solid tumor.

A carcinoma is a cancer that originates in an epithelial tissue. Carcinomas account for approximately 80-90% of all cancers. Carcinomas can affect organs or glands capable of secretion (e.g., breasts, lung, prostate, colon, or bladder). There are two subtypes of carcinomas: adenocarcinoma, which develops in an organ or gland, and squamous cell carcinoma, which originates in the squamous epithelium. Adenocarcinomas generally occur in mucus membranes, and are observed as a thickened plaque-like white mucosa. They often spread easily through the soft tissue where they occur. Exemplary adenocarcinomas include, but are not limited to, lung cancer, prostate cancer, pancreatic cancer, esophageal cancer, and colorectal cancer. Squamous cell carcinomas can originate from any region of the body. Examples of carcinomas include, but are not limited to, prostate cancer, colorectal cancer, microsatellite stable colon cancer, microsatellite instable colon cancer, hepatocellular carcinoma, breast cancer, lung cancer, small cell lung cancer, non-small cell lung cancer, lung adenocarcinoma, melanoma, basal cell carcinoma, squamous cell carcinoma, renal cell carcinoma, ductal carcinoma in situ, ductal carcinoma.

Sarcomas are cancers that originate in supportive and connective tissues, for example bones, tendons, cartilage, muscle, and fat. Sarcoma tumors usually resemble the tissue in which they grow. Non-limiting examples of sarcomas include, Osteosarcoma or osteogenic sarcoma (originating from bone), Chondrosarcoma (originating from cartilage), Leiomyosarcoma (originating from smooth muscle), Rhabdomyosarcoma (originating from skeletal muscle), Mesothelial sarcoma or mesothelioma (originate from membranous lining of body cavities), Fibrosarcoma (originating from fibrous tissue), Angiosarcoma or hemangioendothelioma (originating from blood vessels), Liposarcoma (originating from adipose tissue), Glioma or astrocytoma (originating from neurogenic connective tissue found in the brain), Myxosarcoma (originating from primitive embryonic connective tissue), or Mesenchymous or mixed mesodermal tumor (originating from mixed connective tissue types).

Melanoma is a type of cancer forming from pigment-containing melanocytes. Melanoma typically develops in the skin, but can occur in the mouth, intestine, or eye.

Myelomas are cancers that originate in plasma cells of bone marrow. Non-limiting examples of myelomas include multiple myeloma, plasmacytoma and amyloidosis.

Lymphomas develop in the glands or nodes of the lymphatic system (e.g., the spleen, tonsils, and thymus), which purifies bodily fluids and produces white blood cells, or lymphocytes. Unlike leukemia, lymphomas form solid tumors. Lymphoma can also occur in specific organs, for example the stomach, breast, or brain; this is referred to as extranodal lymphomas). Lymphomas are subclassified into two categories: Hodgkin lymphoma and Non-Hodgkin lymphoma. The presence of Reed-Sternberg cells in Hodgkin lymphoma diagnostically distinguishes Hodgkin lymphoma from Non-Hodgkin lymphoma. Non-limiting examples of lymphoma include Diffuse large B-cell lymphoma (DLBCL), Follicular lymphoma, Chronic lymphocytic leukemia (CLL), Small lymphocytic lymphoma (SLL), Mantle cell lymphoma (MCL), Marginal zone lymphomas, Burkitt lymphoma, hairy cell leukemia (HCL). In one embodiment, the cancer is DLBCL or Follicular lymphoma.

Leukemias (also known as "blood cancers") are cancers of the bone marrow, which is the site of blood cell production. Leukemia is often associated with the overproduction of immature white blood cells. Immature white blood cells do not function properly, rendering the patient prone to infection. Leukemia additionally affects red blood cells, and can cause poor blood clotting and fatigue due to anemia.

In one embodiment of any aspect, the leukemia is acute myeloid leukemia (AML), Chronic myeloid leukemia (CML), Acute lymphocytic leukemia (ALL), and Chronic lymphocytic leukemia (CLL). Examples of leukemia include, but are not limited to, Myelogenous or granulocytic leukemia (malignancy of the myeloid and granulocytic white blood cell series), Lymphatic, lymphocytic, or lymphoblastic leukemia (malignancy of the lymphoid and lymphocytic blood cell series), and Polycythemia vera or erythremia (malignancy of various blood cell products, but with red cells predominating).

In one embodiment, the cancer is a solid tumor. Non-limiting examples of solid tumors include Adrenocortical Tumor, Alveolar Soft Part Sarcoma, Chondrosarcoma, Colorectal Carcinoma, Desmoid Tumors, Desmoplastic Small Round Cell Tumor, Endocrine Tumors, Endodermal Sinus Tumor, Epithelioid Hemangioendothelioma, Ewing Sarcoma, Germ Cell Tumors (Solid Tumor), Giant Cell Tumor of Bone and Soft Tissue, Hepatoblastoma, Hepatocellular Carcinoma, Melanoma, Nephroma, Neuroblastoma, Non-Rhabdomyosarcoma Soft Tissue Sarcoma (NRSTS), Osteosarcoma, Paraspinal Sarcoma, Renal Cell Carcinoma, Retinoblastoma, Rhabdomyosarcoma, Synovial Sarcoma, and Wilms Tumor. Solid tumors can be found in bones, muscles, or organs, and can be sarcomas or carinomas.

In one embodiment of any aspect, the cancer is resistant to a cancer therapy. In one embodiment of any aspect, the cancer is resistant to an asparaginase. A cancer resistant to a therapy, for example, asparaginase, is one that previously responded to the treatment but is now capable of growing or persisting despite the presence of continued treatment. Resistance to a therapy can occur due to, e.g., acquired mutations in the cancer cell, gene amplification in the cancer cell, or the cancer cell develops mechanisms to prevent the uptake of the treatment. In one embodiment of any aspect, the cancer is not resistant to a cancer therapy or asparaginase.

In one embodiment, the cancer is metastatic (e.g., the cancer has disseminated from its primary location to at least one secondary location).

In one embodiment, the cancer has relapsed following administration of a cancer therapy. A "relapsed cancer" is defined as the return of a disease or the signs and symptoms of a disease after a period of improvement.

Asparaginase and Agents that Inhibit GSK3α

Asparaginase, an antileukemic enzyme that degrades the nonessential amino acid asparagine is a chemotherapy drug used to treat acute lymphoblastic leukemia (ALL). It can also be used to treat some other blood disorders. Asparaginase is also known in the art as, e.g., Erwinase, Crisantaspase or L-asparaginase. Asparaginase catalyzes the conversion of L-asparagine to aspartic acid and ammonia, thus depriving the leukemic cell of circulating asparagine, which leads to cell death.

In one embodiment, the asparaginase is L-asparaginase (Elspar), pegaspargase (PEG-asparaginase; Oncaspar), SC-PEG asparaginase, Calaspargase pegol (Cal-PEG; SHP663), *Erwinia* asparaginase (Erwinaze), cristantaspase, Asparaginase medac, Recombinant Crisantaspase, or Recombinant Crisantaspase with half-life extension or pegylation.

L-asparaginase (Elspar), pegaspargase (PEG-asparaginasc; Oncaspar), and SC-PEG asparaginase (Calaspargase pegol) are all based on the *Escherichia coli* asparaginase gene ansB, either in its native form or conjugated to polyethylene glycol (pegylated), which encodes a gene product having a sequence of SEQ ID NO: 3.

(SEQ ID NO: 3)

```
MEFFKKTALAALVMGFSGAALALPNITILATGGTIAGGGDSATKSNYT
VGKVGVENLVNAVPQLKDIANVKGEQVVNIGSQDMNDNVWLTLAKKIN
TDCDKTDGFVITHGTDTMEETAYFLDLTVKCDKPVVMVGAMRPSTSMS
ADGPFNLYNAVVTAADKASANRGVLVVMNDTVLDGRDVTKTNTTDVAT
FKSVNYGPLGYIHNGKIDYQRTPARKHTSDTPFDVSKLNELPKVGIVY
NYANASDLPAKALVDAGYDGIVSAGVGNGNLYKSVFDTLATAAKTGTA
VVRSSRVPTGATTQDAEVDDAKYGFVASGTLNPQKARVLLQLALTQTK
DPQQIQQIFNQY
```

The *Erwinia* asparaginases (Erwinaze, Recombinant Crisantaspase, or Recombinant Crisantaspase with half-life extension) are based on the ansB gene from *Erwinia chrysanthemi* (also known as *Dickeya chrysanthemi*), either in its native form or conjugated to polyethylene glycol (pegylated), which encodes a gene product having a sequence of SEQ ID NO: 4.

(SEQ ID NO: 4)

```
MERWFKSLFVLVLFFVFTASAADKLPNIVILATGGTIAGSAATGTQTT
GYKAGALGVDTLINAVPEVKKLANVKGEQFSNMASENMTGDVVLKLSQ
RVNELLARDDVDGVVITHGTDTVEESAYFLHLTVKSDKPVVFVAAMRP
ATAISADGPMNLLEAVRVAGDKQSRGRGVMVVLNDRIGSARYITKTNA
STLDTFKANEEGYLGVIIGNRIYYQNRIDKLHTTRSVFDVRGLTSLPK
VDILYGYQDDPEYLYDAAIQHGVKGIVYAGMGAGSVSVRGIAGMRKAM
EKGVVVIRSTRTGNGIVPPDEELPGLVSDSLNPAHARILLMLALTRTS
DPKVIQEYFHTY
```

In one embodiment, the asparaginase encodes a gene product having a sequence that comprises a sequence with at least 80%, at least 85%, at least 90%, at least 95%, at least 96%, at least 97%, at least 98%, at least 99% or greater sequence identity to the sequence of SEQ ID NO: 3 or 4. In one embodiment, the asparaginase encodes a gene product having a sequence that comprises the entire sequence of SEQ ID NO: 3 or 4. In another embodiment, the asparaginase encodes a gene product having a sequence of SEQ ID NO: 3 or 4, wherein the fragment retains the desired function of asparaginase, e.g., the antileukemic enzymatic activity.

Methods for purifying and delivering asparaginases, and compositions comprising asparaginases are further described in, e.g., U.S. Pat. Nos. 3,440,142; 3,511,754; 3,511,755; 3,597,323; 3,652,402; 3,620,925; 3,686,072; 3,773,624; 4,617,271; 6,368,845; 7,666,652; 9,181,552; 9,920,311; 10,273,444; U.S. Patent Publication No. 2002/0102251; 2003/0186380; 2010/00183765; 2012/0100249; 2013/0023029; and international Application No. WO1999/039732; the contents of which are incorporated herein by reference in their entireties.

In one aspect, an agent that inhibits GSK3α is administered in combination with an asparaginase to a subject having cancer, e.g., leukemia. In one embodiment, the agent that inhibits GSK3α is a small molecule, an antibody or antibody fragment, a peptide, an antisense oligonucleotide, a genome editing system, or an RNAi.

In one embodiment, inhibition of GSK3α is the inhibition of GSK3α levels or activity in a cell. In one embodiment, the level or activity of GSK3α in a cell is decreased by at least 10% following contact with a GSK3α inhibitor. In one embodiment, the level or activity of GSK3α in a cell is decreased by at least 5%, 10%, 15%, 20%, 25%, 30%, 35%, 40%, 45%, 50%, 55%, 60%, 65%, 70%, 75%, 80%, 85%, 90%, 95%, or 99% or more following contact with a GSK3α inhibitor as compared to an appropriate control. As used herein, an appropriate control is an otherwise identical cell source that is not treated with a GSK3α inhibitor. Protein or mRNA levels of GSK3α can be measured using standard techniques known in the art, for example, western blotting or PCR-based assays, respectively. Activity levels of GSK3α can be measured using standard biological assays for GSK3α, e.g., as described herein.

In one embodiment, inhibition of GSK3α is the inhibition of GSK3α puncta formation. In one embodiment, inhibition of GSK3α is the reduction of GSK3α puncta formation. In one embodiment, the GSK3α puncta formation in a cell is reduced by at least 10% following contact with a GSK3α inhibitor. In one embodiment, the GSK3α puncta formation in a cell is reduced by at least 5%, 10%, 15%, 20%, 25%, 30%, 35%, 40%, 45%, 50%, 55%, 60%, 65%, 70%, 75%, 80%, 85%, 90%, 95%, or 99% or more following contact with a GSK3α inhibitor as compared to an appropriate control. As used herein, an appropriate control is an otherwise identical cell source that is not treated with a GSK3α inhibitor. Cytoplasmic GSK3α puncta co-localized with the heat shock protein 70 (HSP70), K48-linked ubiquitin and the proteasome. Accordingly, one skilled in the art can determine if a GSK3α puncta has formed, and the quantity thereof, e.g., via immunofluorescence confocal microscopy to assess the localization of GSK3α, HSP70, K48-linked ubiquitin and the proteasome.

In one embodiment, inhibition of GSK3α is the inhibition of GSK3α translocation to a cytoplasmic body (e.g., puncta). In one embodiment, inhibition of GSK3α is the reduction of GSK3α translocation to a cytoplasmic body (e.g., puncta). In one embodiment, the GSK3α translocation to a cytoplasmic body (e.g., puncta) in a cell is reduced by at least 10% following contact with a GSK3α inhibitor. In one embodiment, the GSK3α translocation to a cytoplasmic body (e.g., puncta) in a cell is reduced by at least 5%, 10%, 15%, 20%, 25%, 30%, 35%, 40%, 45%, 50%, 55%, 60%, 65%, 70%, 75%, 80%, 85%, 90%, 95%, or 99% or more following contact with a GSK3α inhibitor as compared to an appropriate control. As used herein, an appropriate control is an otherwise identical cell source that is not treated with a GSK3α inhibitor. Cytoplasmic GSK3α bodies colocalized with the heat shock protein 70 (HSP70), K48-linked ubiquitin and the proteasome. Accordingly, one skilled in the art can determine if GSK3α has translocated to puncta, e.g., via immunofluorescence confocal microscopy to assess the localization of GSK3α, HSP70, K48-linked ubiquitin and the proteasome. If translocation has not occurred, a skilled person would expect to observe diffuse, cytoplasmic GSK3α.

An agent described herein targets GSK3α for its inhibition. An agent is considered effective for inhibiting GSK3α if, for example, upon administration, it inhibits the presence, amount, activity and/or level of GSK3α in the cell. In one embodiment, an agent that inhibits the level and/or activity of GSK3α by at least 10%, by at least 20%, by at least 30%, by at least 40%, by at least 50%, by at least 60%, by at least 70%, by at least 80%, by at least 90%, by at least 100% or more as compared to an appropriate control. As used herein, an "appropriate control" refers to the level and/or activity of GSK3α prior to administration of the agent, or the level and/or activity of GSK3α in a population of cells that was not in contact with the agent. Inhibition of GSK3α will prevent activation of the WNT signaling pathway. One skilled in the art can determine if the presence, amount or level of GSK3α has been reduced using PCR-based assays or western blotting to assess GSK3α mRNA or protein levels, respectively, or by visualizing the GSK3α protein via immunofluorescence of an anti-GSK3α antibody. One skilled in the art can determine if the activity of GSK3α has been reduced using functional assays that assess downstream effects of GSK3α, such as, determining if its downstream substrate, β-catenin, is phosphorylated via western blotting or immunofluorescence with an anti-phospho β-catenin specific antibody.

An agent can inhibit e.g., the transcription, or the translation of GSK3α in the cell. An agent can inhibit the activity or alter the activity (e.g., such that the activity no longer occurs, or occurs at a reduced rate) of GSK3α in the cell (e.g., GSK3α's expression).

In one embodiment, an agent that inhibits GSK3α promotes programmed cell death, e.g., kills the cell. To determine is an agent is effective at inhibiting GSK3α, mRNA and protein levels of a given target (e.g., GSK3α) can be assessed using RT-PCR and western-blotting, respectively. Biological assays that detect the activity of GSK3α (e.g., WNT activation) can be used to assess if programmed cell death has occurred.

The agent may function directly in the form in which it is administered. Alternatively, the agent can be modified or utilized intracellularly to produce something which inhibits GSK3α, such as introduction of a nucleic acid sequence into the cell and its transcription resulting in the production of the nucleic acid and/or protein inhibitor of GSK3α. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be identified from a library of diverse compounds.

In various embodiments, the agent is a small molecule that inhibits GSK3α. Exemplary small molecular inhibitors of GSK3 include BRD0705, BRD4963, BRD1652, BRD3731, CHIR-98014, LY2090314, AZD1080, CHIR-99021 (CT99021) HCl, CHIR-99021 (CT99021), BIO-acetoxime, SB216763, SB415286, Abemaciclib (LY2835210), AT-9283, RGB-286638, PHA-793887, AT-7519, AZD-5438, OTS-167, 9-ING-41, Tideglusib (NP031112), and AR-A014418. Chemical structures for exemplary small molecular inhibitors of GSK3α are shown in Table 2.

TABLE 2

Chemical structures for exemplary small molecular inhibitors of GSK3α.

| | | | |
|---|---|---|---|
| BRD0705 | 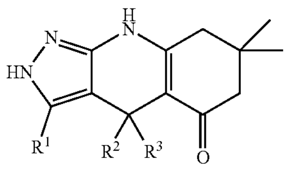 | $R^1$ | H |
| | | $R^2$ | Et |
| | | $R^3$ | 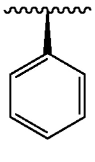 |
| BRD4963 | 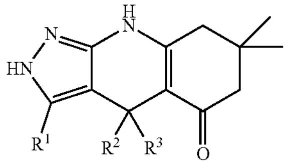 | $R^1$ | $CH_3$ |
| | | $R^2$ | 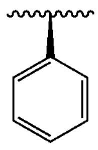 |
| | | $R^3$ | H |

TABLE 2-continued
Chemical structures for exemplary small molecular inhibitors of GSK3α.
BRD1652
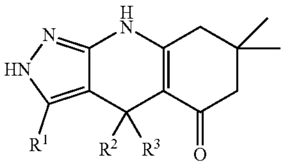
$R^1$ $CF_3$
$R^2$
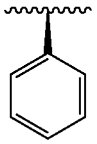
$R^3$ $CH_3$
BRD3731
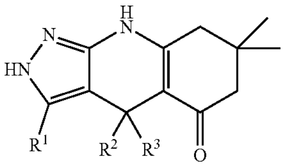
$R^1$
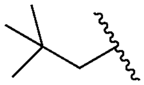
$R^2$ Me
$R^3$
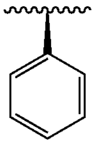
CHIR-98014
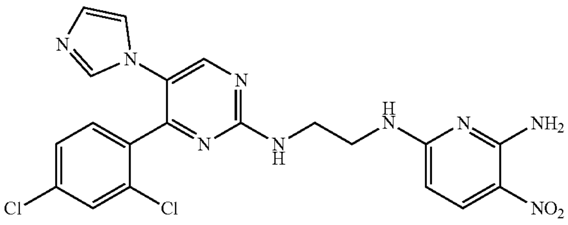 [SMILES: Nc1nc(NCCNc2ncc(-n3ccnc3)c(-c3ccc(Cl)cc3Cl)n2)ccc1[N+](=O)[O-]]
LY2090314
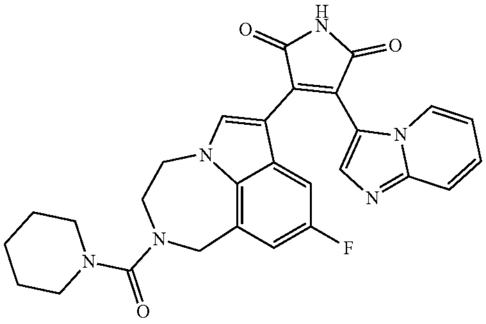 [SMILES: O=C1NC(=O)C(c2cnc3ccccn23)=C1c1cn2c3c(cc(F)cc13)CN(C(=O)N1CCCCC1)CC2]
AZD1080
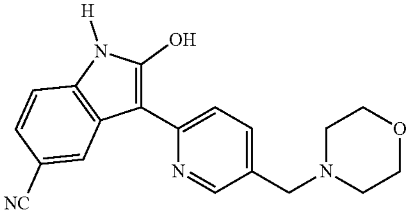 [SMILES: N#Cc1ccc2[nH]c(O)c(-c3ccc(CN4CCOCC4)cn3)c2c1]

TABLE 2-continued
| Chemical structures for exemplary small molecular inhibitors of GSK3α. | |
|---|---|
| CHIR-99021 (CT99021) | 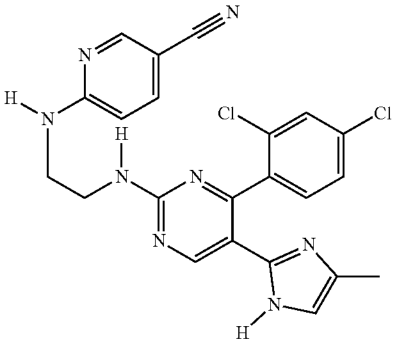 [SMILES: Cc1c[nH]c(-c2cnc(NCCNc3ccc(C#N)cn3)nc2-c2ccc(Cl)cc2Cl)n1] |
| BIO-acetoxime | 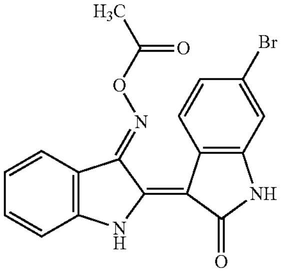 [SMILES: CC(=O)O/N=C1/C(=C2/C(=O)Nc3cc(Br)ccc32)Nc2ccccc21] |
| SB216763 | 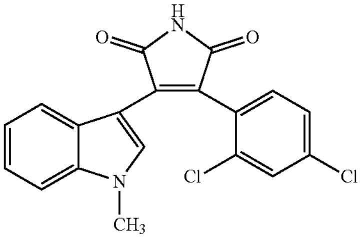 [SMILES: Cn1cc(C2=C(c3ccc(Cl)cc3Cl)C(=O)NC2=O)c2ccccc21] |
| SB415286 | 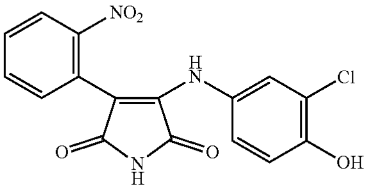 [SMILES: O=C1NC(=O)C(c2ccccc2[N+](=O)[O-])=C1Nc1ccc(O)c(Cl)c1] |
| Abemaciclib (LY2835210) | 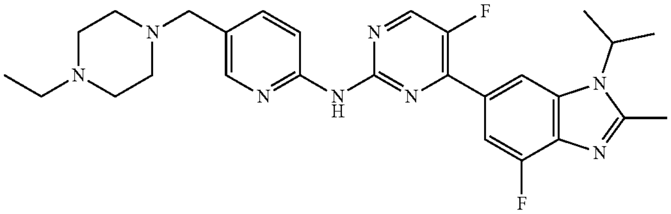 [SMILES: CCN1CCN(Cc2ccc(Nc3ncc(F)c(-c4cc(F)c5nc(C)n(C(C)C)c5c4)n3)nc2)CC1] |
| AT-9283 | 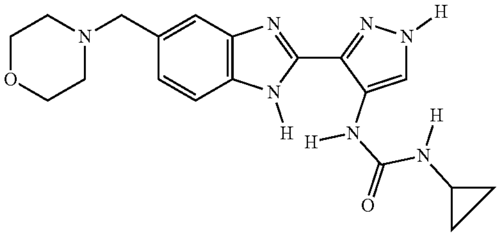 [SMILES: O=C(Nc1c[nH]nc1-c1nc2cc(CN3CCOCC3)ccc2[nH]1)NC1CC1] |

TABLE 2-continued
| Chemical structures for exemplary small molecular inhibitors of GSK3α. | |
|---|---|
| RGB-286638 | 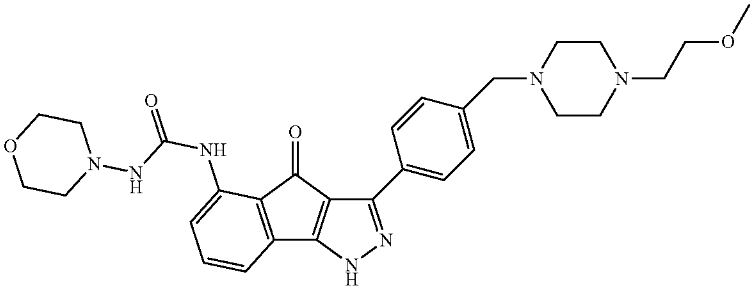 [SMILES: COCCN1CCN(Cc2ccc(-c3n[nH]c4c3C(=O)c3c(NC(=O)NN5CCOCC5)cccc3-4)cc2)CC1] |
| PHA-793887 | 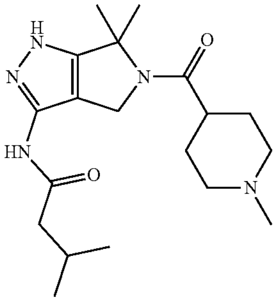 [SMILES: CC(C)CC(=O)Nc1n[nH]c2c1CN(C(=O)C1CCN(C)CC1)C2(C)C] |
| AT-7519 | 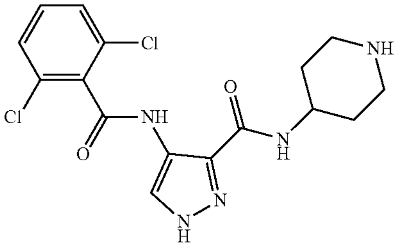 [SMILES: O=C(NC1CCNCC1)c1n[nH]cc1NC(=O)c1c(Cl)cccc1Cl] |
| AZD-5438 | 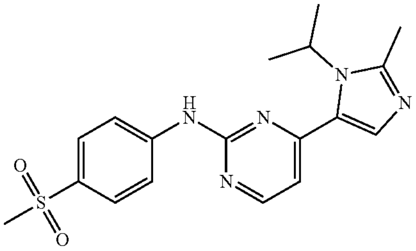 [SMILES: Cc1ncc(-c2ccnc(Nc3ccc(S(C)(=O)=O)cc3)n2)n1C(C)C] |
| OTS-167 | 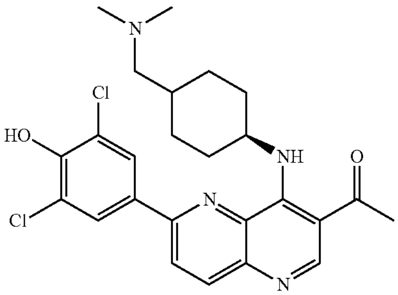 |

TABLE 2-continued

| Chemical structures for exemplary small molecular inhibitors of GSK3α. | |
|---|---|
| 9-ING-41 | 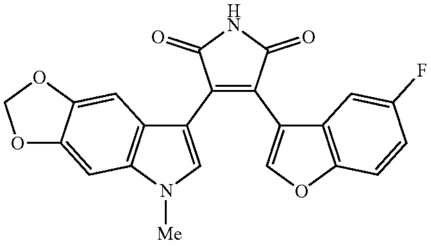 [SMILES: Cn1cc(C2=C(c3coc4ccc(F)cc34)C(=O)NC2=O)c2cc3c(cc21)OCO3] |
| Tideglusib (NP031112) | 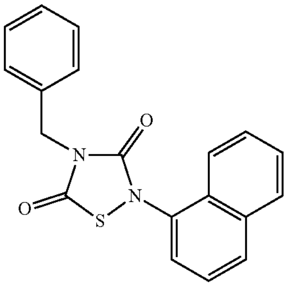 [SMILES: O=c1sn(-c2cccc3ccccc23)c(=O)n1Cc1ccccc1] |
| AR-A014418 | 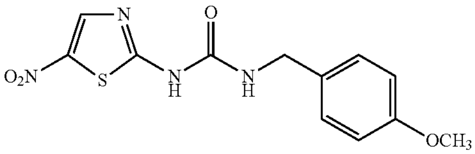 [SMILES: COc1ccc(CNC(=O)Nc2ncc([N+](=O)[O-])s2)cc1] |

Further, in one embodiment, the small molecule is a derivative, a variant, or an analog of, or is substantially similar to any of the small molecules described herein, for example as listed in Table 2. A molecule is said to be a "derivative" of another molecule when it contains additional chemical moieties not normally a part of the molecule and/or when it has been chemically modified. Such moieties can improve the molecule's expression levels, enzymatic activity, solubility, absorption, biological half-life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, PA (1990). A "variant" of a molecule is meant to refer to a molecule substantially similar in structure and function to either the entire molecule, or to a fragment thereof. A molecule is said to be "substantially similar" to another molecule if both molecules have substantially similar structures and/or if both molecules possess a similar biological activity. Thus, provided that two molecules possess a similar activity, they are considered variants as that term is used herein even if the structure of one of the molecules not found in the other, or if the structure is not identical. An "analog" of a molecule is meant to refer to a molecule substantially similar in function to either the entire molecule or to a fragment thereof.

In one embodiment, the small molecule inhibitor of GSK3α, e.g., a small molecule listed in Table 2, is conjugated to an E3 ubiquitin ligase recruitment element. As used herein, "conjugated" refers to two or more smaller entities (e.g., a small molecule and a E3 ubiquitin ligase recruitment element) that are linked, connected, associated, bonded (covalently or non-covalently), or any combination thereof, to form a larger entity. The conjugated E3 ubiquitin ligase recruitment element recruits an E3, which mediates the transfer of an ubiquitin from an E2 to the protein substrate. Binding of an ubiquitin to a protein substrate marks the protein for degradation via the ubiquitin proteasome system. Thus, a small molecule inhibitor of GSK3α conjugated to an E3 ubiquitin ligase recruitment element would, e.g., bind to GSK3α and subsequently promote its degradation. E3 ubiquitin ligase recruitment elements can include, but are not limited to, thalidomide, lenalidomide, pomalidomide, or a VHL ligand that mimics the hydroxyproline degradation motif of HIFI-alpha. Chemical structures for exemplary E3 ubiquitin ligase recruitment element are presented herein in Table 3, and are further described in, e.g., Pavia, S L, and Crews, C M. Current Opinion in Chemical Biology. 2019. 50; 111-119, the contents of which are incorporated herein by reference in its entirety. Use of conjugated E3 ubiquitin ligase recruitment elements are further described in U.S. Pat. Nos. 7,208,157B2 and 9,770,512, the contents of which are incorporated herein by reference in its entirety.

In one embodiment, a small molecule conjugated to an E3 ubiquitin ligase recruitment element further comprises a linker. In one embodiment, the inhibitor of GSK3α is a heterobifunctional GSK3a degrader (e.g., as shown herein Table 3). It is specifically contemplated herein that the specifications of the linker (e.g., length, sequence, etc.) would be optimized for greatest efficacy of the small molecule and E3 ubiquitin ligase recruitment element. For example, a linker would be designed such that it does not interfere with binding of the small molecule to its target (e.g., the binding pocket on the protein of interest) or the transfer of the ubiquitin from the E2 to the protein substrate.

In various embodiments, the agent that inhibits GSK3α is an antibody or antigen-binding fragment thereof, or an antibody reagent that is specific for GSK3α. As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., Eur J. Immunol. 1996; 26 (3): 629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, nanobodies, humanized antibodies, chimeric antibodies, and the like.

In one embodiment, the antibody or antibody reagent binds to an amino acid sequence that corresponds to the amino acid sequence encoding GSK3α (SEQ ID NO: 2).

```
                                          (SEQ ID NO: 2)
MSGGGPSGGGPGGSGRARTSSFAEPGGGGGGGGGGPGGSASGPGGTGG

GKASVGAMGGGVGASSSGGGPGGSGGGGSGGPGAGTSFPPPGVKLGRD

SGKVTTVVATLGQGPERSQEVAYTDIKVIGNGSFGVVYQARLAETREL

VAIKKVLQDKRFKNRELQIMRKLDHCNIVRLRYFFYSSGEKKDELYLN

LVLEYVPETVYRVARHFTKAKLTIPILYVKVYMYQLFRSLAYIHSQGV

CHRDIKPQNLLVDPDTAVLKLCDFGSAKQLVRGEPNVSYICSRYYRAP

ELIFGATDYTSSIDVWSAGCVLAELLLGQPIFPGDSGVDQLVEIIKVL

GTPTREQIREMNPNYTEFKFPQIKAHPWTKVFKSRTPPEAIALCSSLL

EYTPSSRLSPLEACAHSFFDELRCLGTQLPNNRPLPPLFNFSAGELSI

QPSLNAILIPPHLRSPAGTTTLTPSSQALTETPTSSDWQSTDATPTLT

NSS
```

In another embodiment, the anti-GSK3α antibody or antibody reagent binds to an amino acid sequence that comprises the sequence of SEQ ID NO: 2; or binds to an amino acid sequence that comprises a sequence with at least 80%, at least 85%, at least 90%, at least 95%, at least 96%, at least 97%, at least 98%, at least 99% or greater sequence identity to the sequence of SEQ ID NO: 2. In one embodiment, the anti-GSK3α antibody or antibody reagent binds to an amino acid sequence that comprises the entire sequence of SEQ ID NO: 2. In another embodiment, the antibody or antibody reagent binds to an amino acid sequence that comprises a fragment of the sequence of SEQ ID NO: 2, wherein the fragment is sufficient to bind its target, e.g., GSK3, and inhibit GSK3α activity and/or expression.

In one embodiment, an anti-GSK3α antibody or antibody reagent is conjugated to an E3 ubiquitin ligase recruitment element. In one embodiment, the anti-GSK3α antibody or antibody reagent conjugated to an E3 ubiquitin ligase recruitment element further comprises a linker.

Exemplary anti-GSK3α antibodies are presented herein in Table 1 below.

TABLE 1

| Antibody | Clone ID | Commercial Source |
|---|---|---|
| GSK3 alpha XP Rabbit monoclonal antibody | D80D1 | Cell Signaling Technology |
| GSK3 alpha Monoclonal Antibody | 6G12C2 | ThermoFisher |
| GSK3 alpha/beta Monoclonal Antibody | 21A | ThermoFisher |
| GSK3 alpha Monoclonal Antibody | SBGSK3a4 | OriGene |
| Mouse anti-Human GSK3 alpha Monoclonal Antibody | 9D5G1 | MyBioSource.com |
| Anti-GSK3 alpha (phospho Ser21) + GSK3 beta (phospho Ser9) antibody | Polyclonal | GeneTex |
| Anti-GSK3 alpha (phospho Ser21) | Polyclonal | Bio-Rad |
| Rb Anti GSK3 Alpha | Polyclonal | Bio-Rad |
| GSK3 alpha/beta (pY279/216) Antibody | Polyclonal | Abbexa Ltd |
| Human Anti GSK3 Alpha | Polyclonal | Rockland Immunochemicals, Inc. |
| Mouse Anti GSK3 Alpha | Polyclonal | NSJ Bioreagents |

In one embodiment, the agent that inhibits GSK3α is an antisense oligonucleotide. As used herein, an "antisense oligonucleotide" refers to a synthesized nucleic acid sequence that is complementary to a DNA or mRNA sequence, such as that of a microRNA. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under cellular conditions to a gene, e.g., GSK3α. Thus, oligonucleotides are chosen that are sufficiently complementary to the target, i.e., that hybridize sufficiently well and with sufficient specificity in the context of the cellular environment, to give the desired effect. For example, an antisense oligonucleotide that inhibits GSK3α may comprise at least 5, at least 10, at least 15, at least 20, at least 25, at least 30, or more bases complementary to a portion of the coding sequence of the human GSK3α gene (e.g., SEQ ID NO: 1), respectively.

In one embodiment, GSK3α is depleted from the cell's genome using any genome editing system including, but not limited to, zinc finger nucleases, TALENS, meganucleases, and CRISPR/Cas systems. In one embodiment, the genomic editing system used to incorporate the nucleic acid encoding one or more guide RNAs into the cell's genome is not a CRISPR/Cas system; this can prevent undesirable cell death in cells that retain a small amount of Cas enzyme/protein. It is also contemplated herein that either the Cas enzyme or the sgRNAs are each expressed under the control of a different inducible promoter, thereby allowing temporal expression of each to prevent such interference.

When a nucleic acid encoding one or more sgRNAs and a nucleic acid encoding an RNA-guided endonuclease each need to be administered in vivo, the use of an adenovirus associated vector (AAV) is specifically contemplated. Other vectors for simultaneously delivering nucleic acids to both components of the genome editing/fragmentation system (e.g., sgRNAs, RNA-guided endonuclease) include lentiviral vectors, such as Epstein Barr, Human immunodeficiency virus (HIV), and hepatitis B virus (HBV). Each of the components of the RNA-guided genome editing system (e.g., sgRNA and endonuclease) can be delivered in a separate vector as known in the art or as described herein.

In one embodiment, the agent inhibits GSK3α by RNA inhibition. Inhibitors of the expression of a given gene can be an inhibitory nucleic acid. In some embodiments of any of the aspects, the inhibitory nucleic acid is an inhibitory RNA (iRNA). The RNAi can be single stranded or double stranded.

The iRNA can be siRNA, shRNA, endogenous microRNA (miRNA), or artificial miRNA. In one embodiment, an iRNA as described herein effects inhibition of the expression and/or activity of a target, e.g. GSK3α. In some embodiments of any of the aspects, the agent is siRNA that inhibits GSK3α. In some embodiments of any of the aspects, the agent is shRNA that inhibits GSK3α.

One skilled in the art would be able to design siRNA, shRNA, or miRNA to target GSK3α, e.g., using publically available design tools. siRNA, shRNA, or miRNA is commonly made using companies such as Dharmacon (Layfayette, CO) or Sigma Aldrich (St. Louis, MO).

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions The RNA of an iRNA can be chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference.

In one embodiment, the agent is miRNA that inhibits GSK3α microRNAs are small non-coding RNAs with an average length of 22 nucleotides. These molecules act by binding to complementary sequences within mRNA molecules, usually in the 3' untranslated (3'UTR) region, thereby promoting target mRNA degradation or inhibited mRNA translation. The interaction between microRNA and mRNAs is mediated by what is known as the "seed sequence", a 6-8-nucleotide region of the microRNA that directs sequence-specific binding to the mRNA through imperfect Watson-Crick base pairing. More than 900 microRNAs are known to be expressed in mammals. Many of these can be grouped into families on the basis of their seed sequence, thereby identifying a "cluster" of similar microRNAs. A miRNA can be expressed in a cell, e.g., as naked DNA. A miRNA can be encoded by a nucleic acid that is expressed in the cell, e.g., as naked DNA or can be encoded by a nucleic acid that is contained within a vector.

The agent may result in gene silencing of the target gene (e.g., GSK3α), such as with an RNAi molecule (e.g. siRNA or miRNA). This entails a decrease in the mRNA level in a cell for a target by at least about 5%, about 10%, about 20%, about 30%, about 40%, about 50%, about 60%, about 70%, about 80%, about 90%, about 95%, about 99%, about 100% of the mRNA level found in the cell without the presence of the agent. In one preferred embodiment, the mRNA levels are decreased by at least about 70%, about 80%, about 90%, about 95%, about 99%, about 100%. One skilled in the art will be able to readily assess whether the siRNA, shRNA, or miRNA effective target e.g., GSK3α, for its downregulation, for example by transfecting the siRNA, shRNA, or miRNA into cells and detecting the levels of a gene (e.g., GSK3α) found within the cell via western-blotting.

The agent may be contained in and thus further include a vector. Many such vectors useful for transferring exogenous genes into target mammalian cells are available. The vectors may be episomal, e.g. plasmids, virus-derived vectors such cytomegalovirus, adenovirus, etc., or may be integrated into the target cell genome, through homologous recombination or random integration, e.g. retrovirus-derived vectors such as MMLV, HIV-1, ALV, etc. In some embodiments, combinations of retroviruses and an appropriate packaging cell line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide (e.g., an GSK3α inhibitor) from nucleic acid sequences contained therein linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

Integrating vectors have their delivered RNA/DNA permanently incorporated into the host cell chromosomes.

Non-integrating vectors remain episomal which means the nucleic acid contained therein is never integrated into the host cell chromosomes. Examples of integrating vectors include retroviral vectors, lentiviral vectors, hybrid adenoviral vectors, and herpes simplex viral vector.

One example of a non-integrative vector is a non-integrative viral vector. Non-integrative viral vectors eliminate the risks posed by integrative retroviruses, as they do not incorporate their genome into the host DNA. One example is the Epstein Barr oriP/Nuclear Antigen-1 ("EBNA1") vector, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free iPSCs. Another non-integrative viral vector is adenoviral vector and the adeno-associated viral (AAV) vector.

Another non-integrative viral vector is RNA Sendai viral vector, which can produce protein without entering the nucleus of an infected cell. The F-deficient Sendai virus vector remains in the cytoplasm of infected cells for a few passages, but is diluted out quickly and completely lost after several passages (e.g., 10 passages).

Another example of a non-integrative vector is a minicircle vector. Minicircle vectors are circularized vectors in which the plasmid backbone has been released leaving only the eukaryotic promoter and cDNA(s) that are to be expressed.

As used herein, the term "viral vector" refers to a nucleic acid vector construct that includes at least one element of viral origin and has the capacity to be packaged into a viral vector particle. The viral vector can contain a nucleic acid encoding a polypeptide as described herein in place of non-essential viral genes. The vector and/or particle may be utilized for the purpose of transferring nucleic acids into cells either in vitro or in vivo. Numerous forms of viral vectors are known in the art.

Administration

In various embodiments, the methods described herein relate to treating a subject having or diagnosed as having cancer (e.g., leukemia, colon cancer, or pancreatic cancer) having GSK3α puncta comprising administering an agent that inhibits GSK3α in combination with an asparaginase as described herein. Subjects having cancer can be identified by a physician using current methods of diagnosing a condition. Symptoms and/or complications of cancer, which characterize this disease and aid in diagnosis are well known in the art. Tests that may aid in a diagnosis of, e.g., cancer, include blood tests and non-invasive imaging. A family history of a particular cancer will also aid in determining if a subject is likely to have the condition or in making a diagnosis of cancer.

The agents described herein (e.g., an agent that inhibits GSK3α) and an asparaginase can be administered in combination to a subject having or diagnosed as having cancer (e.g., leukemia, colon cancer, or pancreatic cancer). Administration of an agent or asparaginase described herein can be performed in a variety of manners, for example, in a single dose, in reoccurring multiple doses, via continuous infusion, via pulsed administration. In one embodiment, an agent or asparaginase described herein can be administered to a subject at least once every 1, 2, 3, 4, 5, 6, 7, 8, 9, 10, 11, 12, 13, 14, 15, 16, 17, 18, 19, 20, 21, 22, 23, or 24 hours; or every 1, 2, 3, 4, 5, 6, or 7 days; or every 1, 2, 3, or 4 weeks; or every 1, 2, 3, 4, 5, 6, 7, 8, 9, 10, 11, or 12 months, or more. It is specifically contemplated herein that the dosing of an agent or asparaginase described herein is determined based on the half-life of the agent, e.g., such that the effect of the agent (for example, inhibition of GSKα) is continuous, or nearly continuous, in the subject. For example, if the half-life of a given GSKα inhibitor is 12 hours, it would be administered every 12 hours to the subject such that it maintains continuous inhibition of GSKα in the subject.

In one embodiment, the agent that inhibits GSK3α and the asparaginase are administered in the same manner, e.g., the agent that inhibits GSK3α and the asparaginase are administered in a single dose, in multiple doses, via continuous infusion, via pulsed administration. In one embodiment, the agent that inhibits GSK3α and the asparaginase are administered in different manners, e.g., the agent that inhibits GSK3α is administered via continuous infusion, and the asparaginase is administered in a single dose.

In one embodiment agent that inhibits GSK3α and the asparaginase are formulated together in one composition for administration. In one embodiment agent that inhibits GSK3α and the asparaginase are formulated in separate compositions and are administered as separate compositions.

In some embodiments, the methods described herein comprise administering an effective amount of the agents to a subject in order to alleviate at least one symptom of a given cancer. As used herein, "alleviating at least one symptom of a given cancer" is ameliorating any condition or symptom associated with cancer. As compared with an equivalent untreated control, such reduction is by at least 5%, 10%, 20%, 40%, 50%, 60%, 80%, 90%, 95%, 99% or more as measured by any standard technique. A variety of means for administering the agents and/or an asparaginase described herein to subjects are known to those of skill in the art. In one embodiment, the agent is administered systemically or locally (e.g., to the affected organ, e.g., the colon). In one embodiment, the agent is administered intravenously. In one embodiment, the agent is administered continuously, in intervals, or sporadically. The route of administration of the agent will be optimized for the type of agent being delivered (e.g., an antibody, a small molecule, an RNAi), and can be determined by a skilled practitioner.

The term "effective amount" as used herein refers to the amount of an agent (e.g., an agent that inhibits GSK3α) and/or an asparaginase that can be administered to a subject having or diagnosed as having cancer (e.g., leukemia, colon cancer, or pancreatic cancer) needed to alleviate at least one or more symptom of cancer. The term "therapeutically effective amount" therefore refers to an amount of an agent and/or an asparaginase that is sufficient to provide a particular anti-cancer effect when administered to a typical subject. An effective amount as used herein, in various contexts, would also include an amount of an agent and/or an asparaginase sufficient to delay the development of a symptom of cancer, alter the course of a symptom of cancer (e.g., slowing the progression of cancer), or reverse a symptom of cancer. Thus, it is not generally practicable to specify an exact "effective amount". However, for any given case, an appropriate "effective amount" can be determined by one of ordinary skill in the art using only routine experimentation.

In one embodiment, the agent and/or an asparaginase is administered continuously (e.g., at constant levels over a period of time). Continuous administration of an agent can be achieved, e.g., by epidermal patches, continuous release formulations, or on-body injectors.

Effective amounts, toxicity, and therapeutic efficacy can be evaluated by standard pharmaceutical procedures in cell cultures or experimental animals. The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the agent, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., measuring neurological function, or blood work, among others. The dosage can be determined by a physician and adjusted, as necessary, to suit observed effects of the treatment.

Dosage

"Unit dosage form" as the term is used herein refers to a dosage for suitable one administration. By way of example a unit dosage form can be an amount of therapeutic disposed in a delivery device, e.g., a syringe or intravenous drip bag. In one embodiment, a unit dosage form is administered in a single administration. In another, embodiment more than one unit dosage form can be administered simultaneously.

Typically, the dosage ranges are between 0.001 mg/kg body weight to 5 g/kg body weight, inclusive. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 μg/kg body weight to 30 μg/kg body weight. Alternatively, the dose range will be titrated to maintain serum levels between 5 μg/mL and 30 μg/mL.

The dosage of the agent and/or an asparaginase as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further cells, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

Combination Treatment

In one aspect, the agent and an asparaginase described herein are administered in combination for the treatment of cancer. Administered "in combination," as used herein, means that two (or more) different treatments (e.g., an asparaginase and an agent that inhibits GSK3α, or a cancer therapy) are delivered to the subject during the course of the subject's affliction with the disorder, e.g., the two or more treatments are delivered after the subject has been diagnosed with the disorder (e.g., cancer) and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The agents described herein and the at least one additional therapy can be administered simultaneously, in the same or in separate compositions, or sequentially. For sequential administration, the agent and/or an asparaginase described herein can be administered first, and the additional agent can be administered second, or the order of administration can be reversed. The agent and/or other therapeutic agents, procedures or modalities can be administered during periods of active disorder, or during a period of remission or less active disease. The agent can be administered before another treatment, concurrently with the treatment, post-treatment, or during remission of the disorder.

When administered in combination, the agent and an asparaginase, or all, can be administered in an amount or dose that is higher, lower or the same as the amount or dosage of each agent used individually, e.g., as a monotherapy. In certain embodiments, the administered amount or dosage of the agent, the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., treatment of cancer) is lower (e.g., at least 20%, at least 30%, at least 40%, or at least 50% lower) than the amount or dosage of each agent individually required to achieve the same therapeutic effect.

In one embodiment, the cancer therapy is selected from the group consisting of chemotherapy, radiation therapy, immunotherapy, surgery, hormone therapy, stem cell therapy, targeted therapy, gene therapy, and precision therapy.

In other embodiments of any method described herein, the cancer therapy is selected from the group consisting of growth inhibitory agents, cytotoxic agents, anti-angiogenesis agents, apoptotic agents, anti-tubulin agents, anti-HER-2 antibodies, anti-CD20 antibodies, an epidermal growth factor receptor (EGFR) antagonist, a HER1/EGFR inhibitor, a platelet derived growth factor inhibitor, a COX-2 inhibitor, an interferon, and a cytokine (e.g., G-CSF, granulocyte-colony stimulating factor).

In other embodiments, the cancer therapy is selected from the group consisting of 13-cis-retinoic acid, 2-CdA, 2-Chlorodeoxyadenosine, 5-Azacitidine, azacytidine, 5-Fluorouracil, 5-FU, 6-Mercaptopurine, 6-MP, 6-TG, 6-Thioguanine, abiraterone acetate, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Axitinib, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Cabazitaxel, Calcium Leucovorin, Campath® Camptosar® Camptothecin-11, Capecitabine, Caprelsa® Carac™ Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Crizotinib, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, Denosumab, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eculizumab, Efudex®, Eligard™, Ellence™, Eloxatin™, Elspar®, Emcyt®, Epirubicin, Epoetin Alpha, Erbitux, Eribulin, Erlotinib, *Erwinia* L-asparaginase, Estramustine, Ethyol, Etopophos®, Etoposide, Etoposide Phosphate, Eulexin®, Everolimus, Evista®, Exemestane, Fareston®, Faslodex® Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, Gefitinib, Gemcitabine, Gemtuzumab ozogamicin, Gemzar, Gleevec™, Gliadel® Wafer, Goserelin, Granulocyte-Colony Stimulating Factor (G-CSF), Granulocyte Macrophage Colony Stimulating Factor (GM-CSF), Halaven®, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Inlyta R, Interferon alpha, Interferon Alpha-2b (PEG Conjugate), Interleukin-2, Interleukin-11, Intron A® (interferon alpha-2b), Ipilimumab, Iressa®, Irinotecan, Isotretinoin, Ixabepilone, Ixempra™, Jevtana®, Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar R, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolia®, Prolifeprospan 20 with Carmustine Implant, Provenge®, Purinethol®, Raloxifene, Revlimid®, Rheumatrex®, Rituxan R, Rituximab, Roferon-A® (Interferon Alfa-2a), Romiplostim, Rubex®, Rubidomycin hydrochloride, Sandostatin®, Sandostatin LAR®, Sargramostim, Sipuleucel-T, Soliris R, Solu-Cortef®, Solu-Medrol®, Sorafenib, SPRYCEL™, STI-571, Streptozocin, SU11248, Sunitinib, Sutent®, Tamoxifen, Tarceva R, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, Valrubicin, Valstar, vandetanib, VCR, Vectibix™, Velban®, Velcade®, Vemurafenib, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xalkori capsules, Xcloda®, Xgeva®, Yervoy®, Zanosar®, Zelboraf, Zevalin™, Zinecard®, Zoladex®, Zoledronic acid, Zolinza, Zometa®, and Zytiga®.

Parenteral Dosage Forms

Parenteral dosage forms of an agents described herein and/or an asparaginase can be administered to a subject by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Controlled and Delayed Release Dosage Forms

In some embodiments of the aspects described herein, an agent and/or an asparaginase is administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of an agent is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with any agent described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUOLITE® A568 and DUOLITE® AP143 (Rohm&Haas, Spring House, Pa. USA).

Efficacy

The efficacy of an agents described herein and/or an asparaginase, e.g., for the treatment of cancer, can be determined by the skilled practitioner. However, a treatment is considered "effective treatment," as the term is used herein, if one or more of the signs or symptoms of cancer are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated (e.g., cancer) according to the methods described herein or any other measurable parameter appropriate. Efficacy can also be measured by a failure of an individual to worsen as assessed by hospitalization, or need for medical interventions (i.e., progression of cancer). Methods of measuring these indicators are known to those of skill in the art and/or are described herein.

Efficacy can be assessed in animal models of a condition described herein, for example, a mouse model or an appropriate animal model of a given cancer, as the case may be. When using an experimental animal model, efficacy of treatment is evidenced when a statistically significant change in a marker is observed, e.g., a reduction in tumor size, or prevention of metastasis.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention can be further described in the following numbered paragraphs:

1. A method of treating cancer, the method comprising:
   a. obtaining a biological sample from a subject having cancer;
   b. assaying the sample and identifying the cancer as forming GSK3α-positive puncta; and
   c. administering an asparaginase and an agent that inhibits GSK3α to a subject who has been identified as forming GSK3α-positive puncta.
2. A method of treating cancer, the method comprising:
   a. receiving the results of an assay that identifies a subject as having a cancer forming GSK3α-positive puncta; and
   b. administering an asparaginase and an agent that inhibits GSK3α to a subject who has been identified as forming GSK3α-positive puncta.
3. A method of treating asparaginase-resistant cancer, the method comprising:
   a. obtaining a biological sample from a subject having cancer;
   b. assaying the sample to identify for GSK3α-positive puncta;
   c. identifying a subject as having asparaginase-resistant cancer if the cancer forms GSK3α-positive puncta; and
   d. administering an asparaginase and an agent that inhibits GSK3α to a subject who has been identified as having asparaginase-resistant cancer.
4. A method of treating asparaginase-resistant cancer, the method comprising:
   a. receiving the results of an assay that identifies a subject as having a cancer forming GSK3α-positive puncta; and
   b. administering an asparaginase and an agent that inhibits GSK3α to a subject who has been identified as having asparaginase-resistant cancer.
5. The method of any of the preceding paragraphs, wherein the GSK3α-positive puncta are formed in response to asparagine starvation.
6. The method of any of the preceding paragraphs, wherein the GSK3α-positive puncta are formed following contact with an asparaginase treatment.

7. The method of any of the preceding paragraphs, wherein the assaying is treating the sample with an asparaginase, or culturing the sample in conditions of asparagine starvation or amino acid starvation.
8. The methods of any of the preceding paragraphs, wherein the cancer is selected from the list consisting of: a carcinoma, a melanoma, a sarcoma, a myeloma, a leukemia, and a lymphoma.
9. The methods of any of the preceding paragraphs, wherein the cancer is a solid tumor.
10. The method of any of the preceding paragraphs, wherein the leukemia is acute myeloid leukemia (AML), Chronic myeloid leukemia (CML), Acute lymphocytic leukemia (ALL), and Chronic lymphocytic leukemia (CLL).
11. The methods of any of the preceding paragraphs, wherein the cancer is a solid tumor.
12. The methods of any of the preceding paragraphs, wherein the cancer is colon or pancreatic cancer.
13. The methods of any of the preceding paragraphs, wherein the cancer is metastatic.
14. The method of any of the preceding paragraphs, wherein the biological sample is a biopsied sample, a tissue sample or a blood sample.
15. The method of any of the preceding paragraphs, wherein the biopsied sample is a tumor sample.
16. The methods of any of the preceding paragraphs, wherein the asparaginase is selected from the group consisting of: L-asparaginase (Elspar), pegaspargase (PEG-asparaginase; Oncaspar), SC-PEG asparaginase, Calaspargase pegol (Cal-PEG; SHP663), *Erwinia* asparaginase (Erwinaze), cristantaspase, and Asparaginase medac.
17. The methods of any of the preceding paragraphs, wherein the agent that inhibits GSK3α is selected from the group consisting of a small molecule, an antibody, a peptide, a genome editing system, an antisense oligonucleotide, and an RNAi.
18. The method of any of the preceding paragraphs, wherein the small molecule is selected from the group consisting of: BRD0705, BRD4963, BRD1652, BRD3731, CHIR-98014, LY2090314, AZD1080, CHIR-99021 (CT99021) HCl, CHIR-99021 (CT99021), BIO-acetoxime, SB216763, SB415286, Abemaciclib (LY2835210), AT-9283, RGB-286638, PHA-793887, AT-7519, AZD-5438, OTS-167, 9-ING-41, Tideglusib (NP031112), and AR-A014418.
19. The method of any of the preceding paragraphs, wherein the small molecule is BRD0705.
20. The method of any of the preceding paragraphs, wherein the RNAi is a microRNA, an siRNA, or a shRNA.
21. The methods of any of the preceding paragraphs, wherein inhibiting GSK3α is inhibiting the expression level and/or activity of GSK3α.
22. The method of any of the preceding paragraphs, wherein the expression level and/or activity of GSK3α is inhibited by at least 50%, at least 60%, at least 70%, at least 80%, at least 90%, or more as compared to an appropriate control.
23. The methods of any of the preceding paragraphs, wherein assaying is done by immunofluorescence or flow cytometry.
24. The methods of any of the preceding paragraphs, wherein the subject has previously been administered an anti-cancer therapy.
25. The methods of any of the preceding paragraphs, wherein the subject has not previously been administered an anti-cancer therapy.
26. A method of identifying a subject as having asparaginase-resistant cancer, the method comprising:
   a. obtaining a biological sample from a subject having cancer;
   b. assaying the sample to identify for GSK3α-positive puncta formation; and
   c. identifying a subject as having asparaginase-resistant cancer if the cancer has GSK3α-positive puncta.
27. A method of identifying a subject as having asparaginase-resistant cancer, the method comprising:
   a. receiving the results of an assay that identifies a subject as having a cancer forming GSK3α-positive puncta; and
   b. identifying a subject as having asparaginase-resistant cancer if the cancer has GSK3α-positive puncta.
28. The method of any of the preceding paragraphs, wherein the GSK3α-positive puncta are formed in response to asparagine starvation.
29. The method of any of the preceding paragraphs, wherein the GSK3α-positive puncta are formed following contact with an asparaginase treatment.
30. The method of any of the preceding paragraphs, wherein the assaying is treating the sample with an asparaginase, or culturing the sample in conditions of asparagine starvation or amino acid starvation.
31. A method of treating cancer, the method comprising:
   a. obtaining a biological tumor sample from a subject having cancer;
   b. assaying the sample by treating with an asparaginase, or culturing in conditions of asparagine starvation or amino acid starvation
   c. identifying the sample as forming GSK3α-positive puncta in response to asparagine starvation; and
   d. administering an asparaginase and an agent that inhibits GSK3α to a subject who has been identified as having a sample that forms GSK3α-positive puncta.
32. A method of treating cancer, the method comprising:
   a. receiving the results of an assay that identifies a subject as having a cancer that forms GSK3α-positive puncta in response to asparaginase treatment or asparagine starvation; and
   b. administering an asparaginase and an agent that inhibits GSK3α to a subject who has been identified as having a cancer that forms GSK3α-positive puncta in response to asparagine starvation.
33. A method of treating asparaginase-resistant cancer, the method comprising:
   a. obtaining a biological sample from a subject having cancer;
   b. assaying the sample to identify formation of GSK3α-positive puncta in response to asparaginase treatment or asparagine starvation;
   c. identifying a subject as having asparaginase-resistant cancer if the cancer forms GSK3α-positive puncta in response to asparagine starvation; and
   d. administering an asparaginase and an agent that inhibits GSK3α to a subject who has been identified as having asparaginase-resistant cancer.
34. A method of treating asparaginase-resistant cancer, the method comprising:
   a. receiving the results of an assay that identifies a subject as having a cancer that forms GSK3α-positive puncta in response to asparaginase treatment or asparagine starvation; and b. administering an asparaginase and an agent that inhibits GSK3α to a subject who has been identified as having asparaginase-resistant cancer.

35. A method of identifying a subject as having asparaginase-resistant cancer, the method comprising:

a. obtaining a biological sample from a subject having cancer;

b. treating the sample with asparaginase, or asparagine starvation, or amino acid starvation;

c. assaying the sample to identify formation of GSK3α-positive puncta; and d. identifying a subject as having asparaginase-resistant cancer if the sample forms GSK3α-positive puncta.

EXAMPLES

Example 1

Asparaginase is an antileukemic enzyme that depletes the nonessential amino acid asparagine, but resistance is a common clinical problem whose biologic basis is poorly understood. The inventors recently found that Wnt-induced inhibition of glycogen synthase kinase 3 (GSK3) profoundly sensitizes drug-resistant leukemias to asparaginase (Hinze et al, Cancer Cell, 2019; 35:664) and U.S. patent application Ser. No. 12/271,629, which are incorporated herein by reference in its entireties. This effect is mediated by a β-catenin independent branch of Wnt signaling termed Wnt-dependent stabilization of proteins (Wnt/STOP), which inhibits GSK3-dependent protein ubiquitination and proteasomal degradation (Acebron et al, Mol Cell, 2014; 54:663). Thus, asparaginase-resistant leukemias rely on catabolic protein degradation as an alternative source of amino acids to survive asparaginase therapy. Asparaginase resistance is selectively mediated by GSK3α, because its genetic or pharmacologic inhibition fully phenocopied Wnt-induced sensitization to asparaginase ($p<0.0001$), whereas selective inhibition of GSK3β had no effect. This is surprising because GSK3α and GSK3β are closely related paralogs thought to be redundant for many of their biologic functions. Thus, work presented herein defines how asparaginase resistance is selectively dependent on GSK3α activity.

To define the GSK3 domains responsible for asparaginase resistance, the inventors leveraged the fact that selective depletion of GSK3α induces profound sensitization to asparaginase, and this effect is rescued by expression of a cDNA encoding GSK3α, but not GSK3β. They thus tested whether asparaginase resistance could be restored by expression of a series of GSK3 alleles in which the N-terminal, kinase, and C-terminal domains of GSK3α and GSK3β were swapped in various configurations. This revealed that asparaginase resistance is dependent on the N-terminal domain of GSK3α, whereas the kinase and the C-terminal domain were interchangeable. Fusing the N-terminus of GSK3α to the kinase and C-terminal domains of GSK3β fully restored asparaginase resistance in GSK3α depleted T-ALL ($p<0.0001$) and AML cells ($p<0.0001$). By contrast, fusing the N-terminus of GSK3β to the kinase and C-terminus of GSK3α had no discernible effect on response to asparaginase (p=n.s.). To investigate how the N-terminus of GSK3α regulates asparaginase response, structural prediction algorithms were applied. This revealed that the N-terminal domain of GSK3α is a low-complexity (or prion-like) domain predicted to be intrinsically disordered, features associated with liquid-liquid phase separation. Phase separation is an increasingly recognized feature of cell biology that allows cells to concentrate components of important biochemical reactions in so-called membraneless organelles, thus promoting high-catalytic efficiency. Indeed, immunofluorescence confocal microscopy revealed that GSK3α, but not GSK3β, translocates into cytoplasmic bodies in response to asparagine depletion ($p<0.0001$). The cytoplasmic GSK3α bodies were membraneless, as assessed by a proteinase K protection assay, and appeared to be distinct from known phase-separated compartments such as stress granules, P-bodies and aggresomes. However, cytoplasmic GSK3α bodies colocalized with the heat shock protein 70 (HSP70), K48-linked ubiquitin and the proteasome, suggesting that these bodies function in protein unfolding, ubiquitination and degradation. Indeed, genetic depletion of either GSK3α or HSP70 blocked formation of phase-separated GSK3α bodies ($p<0.0001$) and induced asparaginase sensitivity ($p<0.0001$).

Figure 1:
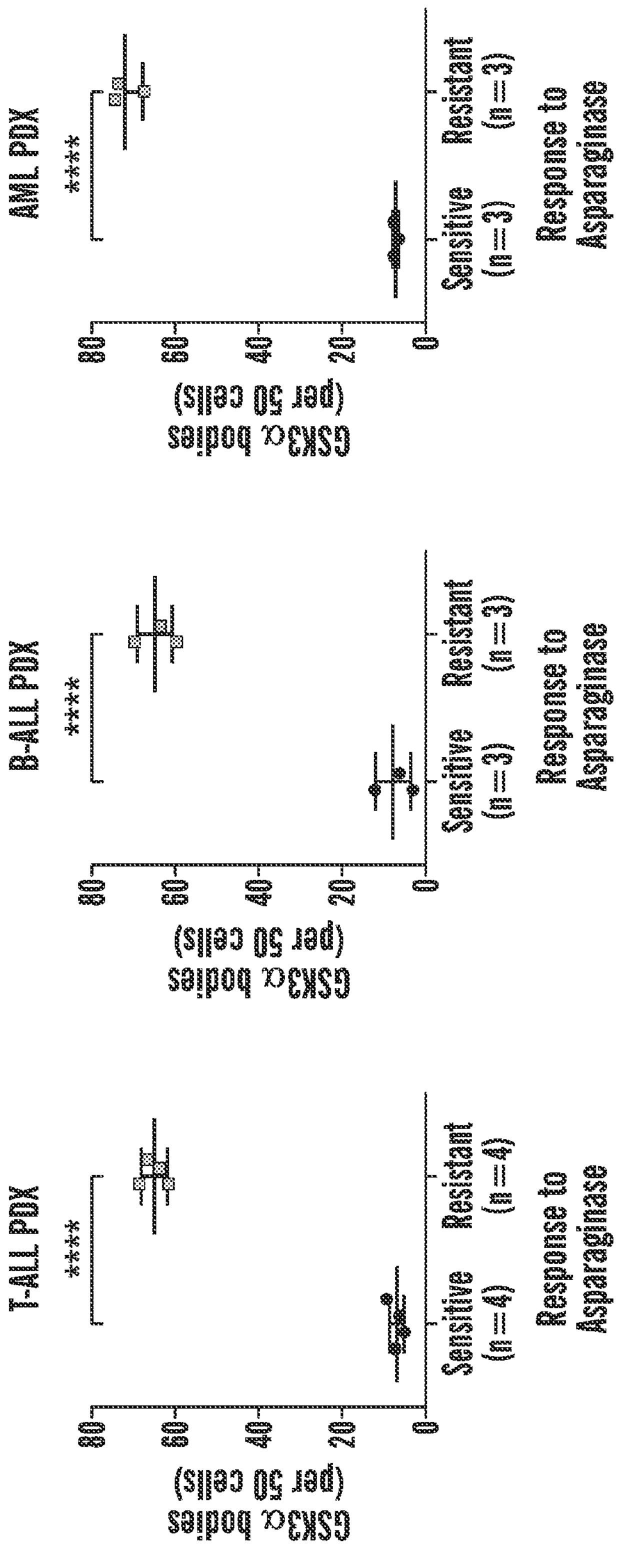

To explore the clinical relevance of GSK3α body formation in response to asparagine starvation, a panel of matched asparaginase resistant vs. sensitive T-ALL, AML and B-ALL patient-derived xenografts (PDXs) were tested, and found that the ability of GSK3α to undergo phase separation significantly correlated with resistance to asparaginase in T-ALL, B-ALL and AML (FIG. 1, $p<0.0001$).

Data presented herein support a model in which inducible phase separation of GSK3α and heat shock proteins represents a previously unrecognized response to amino acid starvation that concentrates the cellular machinery for protein degradation, thus allowing efficient catalysis of this alternative source of amino acids in response to amino acid starvation.

Example 2

Asparaginase is a therapeutic enzyme that has long been known to kill leukemia cells by depleting the amino acid asparagine, but the development of resistance is a major clinical problem with a poor prognosis. Asparaginase has no known activity in colorectal cancer. The inventors previously found that drugs or mutations that block function of the kinase GSK3α induce profound sensitization to asparaginase in acute leukemias and colorectal cancers that are resistant to monotherapy with asparaginasc.

Figure 2:
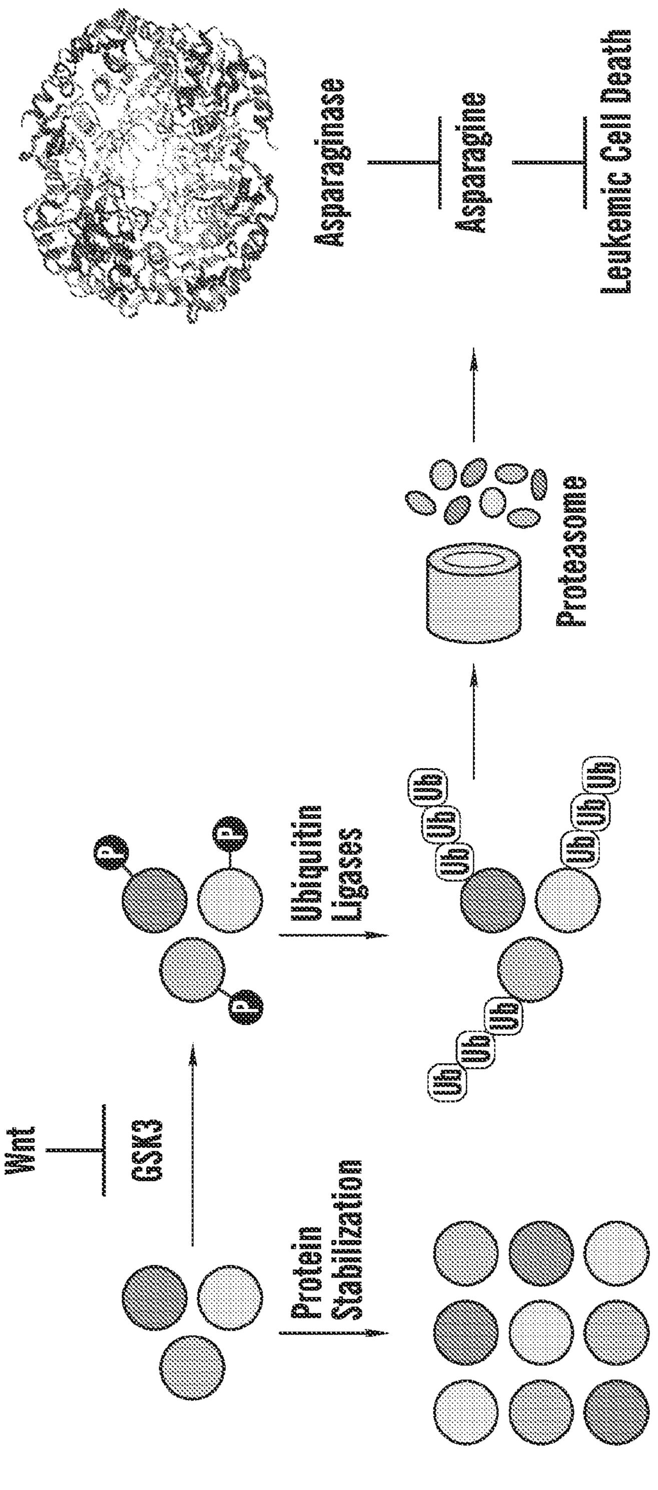

Blocking the function of GSK3α induces asparaginase sensitivity because, in response to asparagine starvation (which is how asparaginase kills leukemia cells), cells activate degradation of their own proteins to release free amino acids, thus allowing cells to replenish their intracellular stores of asparagine and survive during asparaginase therapy (FIG. 2). This adaptive response to asparagine starvation is absolutely dependent on the function of GSK3α.

The current invention involves the discovery that activating protein degradation in response to asparaginase therapy involves the physical re-localization of GSK3α from its diffuse cytoplasmic localization at baseline into GSK3α-positive cytoplasmic puncta (e.g., GSK3α bodies), and that formation of these bodies is a biomarker of response to asparaginase in combination with a drug that inhibits GSK3α function. Therefore, formation of GSK3α bodies after short-term treatment of human tumor specimens with asparaginase represents a prognostic biomarker that will allow patient selection for therapy with the combination of asparaginase and a GSK3α inhibitor. GSK3α bodies can be readily visualized by immunofluorescence microscopy of asparaginase-treated cells. While this requires ex vivo treatment of primary human tumor specimens, exemplary methods for are applying biomarkers involving similar short-term ex vivo treatment of human tumors, e.g., are further described in international application WO 2018/081830, which is incorporated herein by reference in its entirety. The methods described herein would differ from the methods of international application WO 2018/081830 however, as the endpoint of the assay in this instant application is microscopy-based.

We discovered GSK3α body formation by trying to understand our previous discovery that asparaginase resistance is solely dependent on GSK3α, and not its closely related homolog GSK3α (Hinze et al., 2019). The enzymatic domains of GSK3α and GSK3β are highly conserved, but the C- and N-termini of these enzymes are not well conserved. Using domain-swap experiments, we found that asparaginase resistance uniquely requires the N-terminal domain of GSK3α, whereas the enzymatic (kinase) and C-terminal domains of GSK3α and GSK3β are interchangeable (FIG. 3). The N-terminus of GSK3α does not appear to be related to any other protein domain, but domain prediction algorithms predict that this is a low-complexity domain highly enriched in small polar amino acids (FIG. 3), features associated with liquid-liquid phase separation behavior.

Figure 4A:
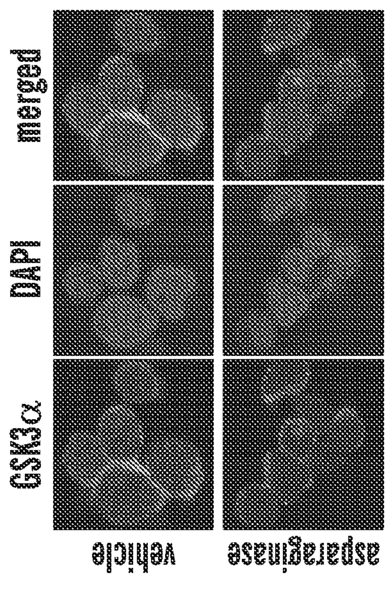
Figure 4B:
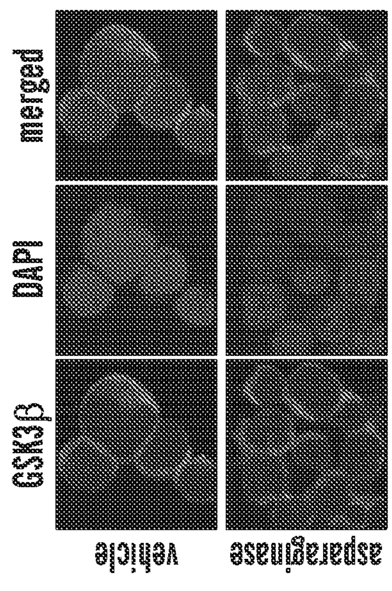
Figure 4C:
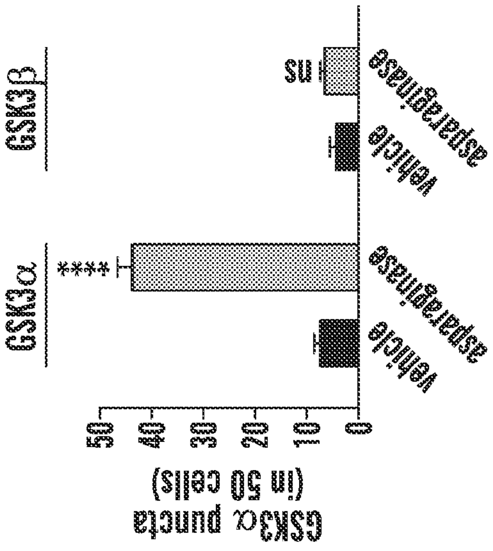
Figure 4D:
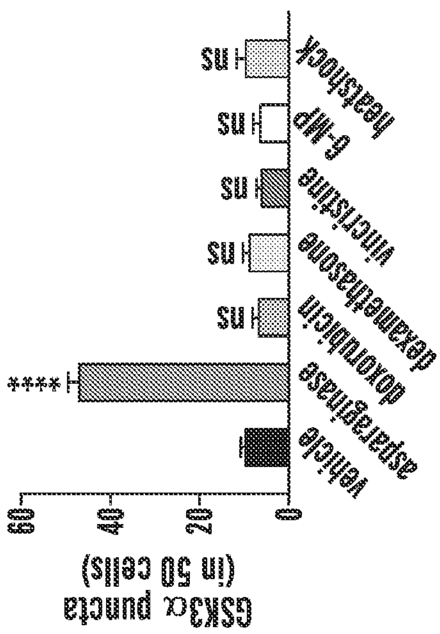
Figure 5:
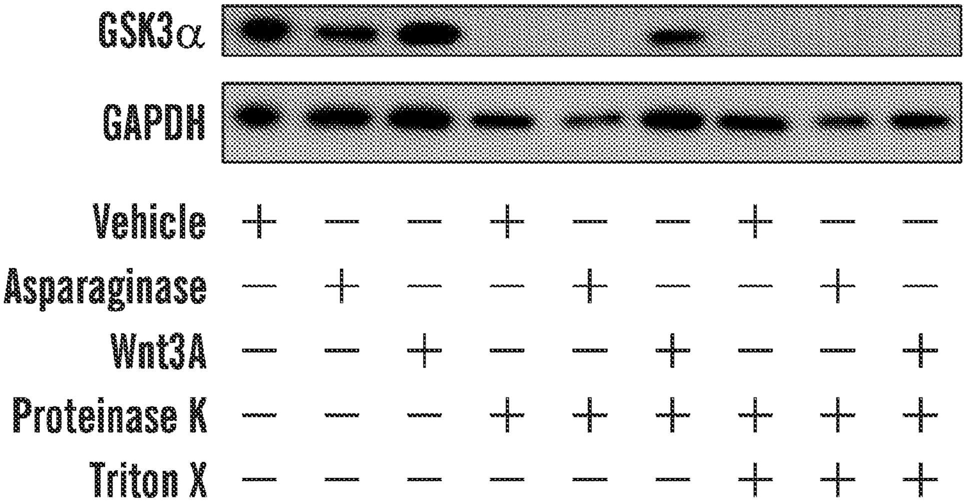

Liquid-liquid phase separation (or phase separation) is an increasingly recognized feature of cellular biology that allows cells to concentrate key components of specific biochemical reactions in so-called membraneless organelles, in order to promote catalysis of specific biochemical reactions. We thus determined whether GSK3α liquid-liquid phase separation might play a role in asparaginase resistance. Indeed, we found that asparagine starvation induces phase separation of GSK3α (and not GSK3β) into cytoplasmic puncta (which we call GSK3α bodies) (FIG. 4). This effect is uniquely dependent on the N-terminal domain of GSK3α because GSK3β does not undergo phase separation unless its N-terminus is swapped with that of GSK3α. We also confirmed that GSK3α bodies are membraneless cellular compartments based on proteinase protection assays (FIG. 5). Formation of GSK3α bodies reflects the fact that cells are activating GSK3α-dependent protein degradation by concentrating GSK3α together with other core components of the cellular machinery for protein ubiquitination and proteasomal degradation, in order to allow protein degradation to proceed at maximal catalytic efficiency in response to amino acid starvation.

Figure 6A:
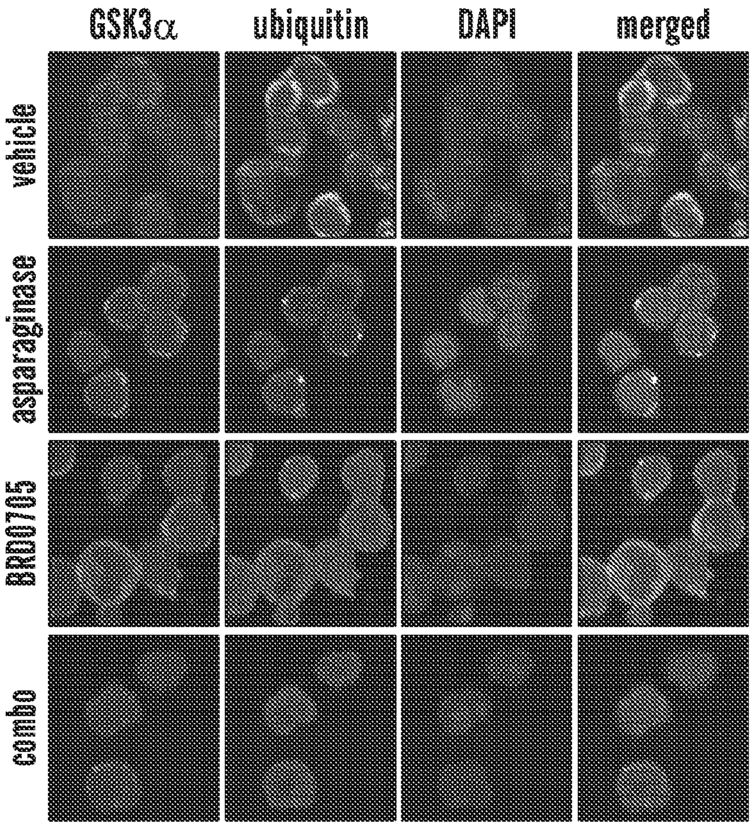
Figure 6B:
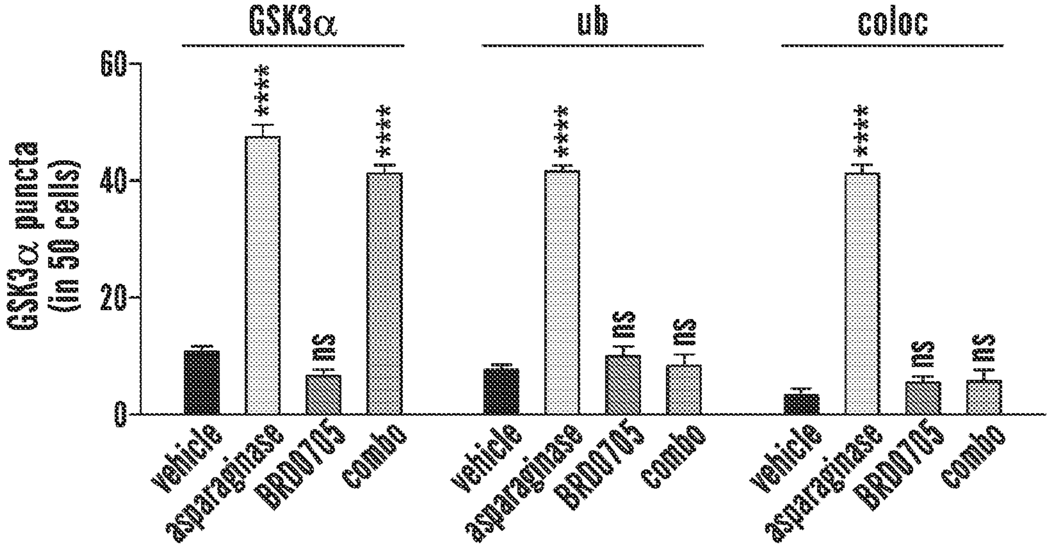
Figure 7A:
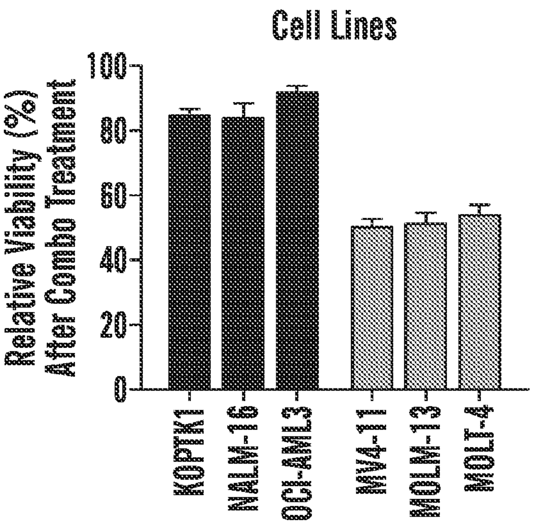
Figure 7B:
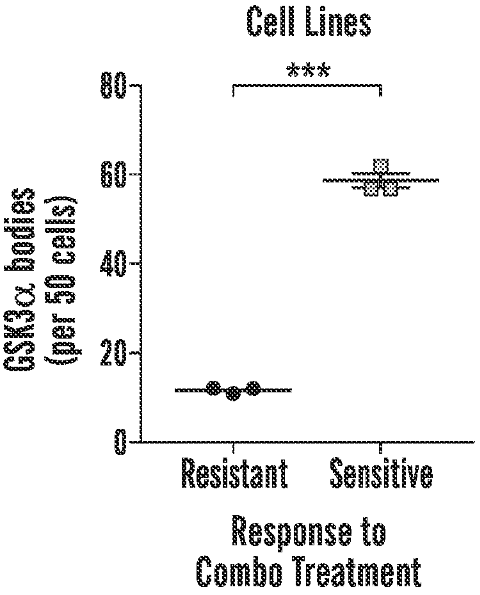
Figure 7C:
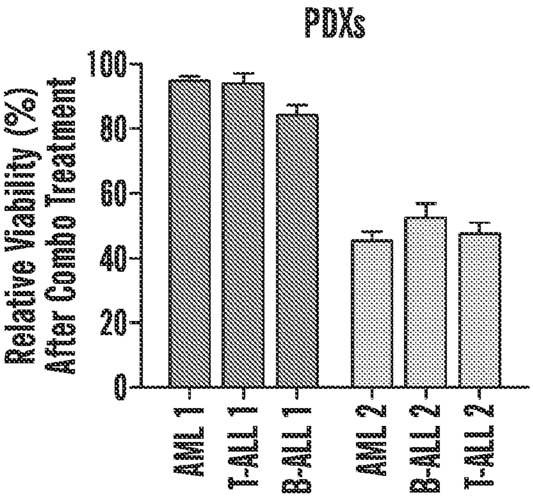
Figure 7D:
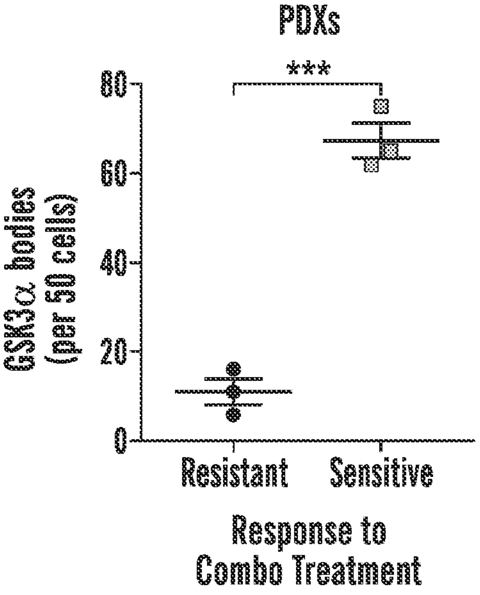

Formation of GSK3α bodies reflects the fact that cells are activating GSK3α-dependent protein degradation by concentrating GSK3α together with other key components of the cellular machinery for protein ubiquitination and proteasomal degradation, in order to maximize efficiency of this biochemical reaction in response to asparaginase starvation. Indeed, we found that GSK3α bodies function to ubiquitinate proteins, which marks target proteins for proteasomal degradation, in a manner dependent on the enzymatic activity of GSK3α (FIG. 6).

Data presented herein has shown that formation of these GSK3α bodies correlates with resistance to asparaginase monotherapy (FIG. 1), but predicts response to the combination of GSK3α and asparaginase (FIG. 7). Thus, this invention will provide an ideal companion diagnostic for patient selection for therapy with asparaginase combined with a GSK3α inhibitor. There are no other ways to identify patients who will respond to the combination of GSK3α inhibition and asparaginase.

REFERENCES

Hinze, L., Pfirrmann, M., Karim, S., Degar, J., McGuckin, C., Vinjamur, D., Sacher, J., Stevenson, K. E., Neuberg, D. S., Orellana, E., et al. (2019). Synthetic Lethality of Wnt Pathway Activation and Asparaginase in Drug-Resistant Acute Leukemias. Cancer Cell 35, 664-676 e667.

Huang, Y. J., Acton, T. B., and Montelione, G. T. (2014). DisMeta: a meta server for construct design and optimization. Methods Mol Biol 1091, 3-16.

Taelman, V. F., Dobrowolski, R., Plouhinec, J. L., Fuentealba, L. C., Vorwald, P. P., Gumper, I., Sabatini, D. D., and De Robertis, E. M. (2010). Wnt signaling requires sequestration of glycogen synthase kinase 3 inside multivesicular endosomes. Cell 143, 1136-1148.

Example 3

Introduction

The ability to maintain amino acid homeostasis despite a variable supply of extracellular nutrients is central to cellular fitness across environmental conditions. In eukaryotic cells, amino acid starvation inhibits mTORC1 and activates GCN2 to orchestrate a network of adaptive responses. These include inhibition of protein synthesis to reduce amino acid consumption, upregulation of amino acid biosynthesis and transport, and increased generation of amino acids from lysosomal protein degradation by stimulating both autophagy and pinocytosis (1-5). However, increasing amino acid biogenesis and import cannot rescue cells from starvation of amino acids they are unable to synthesize. Moreover, some tissues such as the brain are unable to efficiently induce autophagy as a catabolic amino acid source during starvation (6). Proteasomal protein degradation is an alternative catabolic source of amino acids that accounts for the majority of basal protein degradation in mammalian cells (7, 8). While several studies have linked proteasomal function to the maintenance of amino acid homeostasis (9-11), the cellular and molecular mechanisms linking amino acid starvation to induction of proteasomal protein degradation are unknown.

Mammals have two paralogs of glycogen synthase kinase 3, GSK3α and GSK3β (also known as GSK3A and GSK3B) that are largely redundant and ubiquitously expressed (12). However, GSK3β has received the bulk of the attention in the literature, in part because it is the only mammalian GSK3 paralog that can rescue embryonic development in GSK3-deficient *drosophila* (13, 14). A number of studies leveraging GSK3α-deficient mice have implicated a preferential role for this GSK3 paralog in diverse so-called cardiometabolic functions [reviewed in (15)]. However, the molecular basis for the paralog-selective effects of GSK3 proteins remain poorly understood.

The inventors identified that activation of Wnt-dependent stabilization of proteins (Wnt/STOP), a β-catenin independent branch of Wnt signaling that inhibits GSK3-dependent protein degradation (16), induces a profound therapeutic vulnerability to asparagine depletion in acute leukemias and in colorectal cancer (17, 18). GSK3 can phosphorylate a large fraction of cellular proteins to form a phosphodegron that marks proteins for ubiquitination and proteasomal degradation, and Wnt-induced inhibition of GSK3 prolongs total cellular protein half-life and increases cell size (16, 19-21). The inventors also found that Wnt-induced asparaginase sensitization is uniquely dependent on GSK3α (17, 18), because GSK3β fully compensates for loss of GSK3a in canonical Wnt/β-catenin signaling (22-25). Using domain-swap experiments, the inventors show herein that resistance to asparagine starvation is selectively dependent on an N-terminal low-complexity domain unique to GSK3α. This domain mediates spatial sequestration of GSK3α and the ubiquitin proteasome system in response to amino acid starvation. It is specifically contemplated herein that GSK3α body formation provides a cellular mechanism to stimulate proteasomal protein degradation as a catabolic source of amino acids during starvation.

Results

Figure 3A:
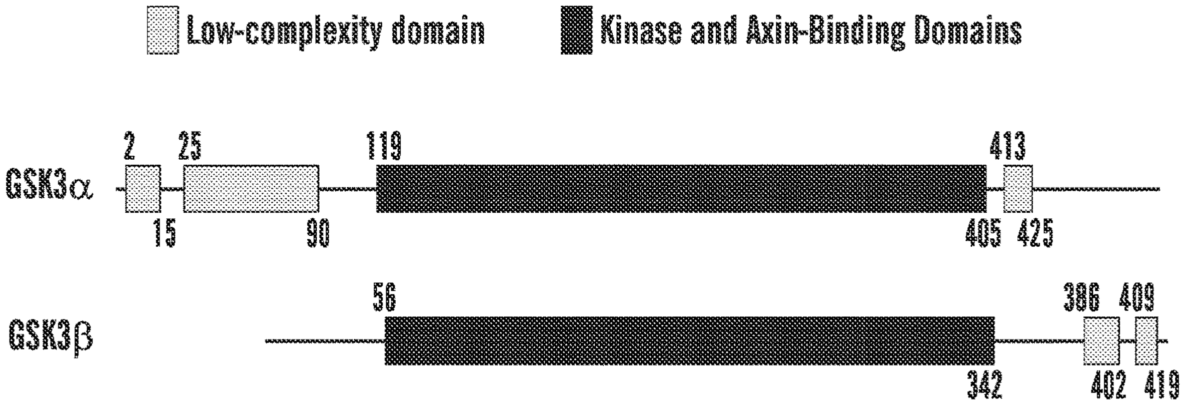
Figure 3B:
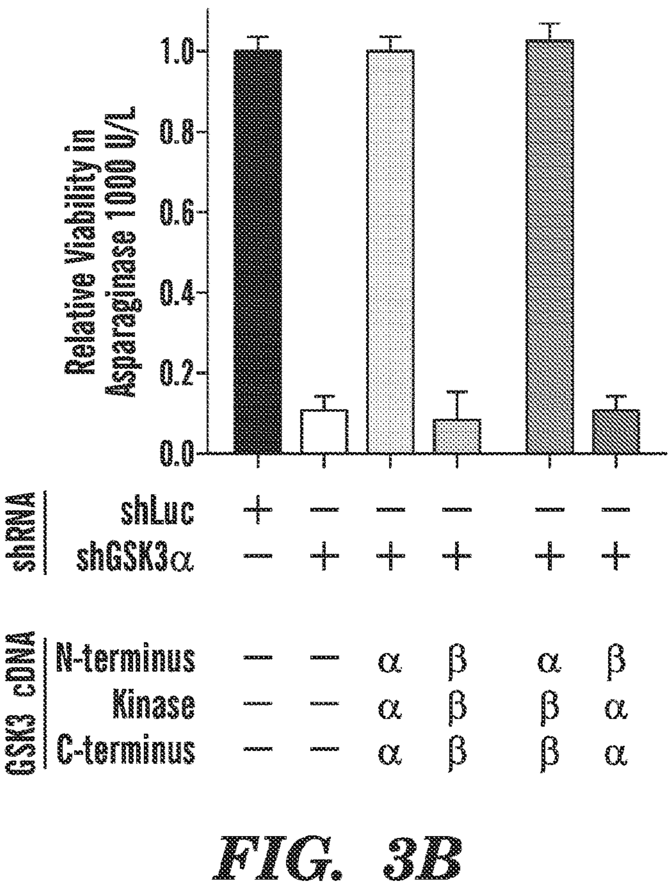
Figure 10:
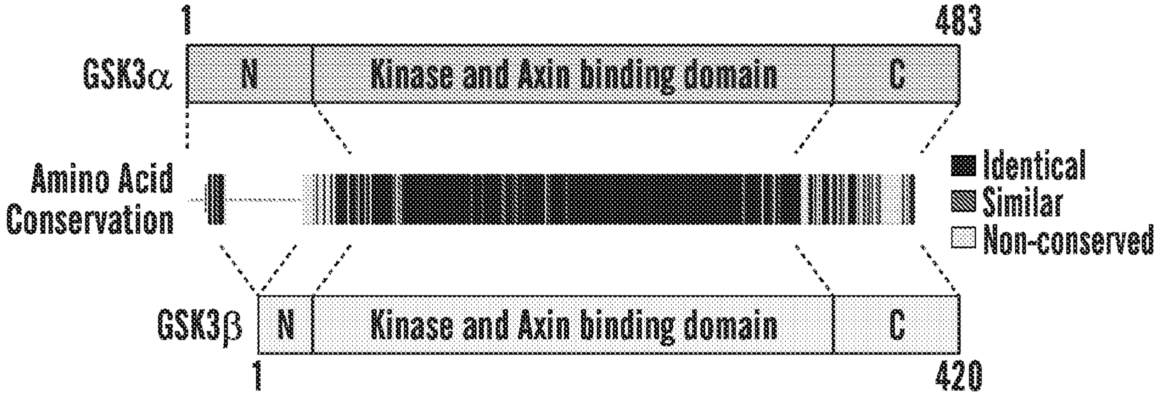
FIG. 10 shows a schematic of domains and conserved regions of GSKα and GSKβ.
Figure 11:
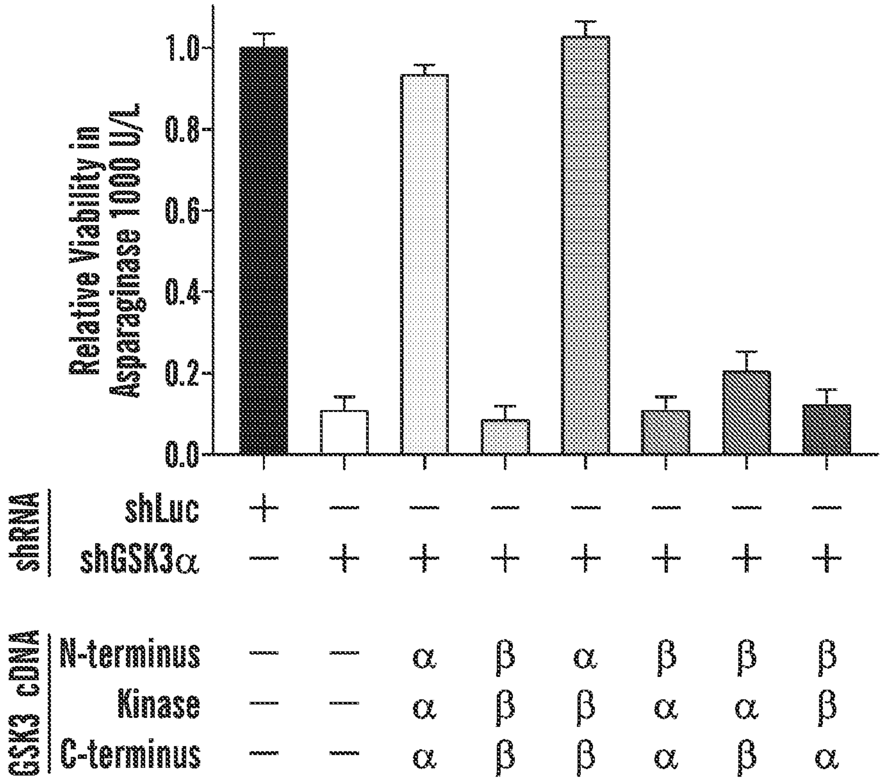
FIG. 11 shows relative viability in asparaginase under the indicated conditions.

Asparagine starvation triggers spatial sequestration of GSK3α in a manner dependent on its N-terminal low-complexity domain To define why asparaginase resistance is uniquely dependent on GSKα and not GSK3β, domain-swap approach was applied. The kinase domains of these paralogs are highly homologous, but their N- and C-termini have diverged (FIG. 10). Depletion of GSK3α using RNA interference induced asparaginase sensitivity in Jurkat T-cell leukemia cells, an effect rescued by transduction of full-length GSK3α, but not GSK3β (FIG. 3B). Expressing a fusion construct encoding the N-terminus of GSK3α fused to the kinase and C-termini of GSK3β completely restored asparaginase resistance (FIG. 3B). By contrast, fusing the N-terminus of GSK3β to the kinase and C-termini of GSK3α disabled its ability to mediate asparaginase resistance. Thus, asparaginase resistance is uniquely dependent on the N-terminus of GSK3α, whereas the kinase domains are interchangeable.

The N-terminus of GSK3α has been highly conserved through mammalian evolution (FIG. S2), strongly suggesting positive selection. Surprisingly, neither BLAST nor PROSITE analysis (26, 27) revealed detectable homology to any other proteins or known protein domains. However, DisMeta prediction (28) revealed that much of the N-terminus of GSK3α is low-complexity by SEG analysis, indicating an amino acid composition significantly less complex than predicted by chance (FIG. 3A). Indeed, this domain is highly enriched in glycines, as well as serines and prolines (FIG. 3C). Such features have been associated with intrinsically disordered domains that mediate biomolecular condensation, which can promote the catalytic efficiency of specific biochemical reactions by concentrating their key factors in so-called membraneless organelles (29, 30).

To test whether GSK3α undergoes spatial sequestration in response to asparaginase, we applied immunofluorescence using paralog-selective antibodies (FIG. S4). We found that the GSK3α protein was broadly distributed at baseline, but asparaginase treatment triggered its condensation into distinct cytoplasmic puncta, which we termed GSK3α bodies (FIG. 4A). By contrast, GSK3β remained broadly distributed regardless of asparaginase therapy (FIGS. 4A and 4B), unless its N-terminus was swapped with that of GSK3α (FIG. S6).

Figure 8:
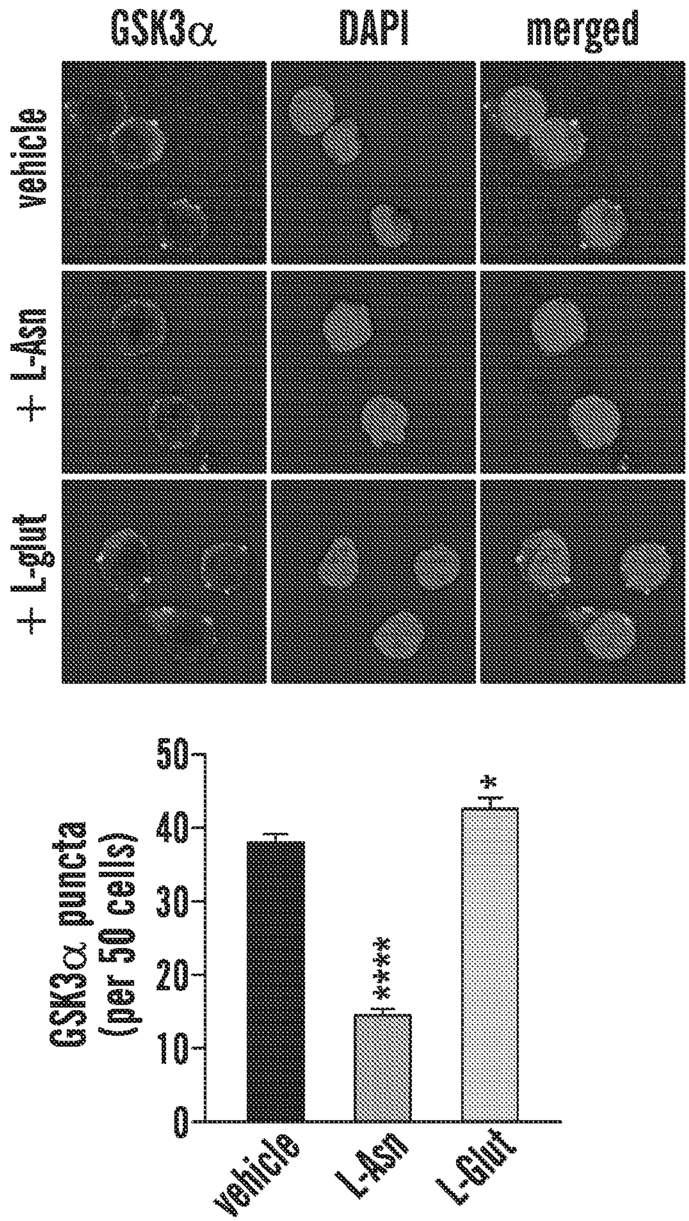
Figure 12:
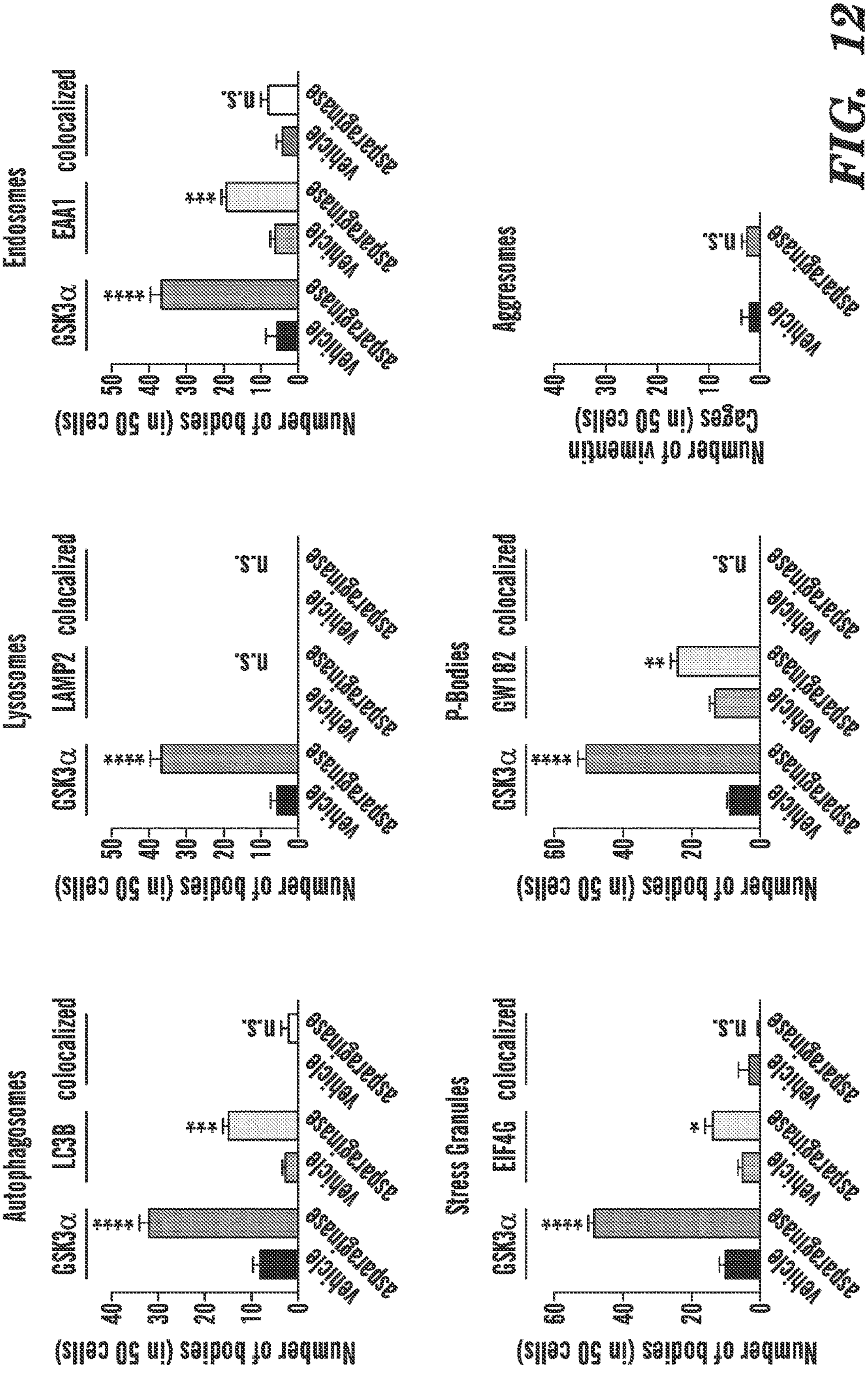
FIG. 12 shows co-localization of GSKα and various markers of known cellular bodies, e.g., autophagosomes, lysosomes, endosomes, stress granules, P-bodies, and aggresomes.
Figure 13:
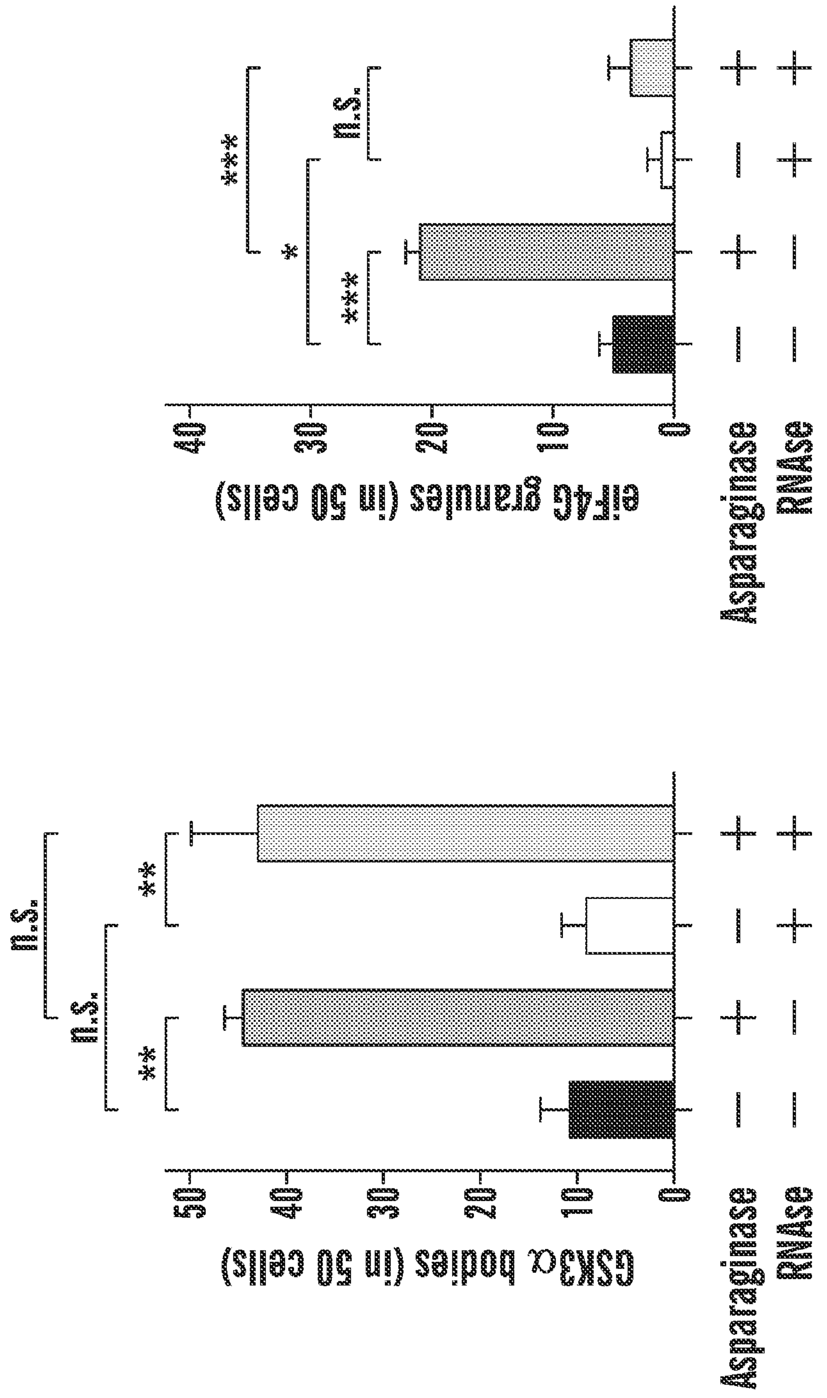
FIG. 13 shows the quantity of GSK3α-positive cytoplasmic bodies and eiF4G-positive cytoplasmic bodies formed in the presence of asparaginase under the indicated conditions.

It was found that GSK3α body formation was a specific response to asparaginase among a panel of antileukemic drugs (FIG. 4D), arguing against a nonspecific cytotoxic response. Moreover, culturing these cells in media that was deficient of all nonessential amino acids was sufficient to trigger GSK3α body formation, and this effect was blocked by replenishing asparagine alone, but not the physiochemically similar amino acid glutamine (FIG. 8). It was sought to determine whether GSK3α body formation might reflect its accumulation inside membrane-bound compartments as part of a starvation response, but found no significant co-staining of GSK3α bodies with established markers of autophagosomes, lysosomes or endosomes (FIG. 12).

It was then determined whether GSK3α bodies are membraneless using the proteinase K protection assay. Jurkat cells were treated with vehicle or asparaginase to trigger GSK3α body formation. As a positive control, treatment with Wnt3A was included, which triggers sequestration of GSK3 inside membrane-bound multivesicular endosomes (19). Following cytoplasmic membrane permeabilization with digitonin, cells were treated with proteinase K, and GSK3α protein levels were assessed by Western blot analysis. This revealed that GSK3α remained accessible to proteinase K digestion at baseline and in asparaginase-treated cells. By contrast, GSK3α was protected from protease digestion by treatment with Wnt3A, unless all membranes were permeabilized using Triton X-100 (FIG. 5). These findings indicate that GSK3α bodies are membraneless. No evidence was found to indicate that GSK3α accumulates in known membraneless cytoplasmic compartments, including stress granules, P-bodies or aggresomes, based on lack of co-staining with established markers (FIG. 12).

To test whether the N-terminus of GSK3α is sufficient to trigger spatial sequestration of a heterologous protein, expression constructs encoding the N-terminus of GSK3α fused to HaloTag were generated, which allows for covalent labeling and visualization of its fusion protein in live cells (31). The N-terminus of GSK3β was used as a negative control. Jurkat cells were transduced with these constructs, treated with vehicle or asparaginase, and we assessed HaloTag localization using its fluorescent ligand Oregon Green. This revealed that the N-terminus of GSK3α, but not GSK3β, was sufficient to drive HaloTag into cytoplasmic bodies in response to asparaginase therapy (FIG. S9).

Asparagine Depletion Triggers Spatial Sequestration of GSK3α with the Ubiquitin Proteasome System The inventors' prior studies linking Wnt-induced inhibition of GSK3 to asparaginase sensitivity demonstrated that drug-resistant cancers tolerate asparaginase by relying on protein degradation through the ubiquitin proteasome system (17, 18). It was sought was to determine whether GSK3α body formation might provide a cellular mechanism to maximize the catalytic efficiency of proteasomal protein degradation by concentrating GSK3α and the ubiquitin proteasome system in response to amino acid starvation. Indeed, immunofluorescence analysis revealed that GSK3α bodies co-localized with ubiquitin (FIG. 6A), which marks proteins for proteasomal degradation (8). Treatment with the ATP-competitive GSK3α inhibitor BRD0705 (24) did not block the ability of GSK3α to undergo biomolecular condensation in response to asparaginase, but did prevent accumulation of ubiquitin in GSK3α bodies (FIGS. 6A and 6B), indicating that GSK3α bodies function in protein ubiquitination. GSK3α bodies also co-localized with the proteasome, as assessed by immunofluorescence for the proteasomal subunit PSMA4 (FIGS. 20A and 20B).

Figure 14:
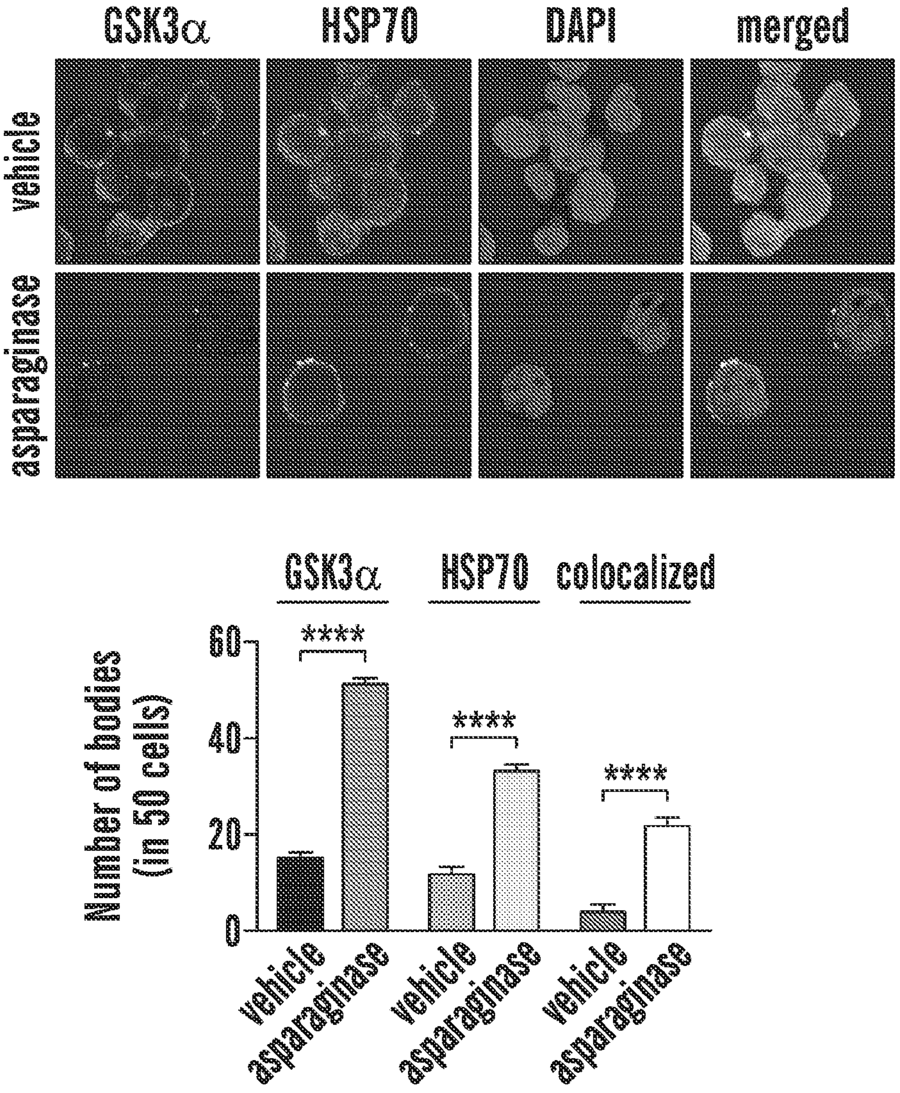
FIG. 14 shows co-localization of GSKα and HSP70 in cytoplasmic bodies formed in the presence of asparaginase.
Figure 15:
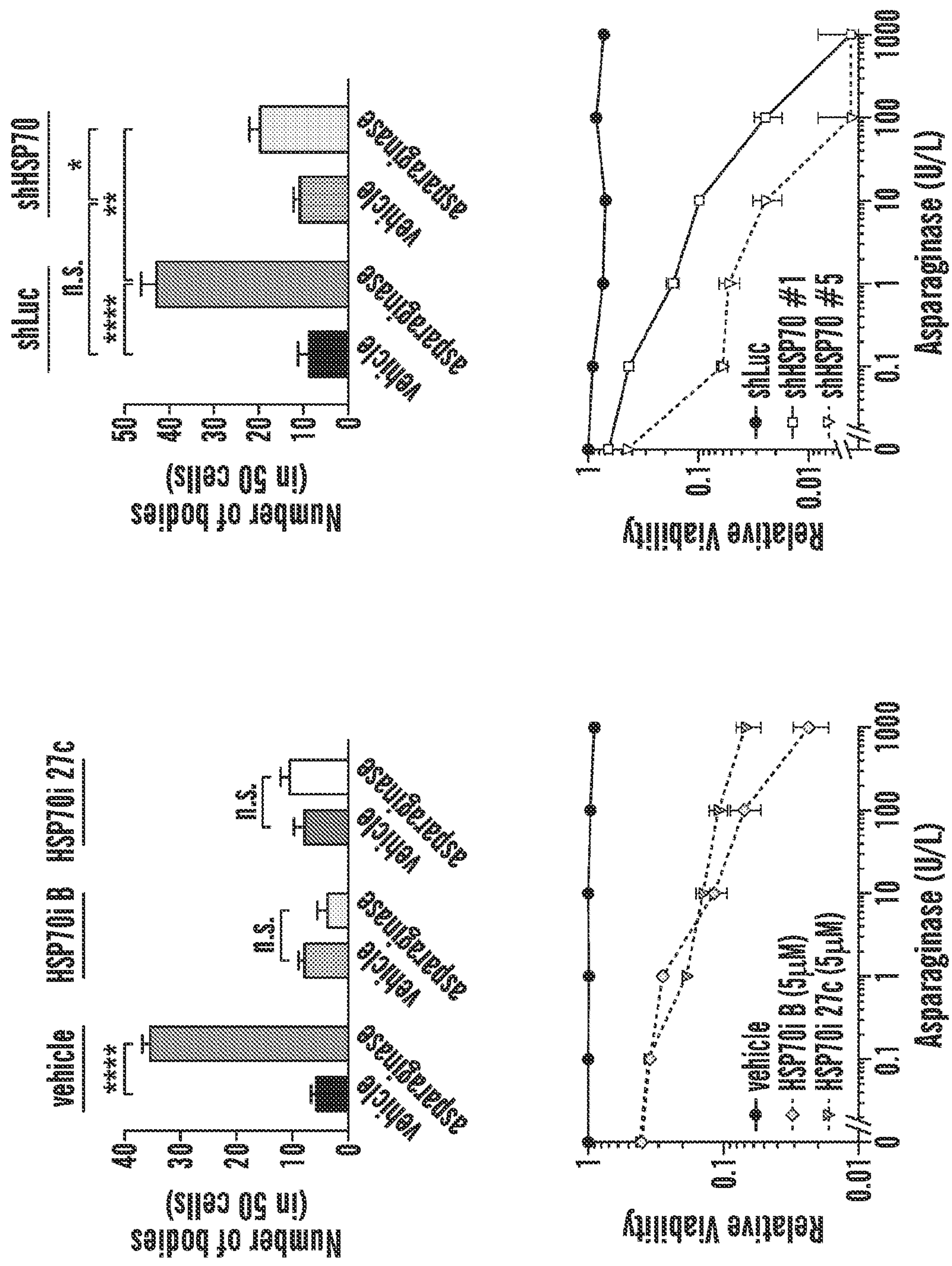
FIG. 15 shows that the quantity of cytoplasmic bodies formed in the presence of asparaginase is markedly reduced when HSP70 is additionally inhibited.

Heat shock proteins are required for degradation of misfolded proteins in some biomolecular condensates (32). Indeed, it was found that GSK3α bodies often co-localized with HSP70 (FIG. 14) and to a lesser degree HSP90, but not HSC70 or HSP40 (FIG. S11, A-F). Inhibition of HSP70 using two structurally unrelated allosteric inhibitors (33, 34) blocked both GSK3α body formation and asparaginase resistance, and this effect was phenocopied by HSP70-targeting shRNAs (FIG. 15). By contrast, inhibition of HSP90 had a subtle effect on GSK3α body formation, and no effect on asparaginase resistance (FIGS. S11, G and H). Thus, the enzymatic activity of HSP70 is required for GSK3α body formation.

GSK3α Promotes Survival During Starvation of Essential Amino Acids

It was then sought to determine if GSK3α body formation was stimulated by mTORC1 inhibition or GCN2 activation, which mediate the best-known responses to amino acid starvation (1, 3). However, inhibition or cither mTORC1 or GCN2 was insufficient to trigger GSK3α body formation, and did not block asparaginase-induced GSK3α body formation (FIG. S12).

Figure 16:
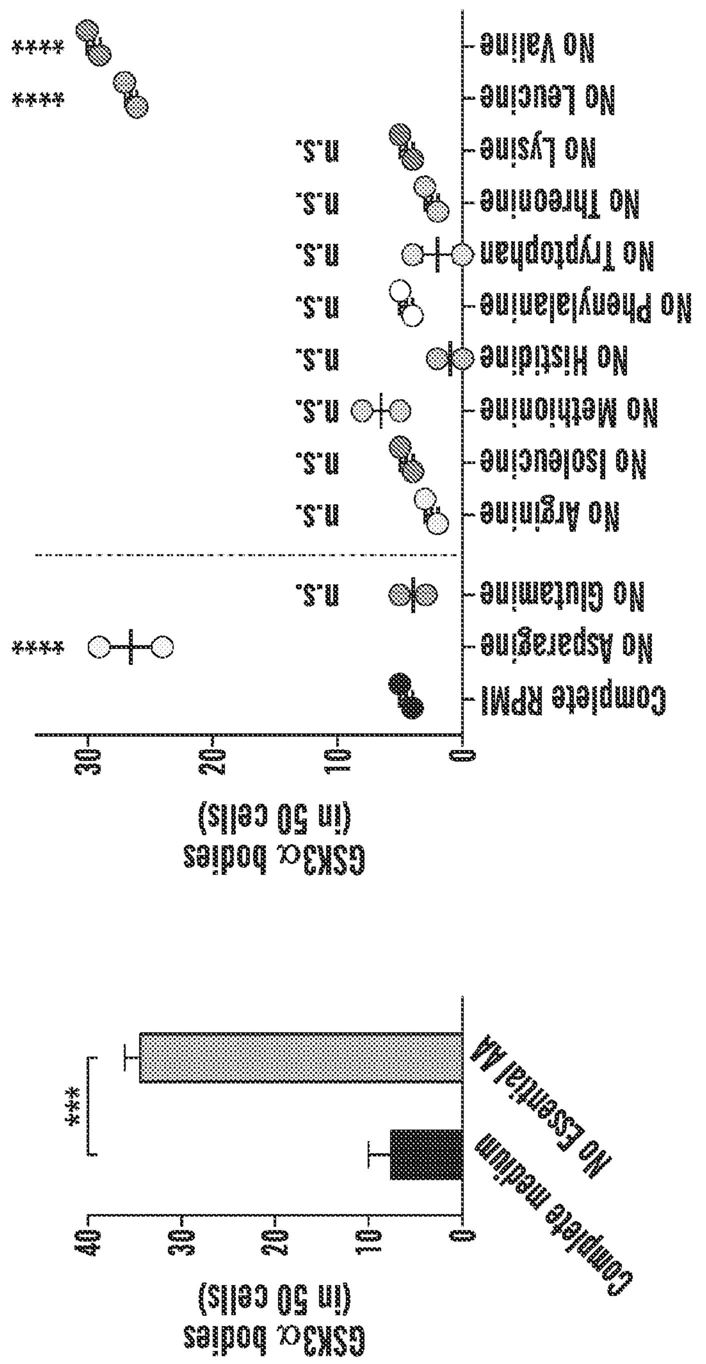
FIG. 16 shows the quantity of cytoplasmic bodies formed in media missing the indicated amino acids.

The studies presented herein above indicated that depletion of asparagine was unique among nonessential amino acids in its ability to trigger GSK3α body formation (FIG. 8). However, proteasomal protein degradation is a catabolic source of all proteinogenic amino acids, thus it might be evolutionarily advantageous for such a response to be triggered by depletion of essential amino acids, which cannot be synthesized by mammalian cells. Indeed, culturing Jurkat cells in medium depleted only of essential amino acids was sufficient to trigger GSK3α body formation (FIG. 16). Individual essential amino acid depletion experiments revealed that formation of GSK3α bodies was a unique response to individual depletion of leucine or valine, in addition to asparagine (FIG. 16). By contrast, individual depletion of any other essential amino acid was insufficient to trigger this response. It was noted that while leucine deficiency is known to be sensed directly to inhibit mTORC1 activity via the Rag GTPase pathway (35), neither valine nor asparagine are known to have direct sensors in this pathway. Moreover, depletion of methionine and arginine, which are sensed by this pathway to inhibit mTORC1 (36, 37), failed to trigger GSK3α body formation (FIG. 16). These findings strengthen the argument that GSK3α body formation is regulated by mechanisms distinct from those that couple amino acid availability to mTORC1.

Figure 17:
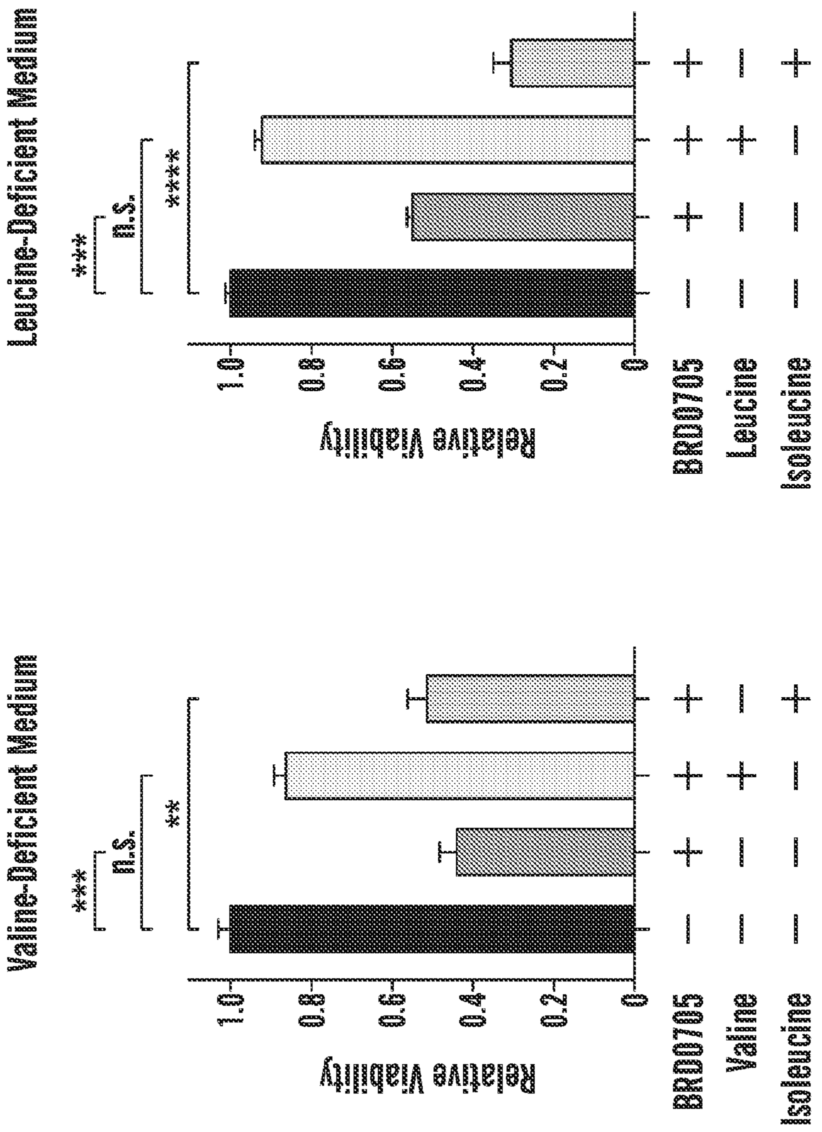
FIG. 17 shows the relative viability in the indicated deficient medium and under the indicated conditions.
Figure 18:
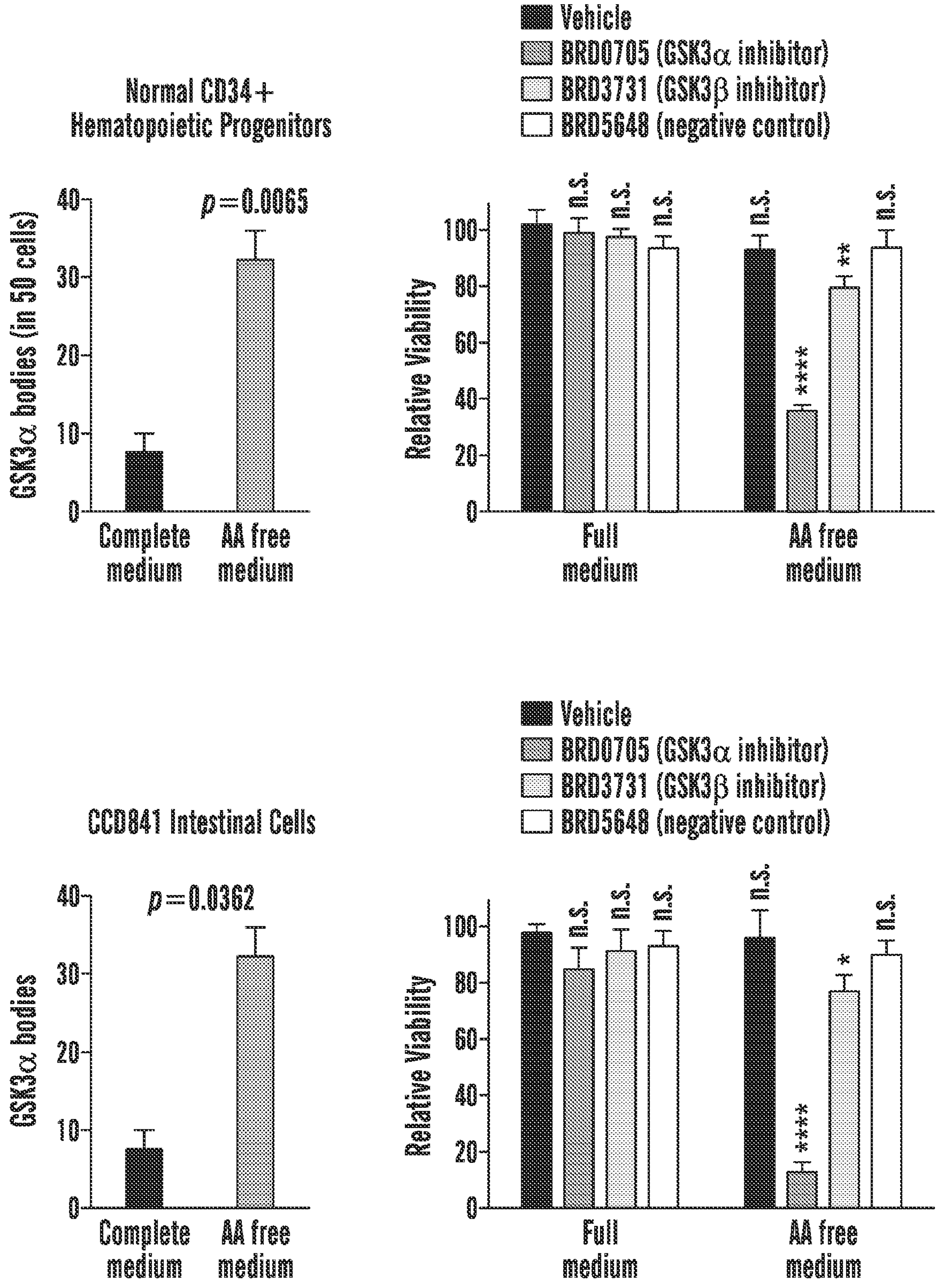
FIG. 18 shows the quantity of GSK3α-positive cytoplasmic bodies formed in the presence of asparaginase in normal CD34+ hematopoietic progenitor cells and CCD841 intestinal cells under the indicated conditions.

It was then sought to determine whether GSK3α promotes survival in response to starvation of these amino acids. Treatment with the GSK3α inhibitor BRD0705 impaired viability of Jurkat cells cultured in leucine- or valine-deficient medium, and the toxicity of GSK3α inhibition was rescued by replenishing the missing amino acid, but not isoleucine as a negative control (FIG. 17). It was then asked whether GSK3α promotes the survival of normal cells in response to essential amino acid starvation, using normal human CD34+ hematopoietic progenitors or CCD841 cells derived from normal human intestinal epithelium (38). It was found that essential amino acid starvation triggered GSK3α body formation in these cells (FIG. 18). Moreover, the GSK3α inhibitor BRD0705 impaired survival under essential amino acid starvation, whereas the structurally related negative control BRD5648 (24) had no effect (FIG. 18).

GSK3α Body Formation Predicts Asparaginase Response in Human Leukemia.

Figures 9A, 9B:
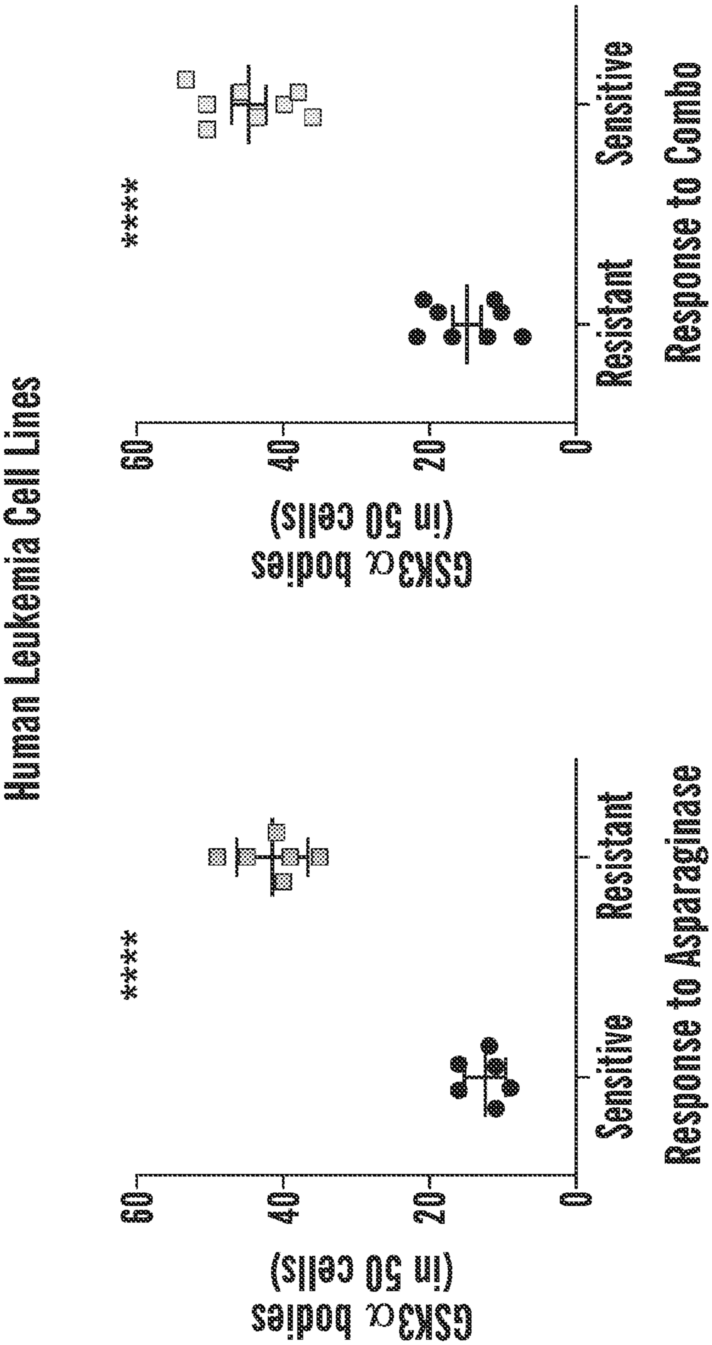
Figures 9C, 9D:
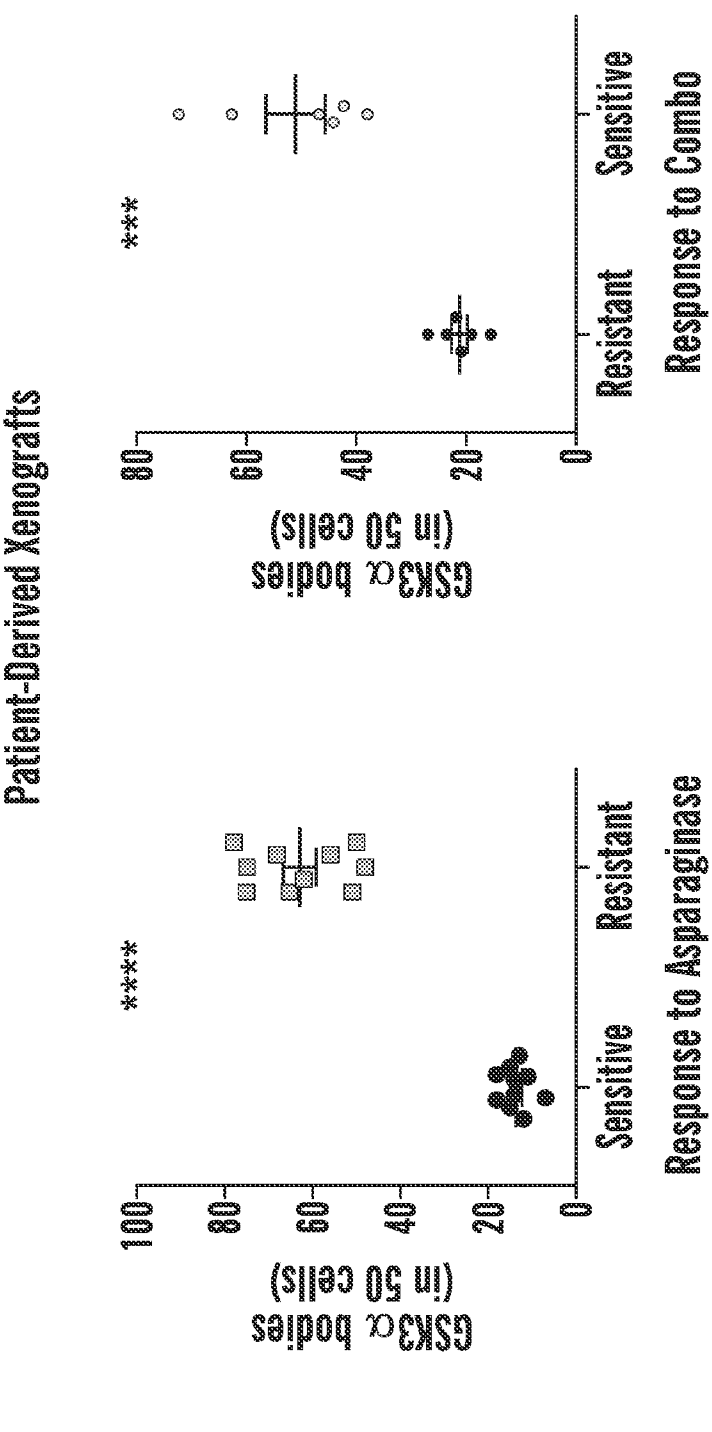
Figure 9E:
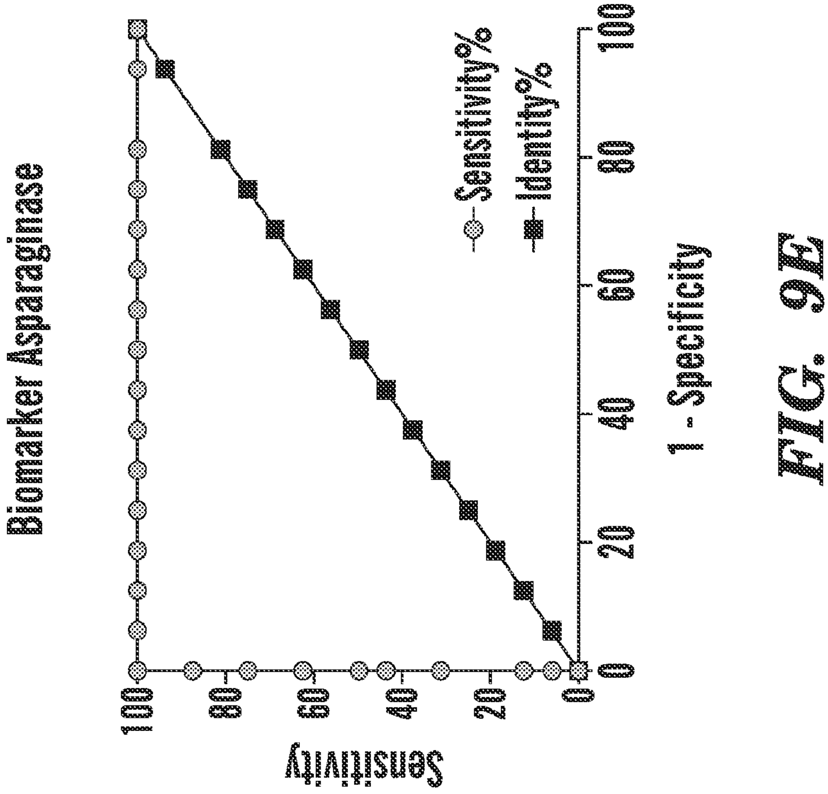
Figure 21C:
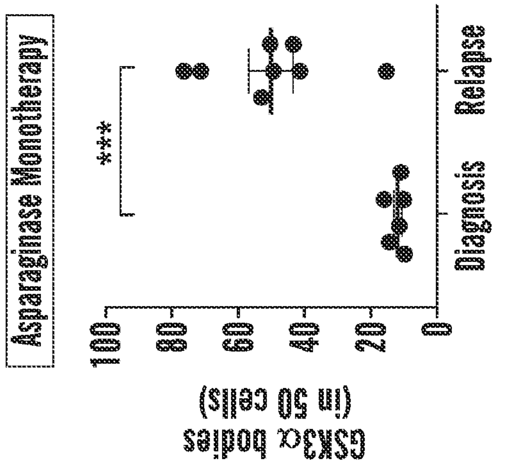
Figure 21B:
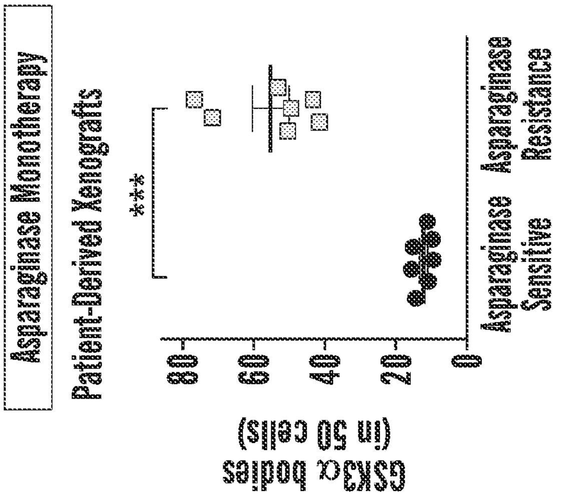

If formation of GSK3α bodies mediates resistance to asparagine starvation, then the ability of human leukemia cells to form these bodies should predict asparaginase response. To test this prediction, a cohort of human leukemias was leveraged, including established cell lines and primary patient-derived xenografts (PDXs). Assessment of asparaginasc cytotoxicity to these cases revealed a generally binary pattern of response, allowing their classification as either asparaginase sensitive or resistant (FIGS. S14, A and B). It was found that the ability of these cells to form GSK3α bodies after short-term culture with asparaginase was a strong predictor of asparaginase resistance, both in leukemia cell lines and PDX models (FIGS. 21A and 21B). Assessment of the performance of GSK3α body formation as a prognostic biomarker using receiver operating characteristic (ROC) analysis revealed that GSK3α body formation robustly discriminates asparaginase-sensitive versus resistant leukemias in this cohort (FIG. 9E). It was also asked whether GSK3α body formation correlates with clinical treatment response in this cohort of PDX models derived from patients with B-precursor acute lymphoblastic leukemia treated with asparaginasc-intensive combination chemotherapy on contemporary clinical trials (data not shown). It was found that samples collected at diagnosis from patients with who went on to have an excellent treatment response were unable to efficiently induce GSK3α bodies in response to asparaginase. By contrast, GSK3α body formation was robust in samples that relapsed after this asparaginase-based treatment regimen (FIG. 21C).

Figure 9F:
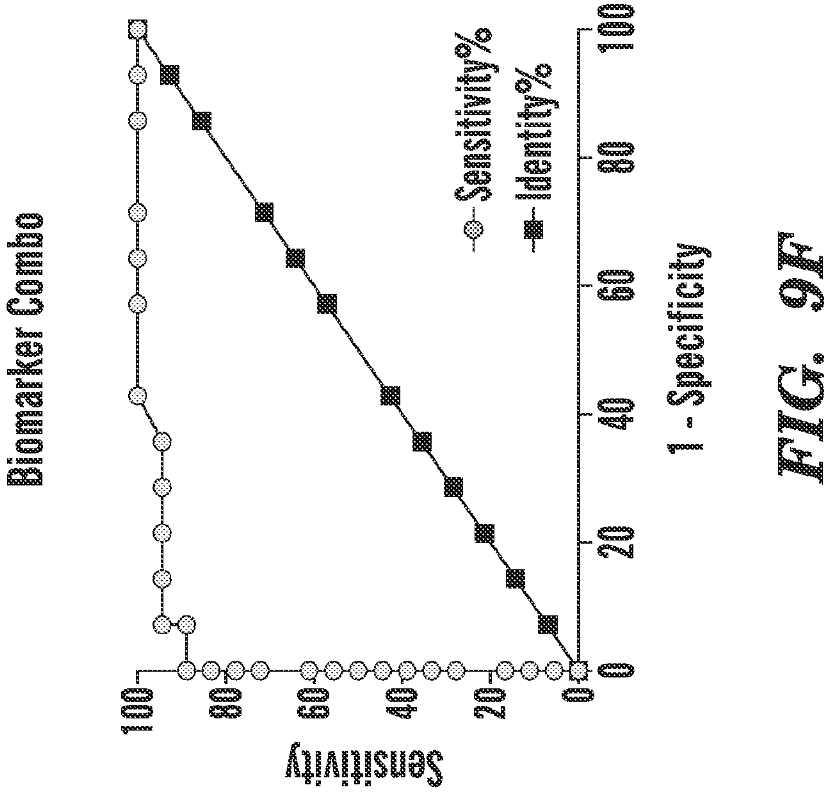
Figure 21D:
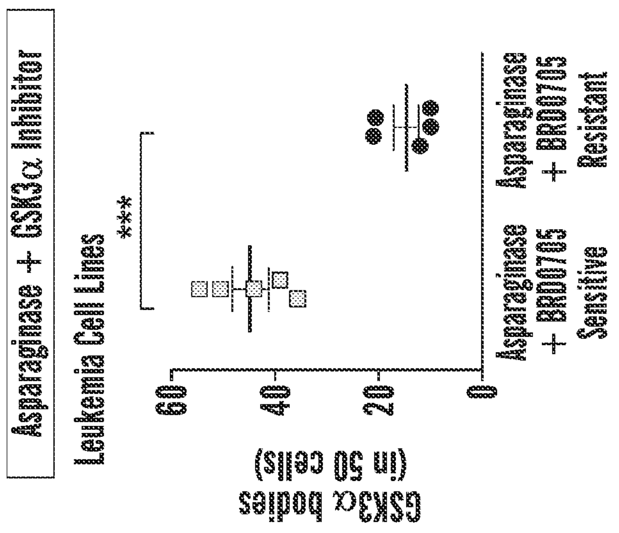
Figure 21E:
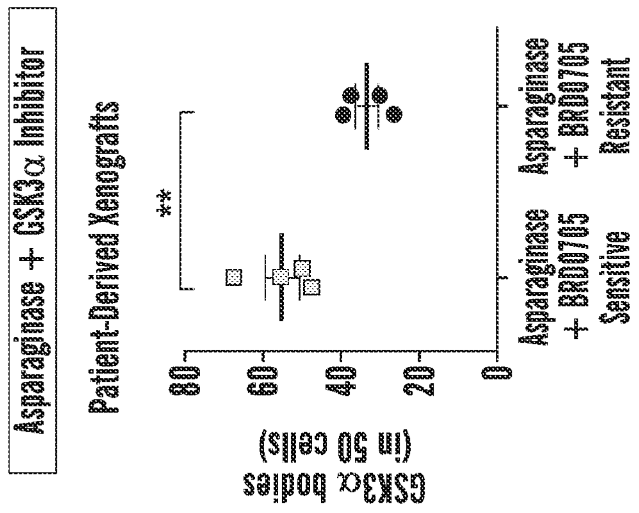

It was asked whether GSK3α body formation might allow the prospective identification of asparaginase-resistant cases that will prove sensitive to this combination, and distinguish these from cases that are resistant due to alternative mechanisms of asparaginase resistance. Indeed, asparaginase-resistant leukemia cell lines and PDX models that proved sensitive to the combination of asparaginase and the GSK3α inhibitor BRD0705 were able to form GSK3α bodies much more robustly than those that proved resistant to this combination (FIGS. 9F, 21D, 21E, FIGS. S14, C and D).

DISCUSSION

Data presented herein highlight that the tolerance of asparagine starvation is dependent on an N-terminal low-complexity domain of GSK3α that is lacking in its paralog GSK3β. In response to amino acid starvation, this domain mediates spatial sequestration of GSK3α, together with the cellular machinery for protein ubiquitination and proteasomal degradation, in membraneless cytoplasmic bodies. GSK3α body formation is stimulated in response to depletion of specific amino acids, including asparagine, leucine, and valine, indicating the existence of unknown cellular sensors for these amino acids. GSK3α promotes the survival of normal hematopoietic cells in response to essential amino acid starvation. Moreover, the ability of human leukemias to form GSK3α bodies predicts resistance to asparaginase, and sensitivity to asparaginase in combination with a small molecule GSK3α inhibitor. Without wishing to be bound by a particular theory, it is specifically contemplated herein that spatial sequestration of GSK3α with core components of the ubiquitin proteasome system provides a cellular mechanism to promote the catalytic efficiency of this catabolic source of amino acids in response to amino acid starvation. The ubiquitin proteasome system (UPS) has recently been shown to undergo phase separation in the nucleus in response to hyperosmotic stress, where it functions to degrade disassembled ribosomal proteins (39). Data presented herein indicate that the propensity of the UPS to undergo phase separation has been exploited for evolution of this inducible response to amino acid starvation. Deciphering the molecular regulation of this adaptive response will require the discovery and manipulation of the relevant molecules that sense amino acid insufficiency and signal this to GSK3α and the UPS. Data presented herein also indicates that the unique role of GSK3α in the amino acid starvation response may be one factor behind its evolutionary conservation, despite ubiquitous expression of its paralog GSK3β, which is largely redundant (12, 23).

While ATP-competitive inhibitors with approximately 8-fold selectivity for GSK3α over GSK3β can be developed (24), the ATP-binding pockets of these paralogs differ by a single amino acid, leading to some uncertainty over the degree to which this specificity can be further improved. Given the practical constraints of drug dosing in human patients, effectively inhibiting GSK3α with such small molecules will require doses that will result in at least partial inhibition of GSK3β. This approach is expected to have toxicity, because inhibiting both GSK3 paralogs results in activation of oncogenic β-catenin signaling (23). By contrast, GSK3α deficient mice are viable and have no known tumor predisposition (40). Thus, the data presented herein indicate an alternative approach for selective inhibition of GSK3α by selectively blocking its ability to undergo biomolecular condensation in response to asparagine starvation. The data presented herein also indicate that GSK3α body formation may provide a useful prognostic biomarker that will allow future clinical trials of asparaginase in combination with GSK3α inhibitors to be targeted to those patients most likely to derive meaningful clinical benefit.

REFERENCES

1. R. L. Wolfson, D. M. Sabatini, The Dawn of the Age of Amino Acid Sensors for the mTORC1 Pathway. Cell Metab 26, 301-309 (2017); published online EpubAug 1 (10.1016/j.cmet.2017.07.001).
2. H. P. Harding, I. Novoa, Y. Zhang, H. Zeng, R. Wek, M. Schapira, D. Ron, Regulated translation initiation controls stress-induced gene expression in mammalian cells. Mol Cell 6, 1099-1108 (2000); published online EpubNov (10.1016/s1097-2765 (00) 00108-8).
3. S. Broer, A. Broer, Amino acid homeostasis and signalling in mammalian cells and organisms. Biochem J 474, 1935-1963 (2017); published online EpubMay 25 (10.1042/BCJ20160822).
4. N. Hosokawa, T. Hara, T. Kaizuka, C. Kishi, A. Takamura, Y. Miura, S. Iemura, T. Natsume, K. Takehana, N. Yamada, J. L. Guan, N. Oshiro, N. Mizushima, Nutrient-dependent mTORC1 association with the ULK1-Atg13-FIP200 complex required for autophagy. Mol Biol Cell 20, 1981-1991 (2009); published online EpubApr (10.1091/mbc.E08-12-1248).
5. W. Palm, Y. Park, K. Wright, N. N. Pavlova, D. A. Tuveson, C. B. Thompson, The Utilization of Extracellular Proteins as Nutrients Is Suppressed by mTORC1. Cell 162, 259-270 (2015); published online EpubJul 16 (10.1016/j.cell.2015.06.017).
6. N. Mizushima, A. Yamamoto, M. Matsui, T. Yoshimori, Y. Ohsumi, In vivo analysis of autophagy in response to nutrient starvation using transgenic mice expressing a fluorescent autophagosome marker. Mol Biol Cell 15, 1101-1111 (2004); published online EpubMar (10.1091/mbc.e03-09-0704).
7. K. L. Rock, C. Gramm, L. Rothstein, K. Clark, R. Stein, L. Dick, D. Hwang, A. L. Goldberg, Inhibitors of the proteasome block the degradation of most cell proteins and the generation of peptides presented on MHC class I molecules. Cell 78, 761-771 (1994); published online EpubSep 9 (10.1016/s0092-8674 (94) 90462-6).
8. Y. T. Kwon, A. Ciechanover, The Ubiquitin Code in the Ubiquitin-Proteasome System and Autophagy. Trends in biochemical sciences 42, 873-886 (2017); published online EpubNov (10.1016/j.tibs.2017.09.002).
9. R. M. Vabulas, F. U. Hartl, Protein synthesis upon acute nutrient restriction relies on proteasome function. Science 310, 1960-1963 (2005); published online EpubDec 23 (10.1126/science. 1121925).
10. A. Suraweera, C. Munch, A. Hanssum, A. Bertolotti, Failure of amino acid homeostasis causes cell death following proteasome inhibition. Mol Cell 48, 242-253 (2012); published online EpubOct 26 (10.1016/j.molcel.2012.08.003).
11. H. An, A. Ordureau, M. Korner, J. A. Paulo, J. W. Harper, Systematic quantitative analysis of ribosome inventory during nutrient stress. Nature 583, 303-309 (2020); published online EpubJul (10.1038/s41586-020-2446-y).
12. P. Patel, J. R. Woodgett, Glycogen Synthase Kinase 3: A Kinase for All Pathways? Curr Top Dev Biol 123, 277-302 (2017) 10.1016/bs.ctdb.2016.11.011).
13. E. Siegfried, T. B. Chou, N. Perrimon, wingless signaling acts through zeste-white 3, the *Drosophila* homolog of glycogen synthase kinase-3, to regulate engrailed and establish cell fate. Cell 71, 1167-1179 (1992); published online EpubDec 24 (14.
14. L. Ruel, M. Bourouis, P. Heitzler, V. Pantesco, P. Simpson, *Drosophila* shaggy kinase and rat glycogen synthase kinase-3 have conserved activities and act downstream of Notch. Nature 362, 557-560 (1993); published online EpubApr 8 (10.1038/362557a0).
15. F. Ahmad, J. R. Woodgett, Emerging roles of GSK-3alpha in pathophysiology: Emphasis on cardio-metabolic disorders. Biochim Biophys Acta Mol Cell Res 1867, 118616 (2020); published online EpubFeb (10.1016/j.bbamcr.2019.118616).
16. S. P. Acebron, E. Karaulanov, B. S. Berger, Y. L. Huang, C. Niehrs, Mitotic wnt signaling promotes protein stabilization and regulates cell size. Mol Cell 54, 663-674 (2014); published online EpubMay 22 (10.1016/j.molcel.2014.04.014).
17. L. Hinze, R. Labrosse, J. Degar, T. Han, E. M. Schatoff, S. Schreek, S. Karim, C. McGuckin, J. Sacher, F. Wagner, M. Stanulla, C. Yuan, E. Sicinska, M. Giannakis, K. Ng, L. E. Dow, A. Gutierrez, Exploiting the therapeutic interaction of Wnt pathway activation and asparaginase for colorectal cancer therapy. Cancer Discov, (In press).
18. L. Hinze, M. Pfirrmann, S. Karim, J. Degar, C. McGuckin, D. Vinjamur, J. Sacher, K. E. Stevenson, D. S. Neuberg, E. Orellana, M. Stanulla, R. I. Gregory, D. E. Bauer, F. F. Wagner, K. Stegmaier, A. Gutierrez, Synthetic Lethality of Wnt Pathway Activation and Asparaginase in Drug-Resistant Acute Leukemias. Cancer Cell 35, 664-676 e667 (2019); published online EpubApr 15 (10.1016/j.ccell.2019.03.004).
19. V. F. Taelman, R. Dobrowolski, J. L. Plouhinec, L. C. Fuentealba, P. P. Vorwald, I. Gumper, D. D. Sabatini, E. M. De Robertis, Wnt signaling requires sequestration of glycogen synthase kinase 3 inside multivesicular endosomes. Cell 143, 1136-1148 (2010); published online EpubDec 23 (10.1016/j.cell.2010.11.034).
20. Y. L. Huang, Z. Anvarian, G. Doderlein, S. P. Acebron, C. Niehrs, Maternal Wnt/STOP signaling promotes cell division during early *Xenopus* embryogenesis. Proceedings of the National Academy of Sciences of the United States of America 112, 5732-5737 (2015); published online EpubMay 5 (10.1073/pnas. 1423533112).
21. S. Koch, S. P. Acebron, J. Herbst, G. Hatiboglu, C. Niehrs, Post-transcriptional Wnt Signaling Governs Epididymal Sperm Maturation. Cell 163, 1225-1236 (2015); published online EpubNov 19 (10.1016/j.cell.2015.10.029).
22. B. Guezguez, M. Almakadi, Y. D. Benoit, Z. Shapovalova, S. Rahmig, A. Fiebig-Comyn, F. L. Casado, B. Tanasijevic, S. Bresolin, R. Masetti, B. W. Doble, M. Bhatia, GSK3 Deficiencies in Hematopoietic Stem Cells Initiate Pre-neoplastic State that Is Predictive of Clinical Outcomes of Human Acute Leukemia. Cancer Cell 29, 61-74 (2016); published online EpubJan 11 (10.1016/j.ccell.2015.11.012).

23. B. W. Doble, S. Patel, G. A. Wood, L. K. Kockeritz, J. R. Woodgett, Functional redundancy of GSK-3alpha and GSK-3beta in Wnt/beta-catenin signaling shown by using an allelic series of embryonic stem cell lines. Dev Cell 12, 957-971 (2007); published online EpubJun (10.1016/j.devcel.2007.04.001).
24. F. F. Wagner, L. Benajiba, A. J. Campbell, M. Weiwer, J. R. Sacher, J. P. Gale, L. Ross, A. Puissant, G. Alexe, A. Conway, M. Back, Y. Pikman, I. Galinsky, D. J. DeAngelo, R. M. Stone, T. Kaya, X. Shi, M. B. Robers, T. Machleidt, J. Wilkinson, O. Hermine, A. Kung, A. J. Stein, D. Lakshminarasimhan, M. T. Hemann, E. Scolnick, Y. L. Zhang, J. Q. Pan, K. Stegmaier, E. B. Holson, Exploiting an Asp-Glu "switch" in glycogen synthase kinase 3 to design paralog-selective inhibitors for use in acute myeloid leukemia. Sci Transl Med 10, (2018); published online EpubMar 7 (10.1126/scitranslmed.aam8460).
25. V. Banerji, S. M. Frumm, K. N. Ross, L. S. Li, A. C. Schinzel, C. K. Hahn, R. M. Kakoza, K. T. Chow, L. Ross, G. Alexe, N. Tolliday, H. Inguilizian, I. Galinsky, R. M. Stone, D. J. DeAngelo, G. Roti, J. C. Aster, W. C. Hahn, A. L. Kung, K. Stegmaier, The intersection of genetic and chemical genomic screens identifies GSK-3alpha as a target in human acute myeloid leukemia. J Clin Invest 122, 935-947 (2012); published online EpubMar (10.1172/JCI46465).
26. C. J. Sigrist, E. de Castro, L. Cerutti, B. A. Cuche, N. Hulo, A. Bridge, L. Bougueleret, I. Xenarios, New and continuing developments at PROSITE. Nucleic Acids Res 41, D344-347 (2013); published online EpubJan (10.1093/nar/gks1067).
27. R. C. NCBI, Database resources of the National Center for Biotechnology Information. Nucleic Acids Res 44, D7-19 (2016); published online EpubJan 4 (10.1093/nar/gkv1290).
28. Y. J. Huang, T. B. Acton, G. T. Montelione, DisMeta: a meta server for construct design and optimization. Methods Mol Biol 1091, 3-16 (2014) 10.1007/978-1-62703-691-7_1).
29. S. Boeynaems, S. Alberti, N. L. Fawzi, T. Mittag, M. Polymenidou, F. Rousseau, J. Schymkowitz, J. Shorter, B. Wolozin, L. Van Den Bosch, P. Tompa, M. Fuxreiter, Protein Phase Separation: A New Phase in Cell Biology. Trends Cell Biol 28, 420-435 (2018); published online EpubJun (10.1016/j.tcb.2018.02.004).
30. S. F. Banani, H. O. Lee, A. A. Hyman, M. K. Rosen, Biomolecular condensates: organizers of cellular biochemistry. Nature reviews. Molecular cell biology 18, 285-298 (2017); published online EpubMay (10.1038/nrm.2017.7).
31. G. V. Los, K. Wood, The HaloTag: a novel technology for cell imaging and protein analysis. Methods Mol Biol 356, 195-208 (2007) 10.1385/1-59745-217-3:195).
32. E. M. Sontag, R. S. Samant, J. Frydman, Mechanisms and Functions of Spatial Protein Quality Control. Annu Rev Biochem 86, 97-122 (2017); published online EpubJun 20 (10.1146/annurev-biochem-060815-014616).
33. L. Shrestha, H. J. Patel, G. Chiosis, Chemical Tools to Investigate Mechanisms Associated with HSP90 and HSP70 in Disease. Cell Chem Biol 23, 158-172 (2016); published online EpubJan 21 (10.1016/j.chembiol.2015.12.006).
34. A. Rodina, P. D. Patel, Y. Kang, Y. Patel, I. Baaklini, M. J. Wong, T. Taldone, P. Yan, C. Yang, R. Maharaj, A. Gozman, M. R. Patel, H. J. Patel, W. Chirico, H. Erdjument-Bromage, T. T. Talele, J. C. Young, G. Chiosis, Identification of an allosteric pocket on human hsp70 reveals a mode of inhibition of this therapeutically important protein. Chem Biol 20, 1469-1480 (2013); published online EpubDec 19 (10.1016/j.chembiol.2013.10.008).
35. R. L. Wolfson, L. Chantranupong, R. A. Saxton, K. Shen, S. M. Scaria, J. R. Cantor, D. M. Sabatini, Sestrin2 is a leucine sensor for the mTORC1 pathway. Science 351, 43-48 (2016); published online EpubJan 1 (10.1126/science.aab2674).
36. X. Gu, J. M. Orozco, R. A. Saxton, K. J. Condon, G. Y. Liu, P. A. Krawczyk, S. M. Scaria, J. W. Harper, S. P. Gygi, D. M. Sabatini, SAMTOR is an S-adenosylmethionine sensor for the mTORC1 pathway. Science 358, 813-818 (2017); published online EpubNov 10 (10.1126/science.aao3265).
37. L. Chantranupong, S. M. Scaria, R. A. Saxton, M. P. Gygi, K. Shen, G. A. Wyant, T. Wang, J. W. Harper, S. P. Gygi, D. M. Sabatini, The CASTOR Proteins Are Arginine Sensors for the mTORC1 Pathway. Cell 165, 153-164 (2016); published online EpubMar 24 (10.1016/j.cell.2016.02.035).
38. A. A. Thompson, S. Dilworth, R. J. Hay, Isolation and culture of colonic epithelial cells in serum-free medium. Journal of Tissue Culture Methods 9, 117-122 (1985) https://doi.org/10.1007/BF01797782).
39. S. Yasuda, H. Tsuchiya, A. Kaiho, Q. Guo, K. Ikeuchi, A. Endo, N. Arai, F. Ohtake, S. Murata, T. Inada, W. Baumeister, R. Fernandez-Busnadiego, K. Tanaka, Y. Saeki, Stress- and ubiquitylation-dependent phase separation of the proteasome. Nature 578, 296-300 (2020); published online EpubFeb (10.1038/s41586-020-1982-9).
40. K. MacAulay, B. W. Doble, S. Patel, T. Hansotia, E. M. Sinclair, D. J. Drucker, A. Nagy, J. R. Woodgett, Glycogen synthase kinase 3alpha-specific regulation of murine hepatic glycogen metabolism. Cell Metab 6, 329-337 (2007); published online EpubOct (10.1016/j.cmet.2007.08.013).
41. F. F. Wagner, L. Benajiba, A. J. Campbell, M. Weiwer, J. R. Sacher, J. P. Gale, L. Ross, A. Puissant, G. Alexe, A. Conway, M. Back, Y. Pikman, I. Galinsky, D. J. DeAngelo, R. M. Stone, T. Kaya, X. Shi, M. B. Robers, T. Machleidt, J. Wilkinson, O. Hermine, A. Kung, A. J. Stein, D. Lakshminarasimhan, M. T. Hemann, E. Scolnick, Y. L. Zhang, J. Q. Pan, K. Stegmaier, E. B. Holson, Exploiting an Asp-Glu "switch" in glycogen synthase kinase 3 to design paralog-selective inhibitors for use in acute myeloid leukemia. Sci Transl Med 10, (2018); published online EpubMar 7 (10.1126/scitranslmed.aam8460).
42. T. Taldone, Y. Kang, H. J. Patel, M. R. Patel, P. D. Patel, A. Rodina, Y. Patel, A. Gozman, R. Maharaj, C. C. Clement, A. Lu, J. C. Young, G. Chiosis, Heat shock protein 70 inhibitors. 2. 2,5'-thiodipyrimidines, 5-(phenylthio)pyrimidines, 2-(pyridin-3-ylthio)pyrimidines, and 3-(phenylthio)pyridines as reversible binders to an allosteric site on heat shock protein 70. J Med Chem 57, 1208-1224 (2014); published online EpubFeb 27 (10.1021/jm401552y).
43. Y. Kang, T. Taldone, H. J. Patel, P. D. Patel, A. Rodina, A. Gozman, R. Maharaj, C. C. Clement, M. R. Patel, J. L. Brodsky, J. C. Young, G. Chiosis, Heat shock protein 70 inhibitors. 1. 2,5'-thiodipyrimidine and 5-(phenylthio)pyrimidine acrylamides as irreversible binders to an allosteric site on heat shock protein 70. J Med Chem 57, 1188-1207 (2014); published online EpubFeb 27 (10.1021/jm401551n).

44. V. F. Taelman, R. Dobrowolski, J. L. Plouhinec, L. C. Fuentealba, P. P. Vorwald, I. Gumper, D. D. Sabatini, E. M. De Robertis, Wnt signaling requires sequestration of glycogen synthase kinase 3 inside multivesicular endosomes. Cell 143, 1136-1148 (2010); published online EpubDec 23 (10.1016/j.cell.2010.11.034).
45. T. P. Dao, R. M. Kolaitis, H. J. Kim, K. O'Donovan, B. Martyniak, E. Colicino, H. Hehnly, J. P. Taylor, C. A. Castañeda, Ubiquitin Modulates Liquid-Liquid Phase Separation of UBQLN2 via Disruption of Multivalent Interactions. Mol Cell 69, 965-978.e966 (2018); published online EpubMar 15 (10.1016/j.molcel.2018.02.004).
46. E. Fraser, N. Young, R. Dajani, J. Franca-Koh, J. Ryves, R. S. Williams, M. Yeo, M. T. Webster, C. Richardson, M. J. Smalley, L. H. Pearl, A. Harwood, T. C. Dale, Identification of the Axin and Frat binding region of glycogen synthase kinase-3. J Biol Chem 277, 2176-2185 (2002); published online EpubJan 18 (10.1074/jbc.M109462200).
47. R. Dajani, E. Fraser, S. M. Roe, M. Yeo, V. M. Good, V. Thompson, T. C. Dale, L. H. Pearl, Structural basis for recruitment of glycogen synthase kinase 3beta to the axin-APC scaffold complex. EMBO J 22, 494-501 (2003); published online EpubFeb 3 (10.1093/emboj/cdg068).
B. W. Doble, S. Patel, G. A. Wood, L. K. Kockeritz, J. R. Woodgett, Functional redundancy of GSK-3alpha and GSK-3beta in Wnt/beta-catenin signaling shown by using an allelic series of embryonic stem cell lines. Dev Cell 12, 957-971 (2007); published online EpubJun (10.1016/j.devcel.2007.04.001).

TABLE 3

Examples of E3 recruiting elements and respective E3 ubiquitin ligases employed in recent years (~2) for PROTAC-development. Dashed arrows represent vectors used for linker attachment in PROTAC synthesis.

| E3 ubiquitin ligase | E3 recruiting element (E3RE) | Target protein type |
|---|---|---|
| VHL[a] | 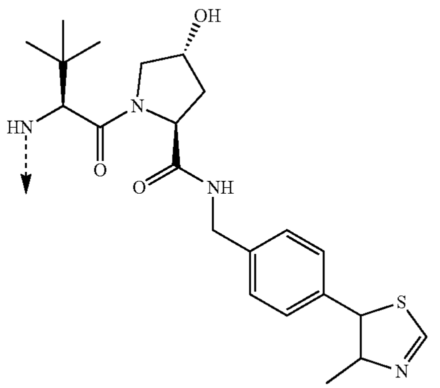 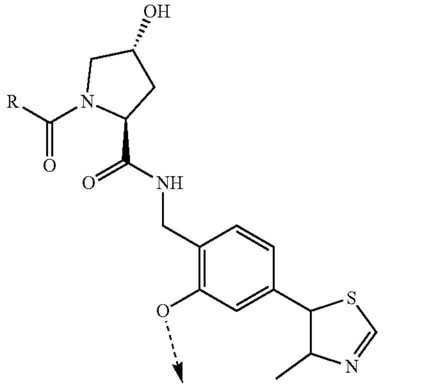 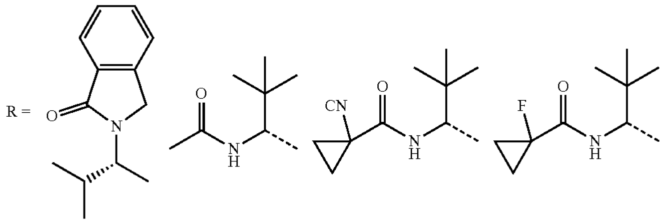 | Kinases (cytosolic and receptor), transcription factors, epigenetic readers and erasers, E3 ubiquitin ligases |

TABLE 3-continued

Examples of E3 recruiting elements and respective E3 ubiquitin ligases employed in recent years (~2) for PROTAC-development. Dashed arrows represent vectors used for linker attachment in PROTAC synthesis.

| E3 ubiquitin ligase | E3 recruiting element (E3RE) | Target protein type |
|---|---|---|
| CRBN | 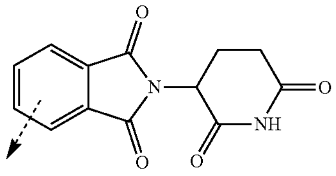 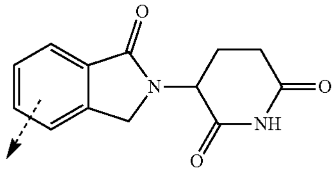 | Kinases (cytosolic and receptor), transcription factors, epigenetic readers and erasers, E3 ubiquitin ligases |
| XIAP and cIAP[a] | 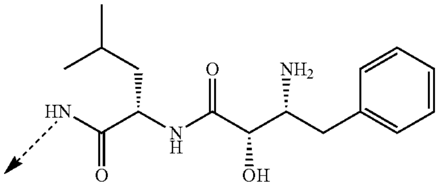 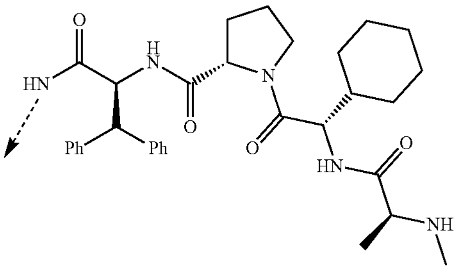 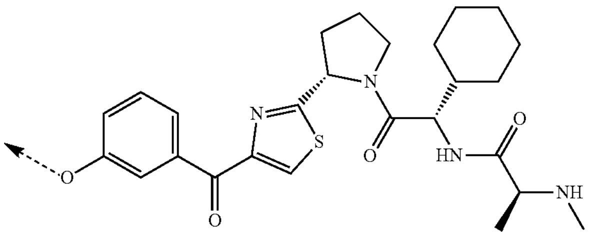 | Kinases, transcription factors, epigenetic readers, E3 ubiquitin ligases |
| Keap1 | 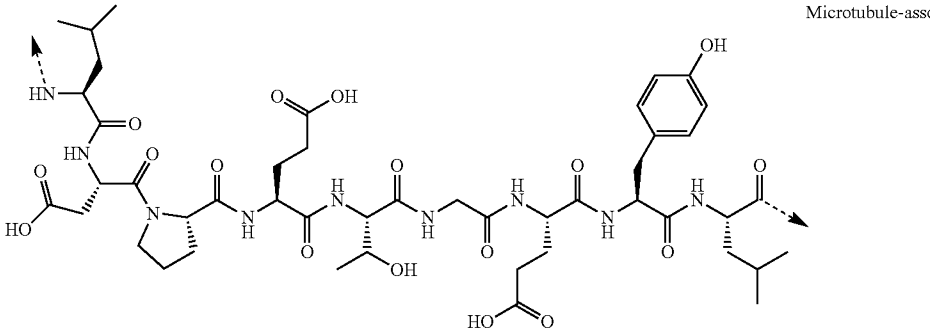 | Microtubule-associate protein (tau) |

TABLE 3-continued

Examples of E3 recruiting elements and respective E3 ubiquitin ligases employed in recent years (~2) for PROTAC-development. Dashed arrows represent vectors used for linker attachment in PROTAC synthesis.

| E3 ubiquitin ligase | E3 recruiting element (E3RE) | Target protein type |
|---|---|---|
| RNF4 | 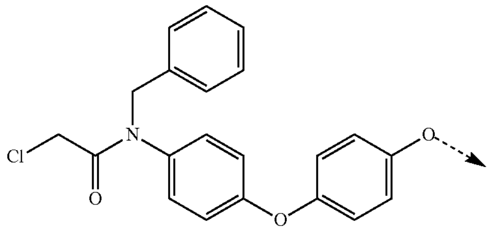 | Epigenetic reader |
| RNF114 | 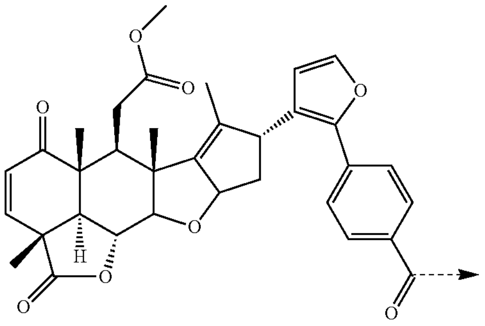 | Epigenetic reader |
| MDM2 | 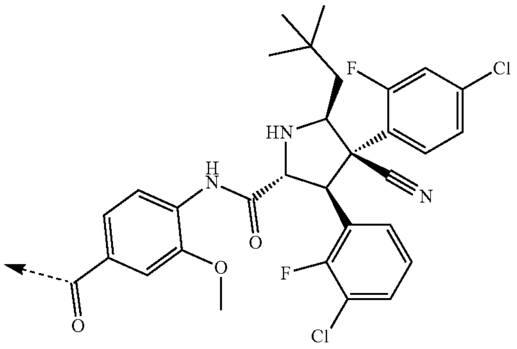 [SMILES: COc1cc(C=O)ccc1NC(=O)[C@@H]1N[C@@H](CC(C)(C)C)[C@](C#N)(c2ccc(Cl)cc2F)[C@H]1c1cccc(Cl)c1F] | Epigenetic reader |

[a]notable examples

The invention claimed is:

1. A method of treating cancer, the method comprising:

a) obtaining a biological sample from a subject having cancer;

b) assaying the sample and identifying the cancer as forming GSK3α-positive puncta; and c) administering an asparaginase and an agent that inhibits GSK3α to the subject who has been identified as forming GSK3α-positive puncta, wherein the assaying is treating the sample with an the asparaginase, or culturing the sample in conditions of asparagine starvation or amino acid starvation.

2. The method of claim 1, wherein the cancer is asparaginase-resistant cancer.

3. The method of claim 1, wherein the GSK3α-positive puncta are formed in response to asparagine starvation or following contact with an asparaginase treatment.

4. The method of claim 1, wherein the cancer is selected from the list consisting of: a carcinoma, a melanoma, a sarcoma, a myeloma, a leukemia, and a lymphoma.

5. The method of claim 1, wherein the cancer is a solid tumor, colon cancer, or pancreatic cancer.

6. The method of claim 4, wherein the leukemia is selected from the group consisting of: acute myeloid leukemia (AML), Chronic myeloid leukemia (CML), Acute lymphocytic leukemia (ALL), and Chronic lymphocytic leukemia (CLL).

7. The method of claim 1, wherein the cancer is metastatic.

8. The method of claim 1, wherein the biological sample is a biopsied sample, a tissue sample or a blood sample.

9. The method of claim 8, wherein the biopsied sample is a tumor sample.

10. The method of claim 1, wherein the asparaginase is selected from the group consisting of: L-asparaginase (Elspar), pegaspargase (PEG-asparaginase), SC-PEG asparaginase, Calaspargase pegol (Cal-PEG; SHP663), *Erwinia* asparaginase, cristantaspase, and Asparaginase medac.

11. The method of claim 1, wherein the agent that inhibits GSK3α is selected from the group consisting of a small molecule, an antibody, a peptide, a genome editing system, an antisense oligonucleotide, and an RNAi.

12. The method of claim 11, wherein the small molecule is selected from the group consisting of: BRD0705, BRD4963, BRD1652, BRD3731, CHIR-98014, LY2090314, AZD1080, CHIR-99021 (CT99021) HCl, CHIR-99021 (CT99021), BIO-acetoxime, SB216763, SB415286, Abemaciclib (LY2835210), AT-9283, RGB-286638, PHA-793887, AT-7519, AZD-5438, OTS-167, 9-ING-41, Tideglusib (NP031112), and AR-A014418.

13. The method of claim 1, wherein inhibiting GSK3α is inhibiting the expression level and/or activity of GSK3α.

14. The method of claim 13, wherein the expression level and/or activity of GSK3α is inhibited by at least 50%, at least 60%, at least 70%, at least 80%, at least 90%, or more as compared to an appropriate control.

15. The method of claim 1, wherein the assaying is done by immunofluorescence or flow cytometry.

16. The method of claim 1, wherein the subject has previously been administered an anti-cancer therapy.

17. The method of claim 1, wherein the subject has not previously been administered an anti-cancer therapy.

* * * * *

SEQUENCE LISTING

<160> NUMBER OF SEQ ID NOS: 6

<210> SEQ ID NO 1
<211> LENGTH: 1461
<212> TYPE: DNA
<213> ORGANISM: Homo sapiens

<400> SEQUENCE: 1
ctcggcgcca tgagcggcgg cgggccttcg ggaggcggcc ctgggggctc gggcagggcg 60
cggactagct cgttcgcgga gcccggcggc ggaggcggag gaggcggcgg cggccccgga 120
ggctcggcct ccggcccagg cggcaccggc ggcggaaagg catctgtcgg ggccatgggt 180
gggggcgtcg gggcctcgag ctccgggggt ggacccggcg gcagcggcgg aggaggcagc 240
ggaggccccg gcgcaggcac tagcttcccg ccgcccgggg tgaagctggg ccgtgacagc 300
gggaaggtga ccacagtcgt agccactcta ggccaaggcc cagagcgctc ccaagaagtg 360

-continued

```
gcttacacgg acatcaaagt gattggcaat ggctcatttg gggtcgtgta ccaggcacgg    420

ctggcagaga ccagggaact agtcgccatc aagaaggttc tccaggacaa gaggttcaag    480

aaccgagagc tgcagatcat gcgtaagctg gaccactgca atattgtgag gctgagatac    540

tttttctact ccagtggcga gaagaaagac gagctttacc taaatctggt gctggaatat    600

gtgcccgaga cagtgtaccg ggtggcccgc cacttcacca aggccaagtt gaccatccct    660

atcctctatg tcaaggtgta catgtaccag ctcttccgca gcttggccta catccactcc    720

cagggcgtgt gtcaccgcga catcaagccc cagaacctgc tggtggaccc tgacactgct    780

gtcctcaagc tctgcgattt tggcagtgca aagcagttgg tccgagggga gcccaatgtc    840

tcctacatct gttctcgcta ctaccgggcc ccagagctca tctttggagc cactgattac    900

acctcatcca tcgatgtttg gtcagctggc tgtgtactgg cagagctcct cttgggccag    960

cccatcttcc ctggggacag tggggtggac cagctggtgg agatcatcaa ggtgctggga   1020

acaccaaccc gggaacaaat ccgagagatg aaccccaact acacggagtt caagttccct   1080

cagattaaag ctcacccctg gacaaaggtg ttcaaatctc gaacgccgcc agaggccatc   1140

gcgctctgct ctagcctgct ggagtacacc ccatcctcaa ggctctcccc actagaggcc   1200

tgtgcgcaca gcttctttga tgaactgcga tgtctgggaa cccagctgcc taacaaccgc   1260

ccacttcccc ctctcttcaa cttcagtgct ggtgaactct ccatccaacc gtctctcaac   1320

gccattctca tccctcctca cttgaggtcc ccagcgggca ctaccaccct caccccgtcc   1380

tcacaagctt taactgagac tccgaccagc tcagactggc agtcgaccga tgccacacct   1440

accctcacta actcctcctg a                                             1461
```

```
<210> SEQ ID NO 2
<211> LENGTH: 483
<212> TYPE: PRT
<213> ORGANISM: Homo sapiens

<400> SEQUENCE: 2

Met Ser Gly Gly Gly Pro Ser Gly Gly Gly Pro Gly Gly Ser Gly Arg
1               5                   10                  15

Ala Arg Thr Ser Ser Phe Ala Glu Pro Gly Gly Gly Gly Gly Gly Gly
            20                  25                  30

Gly Gly Gly Pro Gly Gly Ser Ala Ser Gly Pro Gly Gly Thr Gly Gly
        35                  40                  45

Gly Lys Ala Ser Val Gly Ala Met Gly Gly Gly Val Gly Ala Ser Ser
    50                  55                  60

Ser Gly Gly Gly Pro Gly Gly Ser Gly Gly Gly Gly Ser Gly Gly Pro
65                  70                  75                  80

Gly Ala Gly Thr Ser Phe Pro Pro Pro Gly Val Lys Leu Gly Arg Asp
                85                  90                  95

Ser Gly Lys Val Thr Thr Val Val Ala Thr Leu Gly Gln Gly Pro Glu
            100                 105                 110

Arg Ser Gln Glu Val Ala Tyr Thr Asp Ile Lys Val Ile Gly Asn Gly
        115                 120                 125

Ser Phe Gly Val Val Tyr Gln Ala Arg Leu Ala Glu Thr Arg Glu Leu
    130                 135                 140

Val Ala Ile Lys Lys Val Leu Gln Asp Lys Arg Phe Lys Asn Arg Glu
145                 150                 155                 160

Leu Gln Ile Met Arg Lys Leu Asp His Cys Asn Ile Val Arg Leu Arg
                165                 170                 175
```

```
Tyr Phe Phe Tyr Ser Ser Gly Glu Lys Lys Asp Glu Leu Tyr Leu Asn
            180                 185                 190

Leu Val Leu Glu Tyr Val Pro Glu Thr Val Tyr Arg Val Ala Arg His
        195                 200                 205

Phe Thr Lys Ala Lys Leu Thr Ile Pro Ile Leu Tyr Val Lys Val Tyr
    210                 215                 220

Met Tyr Gln Leu Phe Arg Ser Leu Ala Tyr Ile His Ser Gln Gly Val
225                 230                 235                 240

Cys His Arg Asp Ile Lys Pro Gln Asn Leu Leu Val Asp Pro Asp Thr
                245                 250                 255

Ala Val Leu Lys Leu Cys Asp Phe Gly Ser Ala Lys Gln Leu Val Arg
            260                 265                 270

Gly Glu Pro Asn Val Ser Tyr Ile Cys Ser Arg Tyr Tyr Arg Ala Pro
        275                 280                 285

Glu Leu Ile Phe Gly Ala Thr Asp Tyr Thr Ser Ser Ile Asp Val Trp
    290                 295                 300

Ser Ala Gly Cys Val Leu Ala Glu Leu Leu Leu Gly Gln Pro Ile Phe
305                 310                 315                 320

Pro Gly Asp Ser Gly Val Asp Gln Leu Val Glu Ile Ile Lys Val Leu
                325                 330                 335

Gly Thr Pro Thr Arg Glu Gln Ile Arg Glu Met Asn Pro Asn Tyr Thr
            340                 345                 350

Glu Phe Lys Phe Pro Gln Ile Lys Ala His Pro Trp Thr Lys Val Phe
        355                 360                 365

Lys Ser Arg Thr Pro Pro Glu Ala Ile Ala Leu Cys Ser Ser Leu Leu
    370                 375                 380

Glu Tyr Thr Pro Ser Ser Arg Leu Ser Pro Leu Glu Ala Cys Ala His
385                 390                 395                 400

Ser Phe Phe Asp Glu Leu Arg Cys Leu Gly Thr Gln Leu Pro Asn Asn
                405                 410                 415

Arg Pro Leu Pro Pro Leu Phe Asn Phe Ser Ala Gly Glu Leu Ser Ile
            420                 425                 430

Gln Pro Ser Leu Asn Ala Ile Leu Ile Pro Pro His Leu Arg Ser Pro
        435                 440                 445

Ala Gly Thr Thr Thr Leu Thr Pro Ser Ser Gln Ala Leu Thr Glu Thr
    450                 455                 460

Pro Thr Ser Ser Asp Trp Gln Ser Thr Asp Ala Thr Pro Thr Leu Thr
465                 470                 475                 480

Asn Ser Ser


<210> SEQ ID NO 3
<211> LENGTH: 348
<212> TYPE: PRT
<213> ORGANISM: Escherichia coli

<400> SEQUENCE: 3

Met Glu Phe Phe Lys Lys Thr Ala Leu Ala Ala Leu Val Met Gly Phe
1               5                   10                  15

Ser Gly Ala Ala Leu Ala Leu Pro Asn Ile Thr Ile Leu Ala Thr Gly
            20                  25                  30

Gly Thr Ile Ala Gly Gly Gly Asp Ser Ala Thr Lys Ser Asn Tyr Thr
        35                  40                  45

Val Gly Lys Val Gly Val Glu Asn Leu Val Asn Ala Val Pro Gln Leu
    50                  55                  60
```

-continued

Lys Asp Ile Ala Asn Val Lys Gly Glu Gln Val Val Asn Ile Gly Ser
65 70 75 80

Gln Asp Met Asn Asp Asn Val Trp Leu Thr Leu Ala Lys Lys Ile Asn
85 90 95

Thr Asp Cys Asp Lys Thr Asp Gly Phe Val Ile Thr His Gly Thr Asp
100 105 110

Thr Met Glu Glu Thr Ala Tyr Phe Leu Asp Leu Thr Val Lys Cys Asp
115 120 125

Lys Pro Val Val Met Val Gly Ala Met Arg Pro Ser Thr Ser Met Ser
130 135 140

Ala Asp Gly Pro Phe Asn Leu Tyr Asn Ala Val Val Thr Ala Ala Asp
145 150 155 160

Lys Ala Ser Ala Asn Arg Gly Val Leu Val Val Met Asn Asp Thr Val
165 170 175

Leu Asp Gly Arg Asp Val Thr Lys Thr Asn Thr Thr Asp Val Ala Thr
180 185 190

Phe Lys Ser Val Asn Tyr Gly Pro Leu Gly Tyr Ile His Asn Gly Lys
195 200 205

Ile Asp Tyr Gln Arg Thr Pro Ala Arg Lys His Thr Ser Asp Thr Pro
210 215 220

Phe Asp Val Ser Lys Leu Asn Glu Leu Pro Lys Val Gly Ile Val Tyr
225 230 235 240

Asn Tyr Ala Asn Ala Ser Asp Leu Pro Ala Lys Ala Leu Val Asp Ala
245 250 255

Gly Tyr Asp Gly Ile Val Ser Ala Gly Val Gly Asn Gly Asn Leu Tyr
260 265 270

Lys Ser Val Phe Asp Thr Leu Ala Thr Ala Ala Lys Thr Gly Thr Ala
275 280 285

Val Val Arg Ser Ser Arg Val Pro Thr Gly Ala Thr Thr Gln Asp Ala
290 295 300

Glu Val Asp Asp Ala Lys Tyr Gly Phe Val Ala Ser Gly Thr Leu Asn
305 310 315 320

Pro Gln Lys Ala Arg Val Leu Leu Gln Leu Ala Leu Thr Gln Thr Lys
325 330 335

Asp Pro Gln Gln Ile Gln Gln Ile Phe Asn Gln Tyr
340 345

<210> SEQ ID NO 4
<211> LENGTH: 348
<212> TYPE: PRT
<213> ORGANISM: Dickeya chrysanthemi

<400> SEQUENCE: 4

Met Glu Arg Trp Phe Lys Ser Leu Phe Val Leu Val Leu Phe Phe Val
1 5 10 15

Phe Thr Ala Ser Ala Ala Asp Lys Leu Pro Asn Ile Val Ile Leu Ala
20 25 30

Thr Gly Gly Thr Ile Ala Gly Ser Ala Ala Thr Gly Thr Gln Thr Thr
35 40 45

Gly Tyr Lys Ala Gly Ala Leu Gly Val Asp Thr Leu Ile Asn Ala Val
50 55 60

Pro Glu Val Lys Lys Leu Ala Asn Val Lys Gly Glu Gln Phe Ser Asn
65 70 75 80

Met Ala Ser Glu Asn Met Thr Gly Asp Val Val Leu Lys Leu Ser Gln

-continued

```
                85                  90                  95

Arg Val Asn Glu Leu Leu Ala Arg Asp Asp Val Asp Gly Val Val Ile
            100                 105                 110

Thr His Gly Thr Asp Thr Val Glu Glu Ser Ala Tyr Phe Leu His Leu
        115                 120                 125

Thr Val Lys Ser Asp Lys Pro Val Val Phe Val Ala Ala Met Arg Pro
    130                 135                 140

Ala Thr Ala Ile Ser Ala Asp Gly Pro Met Asn Leu Leu Glu Ala Val
145                 150                 155                 160

Arg Val Ala Gly Asp Lys Gln Ser Arg Gly Arg Gly Val Met Val Val
                165                 170                 175

Leu Asn Asp Arg Ile Gly Ser Ala Arg Tyr Ile Thr Lys Thr Asn Ala
            180                 185                 190

Ser Thr Leu Asp Thr Phe Lys Ala Asn Glu Glu Gly Tyr Leu Gly Val
        195                 200                 205

Ile Ile Gly Asn Arg Ile Tyr Tyr Gln Asn Arg Ile Asp Lys Leu His
    210                 215                 220

Thr Thr Arg Ser Val Phe Asp Val Arg Gly Leu Thr Ser Leu Pro Lys
225                 230                 235                 240

Val Asp Ile Leu Tyr Gly Tyr Gln Asp Asp Pro Glu Tyr Leu Tyr Asp
                245                 250                 255

Ala Ala Ile Gln His Gly Val Lys Gly Ile Val Tyr Ala Gly Met Gly
            260                 265                 270

Ala Gly Ser Val Ser Val Arg Gly Ile Ala Gly Met Arg Lys Ala Met
        275                 280                 285

Glu Lys Gly Val Val Val Ile Arg Ser Thr Arg Thr Gly Asn Gly Ile
    290                 295                 300

Val Pro Pro Asp Glu Glu Leu Pro Gly Leu Val Ser Asp Ser Leu Asn
305                 310                 315                 320

Pro Ala His Ala Arg Ile Leu Leu Met Leu Ala Leu Thr Arg Thr Ser
                325                 330                 335

Asp Pro Lys Val Ile Gln Glu Tyr Phe His Thr Tyr
            340                 345


<210> SEQ ID NO 5
<211> LENGTH: 118
<212> TYPE: PRT
<213> ORGANISM: Homo sapiens

<400> SEQUENCE: 5

Met Ser Gly Gly Gly Pro Ser Gly Gly Gly Pro Gly Gly Ser Gly Arg
1               5                   10                  15

Ala Arg Thr Ser Ser Phe Ala Glu Pro Gly Gly Gly Gly Gly Gly Gly
            20                  25                  30

Gly Gly Gly Pro Gly Gly Ser Ala Ser Gly Pro Gly Gly Thr Gly Gly
        35                  40                  45

Gly Lys Ala Ser Val Gly Ala Met Gly Gly Gly Val Gly Ala Ser Ser
    50                  55                  60

Ser Gly Gly Gly Pro Gly Gly Ser Gly Gly Gly Gly Ser Gly Gly Pro
65                  70                  75                  80

Gly Ala Gly Thr Ser Phe Pro Pro Pro Gly Val Lys Leu Gly Arg Asp
                85                  90                  95

Ser Gly Lys Val Thr Thr Val Val Ala Thr Leu Gly Gln Gly Pro Glu
            100                 105                 110
```

-continued

```
Arg Ser Gln Glu Val Ala
        115


<210> SEQ ID NO 6
<211> LENGTH: 55
<212> TYPE: PRT
<213> ORGANISM: Homo sapiens

<400> SEQUENCE: 6

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser
    50                  55
```